(12) United States Patent
Everson

(10) Patent No.: US 8,778,299 B2
(45) Date of Patent: *Jul. 15, 2014

(54) METHODS FOR DIAGNOSIS AND INTERVENTION OF HEPATIC DISORDERS

(75) Inventor: Gregory Thomas Everson, Englewood, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 528 days.

This patent is subject to a terminal disclaimer.

(21) Appl. No.: 12/557,916

(22) Filed: Sep. 11, 2009

(65) Prior Publication Data

US 2010/0055734 A1    Mar. 4, 2010

Related U.S. Application Data

(63) Continuation-in-part of application No. 11/814,793, filed as application No. PCT/US2006/003132 on Jan. 26, 2006.

(60) Provisional application No. 60/647,689, filed on Jan. 26, 2005.

(51) Int. Cl.
*A61K 51/00* (2006.01)

(52) U.S. Cl.
USPC ........................................................ 424/1.45

(58) Field of Classification Search
USPC ........................................................ 424/1.45
See application file for complete search history.

(56) References Cited

U.S. PATENT DOCUMENTS

| | | | |
|---|---|---|---|
| 4,207,308 A | 6/1980 | Spenney | |
| 6,778,269 B2 | 8/2004 | Fink et al. | |
| 8,613,904 B2 | 12/2013 | Everson et al. | |
| 2006/0067881 A1 | 3/2006 | Groman et al. | |
| 2006/0251576 A1 | 11/2006 | Hellerstein | |
| 2008/0279766 A1 | 11/2008 | Everson et al. | |
| 2010/0055734 A1 | 3/2010 | Everson | |
| 2012/0329161 A1 | 12/2012 | Everson et al. | |
| 2014/0067276 A1 | 3/2014 | Everson et al. | |

OTHER PUBLICATIONS

Chronic hepatitis data sheet: 2010-2011, 1 page.*
Hechey et al. "Syntheses with stable isotopes: synthesis of deuterium and 13C labeled bile acids", J of Labelled Compounds, 1973, IX(4):703-719.*
Dax et al. "HPLC-continuous-flow fast atom bombardment mass spectrometry (HPLC-CFFAB)-a convenient method for the analysis of bile acids in bile and serum", Chromatographia, 1995, 40(11/12):674-679.*
Stellaard et al. "Simultaneous determination of cholic acid and chenodeoxycholic acid pool size and fractional turnover rates in human serum using 13C-labeled bile acids", J of Lipid Research, 1984, 25:1313-1319.*
Decompensated cirrhosis data sheet: 1 page, 2011.*
Denaro et al. (1996) Clinical Pharmacology and Therapeutics 59:624-635 "The effect of liver disease on urine caffeine metabolite ratios".
Di Bisceglie (2008) N. Engl J Med. Dec. 4, 2008 359(23):2429-41 "Prolonged therapy of advanced chronic hepatitis C with low-dose peginterferon.".
Everson et al. (2007) Alimentary Pharmacology & Therapeutics 26:401-410 "Portal-systemic shunting in patients with fibrosis or cirrhosis due to chronic hepatitis C: the minimal model for measuring cholate clearances and shunt".
Everson et al. (2008) Alimentary Pharmacology & Therapeutics 27:798-809 "The spectrum of hepatic functional impairment in compensated chronic hepatitis C: results from the Hepatitis C Anti-viral Long-term Treatment against Cirrhosis Trial".
Everson et al. (2009) Alimentary Pharmacology & Therapeutics 29:589-601 "Quantitative tests of liver function measure hepatic improvement after sustained virological response: results from the HALT-C trial".
Gilmore and Thompson (1980) Gut 21:123-127 "Plasma clearance of oral and intravenous cholic acid in subjects with and without chronic liver disease".
Golden et al. (Jun. 1994) American Journal of Veterinary Research 55(6):790-794 "Application of an enzyme-multiplied immunoassay technique for determination of caffeine elimination kinetics as a test of liver function in clinically normal dogs".
Guidance for Industry, Bioanalytical Method Validation, May 2001.
Hague and Yoshida (2009) Annals of Hepatology 8(1):Jan.-Mar: 78-79 "Hepatitis C antiviral long-term treatment against cirrhosis (HALT-C) trial".
Hoofnagle (2002) Hepatology 36(5):S21, Nov. 2002 "Course and outcome of hepatits C".
Hydzik et al. (2008) Clinical Toxicology 46:1077-1082 "Usefulness of 13C-methacetin breath test in liver function testing in *Amanita phalloides* poisoning: breast feeding woman case".
International Search Report dated Jul. 11, 2007 for PCT/US06/03132.
Koster and Ooms (Dec. 2001) Guide to LC-MS, 3 pp. "Recent Developments in On-line SPE for HPLC and LC-MS in Bioanalysis".
Krumbiegel et al. (Mar. 1990) Eur J Pediatr. 149(6):393-5 "[15N]methacetin urine test: a method to study the development of hepatic detoxification capacity".
Lalazar et al. (Oct. 2008) Journal of Viral Hepatitis 15(10):716-28 "A continuous 13C methacetin breath test for noninvasive assessment of intrahepatic inflammation and fibrosis in patients with chronic HCV infection and normal ALT".
Martucci (Aug. 2004) research paper, University of Colorado Health Sciences Center "Deconvolutional Analysis on Clearance Curves of Simultaneously Administered Oral and Intravenous Doses of 2,2,4,4-2H Cholate and 24-13C Cholate: Minimal Model to Determine First-Pass Hepatic Extraction of Cholate in Humans".

(Continued)

*Primary Examiner* — Bin Shen
(74) *Attorney, Agent, or Firm* — Merchant & Gould PC

(57) ABSTRACT

The disclosure provides a method for quantification of hepatic function in a subject comprising measuring the clearance of an orally administered isotopically labeled cholic acid in a subject with, or suspected of having or developing, a hepatic disorder, for example, chronic hepatitis C. The disclosure further provides methods and kits for assessment of hepatic function.

34 Claims, 15 Drawing Sheets

(56) References Cited

OTHER PUBLICATIONS

"Qualitative Tests (QLFTS) Detect Impaired Hepatic Function in a High Proportion of Patients with Chronic HCV and Firbrosis or Cirrhosis and May Predict Risk of Cirrhosis, Splenomegaly and Varices", presentation at the 54th Annual Meeting of the American Association for the Stady of Liver Diseases, Oct. 2003.

Queiroz and Lancas (Oct. 2004) LCGC North America 22(10).

Rector et al. (1990) Hepatology 12:455-459 "Renal sodium retention complicating alcoholic liver disease: relation to portosystemic shunting and liver function".

Renner et al. (1984) Hepatology 4(1):38-46 "Caffeine: A Model Compound for Measuring Liver Function".

Shrestha et al. (Mar. 1997) Liver Transplantation and Surgery 3(2):166-167,172 "Quantitative liver function tests define the functional severity of liver disease in early-state cirrhosis".

Invitation to Pay Additional Fees for PCT/US10/47676 mailed Nov. 17, 2010, 2pages.

Medrzejewski, et al., Plasma clearance of cholic acid in patients with chronic diseases of the liver, Polski Tygodnik Lekarski, Apr. 16-30, 1990; 45 (16-18):335-7. Abstract Only, 1 page.

International Search Report and Written Opinion, PCT/US 10/47976, dated Feb. 2, 2011, 14 pages.

Extended European Search Report (EP 06734026.5) dated Mar. 31, 2011.

Everson, G. T. et al. (2003): "Quantitative Tests (QLFTS) Detect Impaired Hepatic Function in a High Proportion of Chronic Hepatitis C Patients With Fibrosis or Compensated Cirrhosis and may Predict Risk of Cirrhosis, Splenomegally, and Varices"; Hepatology, vol. 38, Jan. 1. 2003, pp. 304-305.

Everson et al. (2009) Hepatology 50(4 Suppl.):1057A, Abstract 1627 "Hepatic Impairment Measured by Quantitative Tests of Liver Function (QLFTs) Predicts Clinical Outcome in Patients with Advanced Fibrosis: Results from the Hepatitis C Anti-viral Long-term Treatment against Cirrhosis (HALT-C) trial".

European Search Report for Application No. 10815965.8 mailed Apr. 17, 2013.

International Search Report and Written Opinion cited in PCT/US2012/040008 mailed Sep. 6, 2012.

Helmke, S. et al., "Slow, Moderate, and Rapid Progressors: Three Distinct Categories of Patients with Primary Sclerosing Cholangitis Detected by Functional Assessment using Cholate Testing," *Hepatology*, vol. 56, No. 4 (Suppl), Abstract No. 2027, p. 1133A (Oct. 2012).

International Search Report and Written Opinion for PCT/US13/69708 mailed Feb. 10, 2014.

Kamath, P. et al., "A Model to Predict Survival in Patients with End-Stage Liver Disease," *Hepatology*, vol. 33, No. 2, pp. 464-470 (Feb. 2001).

\* cited by examiner

METHODS FOR DIAGNOSIS AND INTERVENTION OF HEPATIC DISORDERS

RELATED APPLICATIONS

This application is a continuation-in-part of U.S. application Ser. No. 11/814,793, with a §371 date of May 13, 2008, now U.S. Pat. No. 8,613,904, issued Dec. 24, 2013, which is the national phase under 35 U.S.C. §371 of PCT International Application No. PCT/US06/03132, which has an International filing date of Jan. 26, 2006, which designated the United States of America and which claims the benefit of U.S. Provisional Application Ser. No. 60/647,689, filed Jan. 26, 2005, the entire contents of each of which is incorporated herein by reference.

STATEMENT REGARDING FEDERALLY SPONSORED RESEARCH

This invention was made with government support under Contract No. N01-DK-9-2327 and Grant No. M01RR-00051 awarded by the National Institutes of Health. The government has certain rights in the invention.

BACKGROUND OF THE INVENTION

Chronic hepatitis C affects 4 million patients in the United States, and results in 10,000 deaths annually. Major clinical consequences of chronic liver disease are related to the effect of hepatic fibrosis in producing portal hypertension and in the progressive decline of the functioning hepatic mass. Currently, measuring clearance rates of substances primarily removed from circulation by the liver provides the most sensitive, non-intrusive and specific indicator of liver function.

In humans, the two primary bile acids synthesized by the liver are cholic acid and chenodeoxycholic acid, which are converted into secondary bile acids by intestinal bacteria. These bile acids are conjugated with glycine or taurine and secreted by the liver. Serum bile acid levels are determined by the balance between intestinal absorption and hepatic elimination of bile acid.

Cholic acid is an example of a model bile acid. Orally administered cholic acid is absorbed across the epithelial lining cells of the small intestine, bound to albumin in the portal blood, and transported to the liver via the portal vein. Approximately 80 to 85% of cholic acid is extracted from the portal blood in its first pass through the liver. Cholic acid that escapes hepatic extraction exits the liver via hepatic veins that drain into the vena cava back to the heart, and is delivered to the systemic circulation. The area under the curve (AUC) of peripheral venous concentration versus time after oral administration of cholic acid quantifies the fraction of cholic acid escaping hepatic extraction and defines "oral cholate clearance".

Intravenously administered cholic acid, bound to albumin, distributes systemically and is delivered to the liver via both portal venous and hepatic arterial blood flow. The AUC of peripheral venous concentration versus time after intravenous administration of cholic acid is equivalent to 100% systemic delivery of cholic acid. The ratio of the AUCs of orally to intravenously administered cholic acid, corrected for administered doses, defines cholate shunt.

After uptake by the liver, cholic acid is efficiently conjugated to either glycine or taurine and secreted into bile. Physicochemically cholic acid is easily separated from other bile acids and bile acid or cholic acid conjugates, using chromatographic methods.

An NIH-sponsored Hepatitis C Antiviral Long-Term Treatment against Cirrhosis (HALT-C) Trial examined whether long-term use of antiviral therapy (maintenance treatment) would slow the progression of liver disease. In noncirrhotic patients who exhibited significant fibrosis, effective maintenance therapy was expected to slow or stop histological progression to cirrhosis as assessed by serial liver biopsies. However, tracking disease progression with biopsy carries risk of complication, possibly death. In addition, sampling error and variation of pathologic interpretation of liver biopsy limits the accuracy of histologic assessment and endpoints. The histologic endpoint is less reliable because advanced fibrosis already exists and changes in fibrosis related to treatment or disease progression cannot be detected. Thus, standard endpoints for effective response to maintenance therapy in cirrhotic patients are prevention of clinical decompensation (ascites, variceal hemorrhage, and encephalopathy) and stabilization of liver function as measured clinically by Childs-Turcotte-Pugh (CTP) score. However, clinical endpoints and CTP score are insensitive parameters of disease progression.

In one proposal, studies were designed to analyze disease progression in a unique subset of patients with chronic hepatitis C, those with fibrosis and early, compensated cirrhosis. These patients are characterized by absence of clinical findings and normal or nearly normal values for standard routine biochemical parameters including serum albumin and prothrombin time. Child-Turcotte-Pugh scores will range from 5 to 6. For this reason, this subgroup of patients may benefit from quantitative tests of liver function that might be more useful than standard biochemical measurements, and more sensitive than clinical endpoints for evaluating the degree and progression of hepatic dysfunction.

Because early intervention of liver dysfunction is critical, a need exists for the detection of early signs that predict the onset or progression of a condition. A number of critical needs could be met by effective and accurate tests of hepatic function.

SUMMARY OF THE INVENTION

The disclosure provides a method for assessment and quantification of hepatic function in a subject comprising measuring the clearance of an orally administered isotopically labeled cholic acid to a subject suspected of having or developing a hepatic disorder, for example, chronic hepatitis C. The disclosure further provides methods and kits for assessment of hepatic function.

In one embodiment, the disclosure provides a method for assessment of hepatic function in a subject, the method comprising: administering orally an isotopically labeled cholic acid to a subject with, or suspected of having or developing, a hepatic disorder, wherein no additional cholic acid compound is intravenously co-administered; collecting samples from the subject over intervals for a period of less than 3 hours after administration of the agents to the subject; and measuring the clearance of the orally administered isotopically labeled cholic acid as an indicator of hepatic function in the subject. In one aspect, the isotopically labeled cholate is selected from 24-$^{13}$C cholic acid and 2,2,4,4-$^2$H cholic acid. In another aspect, the samples collected over an interval period of time comprise blood or serum samples. In another aspect, the samples are collected over a period of about 90 minutes or less. In a specific aspect, blood samples collected from the subject at 5, 20, 45, 60 and 90 minutes post-administration. In one aspect, the measuring step comprises quantifying the isotopically labeled cholic acid in the samples by GC-MS or HPLC-MS.

In another embodiment, the disclosure provides a method for assessment of hepatic function in a subject that comprises oral cholate clearance and at least one additional hepatic assessment test. In certain aspects, the additional hepatic assessment test is selected from clearance or metabolism of aminopyrine, clearance or metabolism of aminopyrine, clearance or metabolism of antipyrine, clearance or metabolism of bile acids other than cholate, clearance or metabolism of caffeine, clearance of or metabolism erythromycin, clearance or metabolism of nitroglycerin, clearance of or metabolism galactose, clearance or metabolism of indocyanine green, clearance or metabolism of lidocaine, clearance or metabolism of midazolam, clearance or metabolism of omeprazole, clearance or metabolism of dextromethorphan, clearance or metabolism of phenacetin, clearance or metabolism of methacetin, liver-spleen scan, serum bilirubin analysis, alanine aminotransferase analysis, aspartate aminotransferase analysis, and alkaline phosphatase analysis. In a further aspect, the additional hepatic assessment test is a multi-isotope test. In another aspect, the additional hepatic assessment test is a quantitative liver function test (QLFT). The quantitative liver function test (QLFT) is selected from a hepatic metabolic function test, a hepatic blood flow test or a combination of these tests. In a specific aspect, the hepatic metabolic function test is a multi-isotope caffeine test which comprises administering distinguishable caffeine solutions orally, intravenously or in combination. In a specific aspect, the administering step comprises administering three distinguishable caffeine solutions to a subject at different time intervals. In one specific aspect, a single sample is obtained sometime after administration of the distinguishable caffeine solutions to assess the hepatic condition of the subject.

In one embodiment, the clearance of the isotopically labeled cholic acid is used as an indication of a need for at least one therapeutic treatment of the subject with a hepatic disorder. In one aspect, the therapeutic treatment comprises an antiviral therapy. In another aspect, the hepatic disorder comprises chronic hepatitis C. In another embodiment, the clearance of the isotopically labeled cholic acid is used for assessment of the progression of at least one hepatic condition in a subject.

In one embodiment, the disclosure provides a method for determination of cholate shunt. This method can be used for assessment of the progression of at least one hepatic condition in a subject, the method comprising: administering orally a first distinguishable isotopically labeled cholic acid to a subject having, or suspected of having or developing, a hepatic disorder; co-administering intravenously a second distinguishable isotopically labeled cholic acid to the subject; collecting blood or serum samples over intervals for a period of less than 3 hours after administration of the agents to the subject; quantifying the first and the second isotopically labeled cholic acids in the samples by HPLC-MS; and calculating the cholate shunt using the formula: AUCoral/AUCiv× Doseiv/Doseoral×100%; wherein AUCoral is the area under the curve of the serum concentrations of the first cholic acid and AUCiv is the area under the curve of the second cholic acid; and wherein the cholate shunt is an indicator of the progression of at least one hepatic disorder of the subject. In one aspect, the orally administering of the first labeled cholic acid and the intravenously co-administering of the second labeled cholic acid are performed simultaneously. In another aspect, the collecting step comprises collecting samples over a period of about 90 minutes or less. In a further aspect, the samples comprise blood or serum samples collected from the subject at 5, 20, 45, 60 and 90 minutes post-dose.

In one aspect, the cholate shunt is an indicator of a need for at least one therapeutic treatment of the subject with a hepatic disorder. In a further aspect, the at least one therapeutic treatment comprises an antiviral therapy. In another aspect, the hepatic disorder comprises chronic hepatitis C.

In another embodiment, the disclosure provides a method for assessment of hepatic function in a subject that comprises cholate shunt and at least one additional hepatic assessment test. In certain aspects, the at least one additional hepatic assessment test is selected from clearance or metabolism of aminopyrine, clearance or metabolism of aminopyrine, clearance or metabolism of antipyrine, clearance or metabolism of bile acids other than cholate, clearance or metabolism of caffeine, clearance of or metabolism erythromycin, clearance or metabolism of nitroglycerin, clearance of or metabolism galactose, clearance or metabolism of indocyanine green, clearance or metabolism of lidocaine, clearance or metabolism of midazolam, clearance or metabolism of omeprazole, clearance or metabolism of dextromethorphan, clearance or metabolism of phenacetin, clearance or metabolism of methacetin, liver-spleen scan, serum bilirubin analysis, alanine aminotransferase analysis, aspartate aminotransferase analysis, and alkaline phosphatase analysis. In another aspect, the additional hepatic assessment test is a quantitative liver function test (QLFT), which may be a hepatic metabolic function test, a hepatic blood flow test or combination thereof.

In another embodiment, the disclosure provides a kit of components for determining one or both of cholate clearance and cholate shunt in a subject with, or suspected of having or developing, a hepatic disorder; the kit comprising a first component comprising one or more vials, each vial comprising a single oral dose of a first distinguishable cholate compound; and a second component comprising one or more vials, each vial comprising a single intravenous dose of a second distinguishable cholate compound. In one aspect, the kit further comprises a third component comprising one or more vials, each vial comprising a quantity of human serum albumin for mixing with a single intravenous dose of the second distinguishable cholate compound prior to intravenous administration. In another aspect, the kit further comprises one or more sets of labeled sterile blood-serum sample collection tubes. In a further aspect, the kit also comprises one or more sets of labeled transport vials, each transport vial containing an internal cholic acid standard. In one specific aspect, the kit also comprises a single box for both shipping the vials to a health care practitioner and shipping the samples from the health care practitioner to a reference lab for analysis. In another specific aspect, the first distinguishable cholate compound is 2,2,4,4-$^2$H cholic acid and the second distinguishable agent is 24-$^{13}$C cholic acid. In a further specific aspect, the $^2$H-cholic acid is in a powder form or in a solution form.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

DETAILED DESCRIPTION OF THE INVENTION

Figure 1:
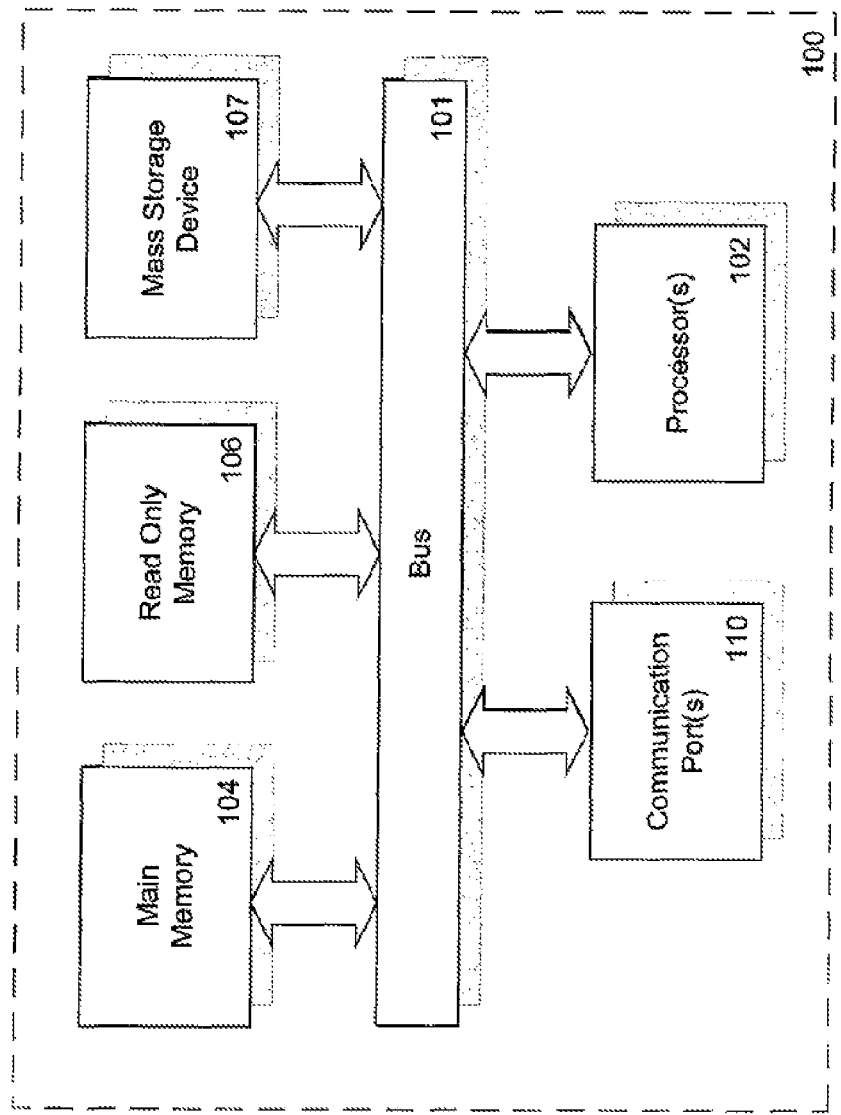
FIG. 1 illustrates an exemplary computing device.

In the following section, several methods are described to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description in order to prevent unnecessary masking of various embodiments.

Definitions and Acronyms

As used herein, "a" or "an" may mean one or more than one of an item. As used herein "clearance" may mean the removing of a substance from one place to another. As used herein the specification, "subject" or "subjects" may include but are not limited to mammals such as humans or mammals for example dogs, cats, ferrets, rabbits, pigs, horses, cattle to birds, or reptiles. Other definitions are provided throughout the specification.

The acronym "HALT-C" refers to the Hepatitis C Antiviral Long-term Treatment against Cirrhosis trial. The HALT-C trial was a large, prospective, randomized, controlled trial of long-term low dose peg interferon therapy in patients with advanced hepatitis C who had not had a sustained virologic response to a previous course of interferon-based therapy.

The acronym "IV" or "iv" refers to intravenous.

The acronym "PO" refers to per oral.

The acronym "PHM" refers to perfused hepatic mass.

The acronym "MEGX" refers to monoethylglycinexylidide, a metabolite of lidocaine.

The acronym "SF" refers to shunt fraction, for example, as in cholate SF.

The acronym "$Cl_{oral}$" refers to clearance of an orally administered cholate compound.

The acronym "$Cl_{iv}$" refers to clearance of an intravenously administered cholate compound.

The acronym "ROC" refers to receiver operator curve.

The acronym "QLFT" refers to Quantitative Liver Function Test.

The term "Ishak Fibrosis Score" is used in reference to a scoring system that measures the degree of fibrosis (scarring) of the liver, which is caused by chronic necroinflammation. A score of 0 represents no fibrosis, and 6 is established fibrosis. Scores of 1 and 2 indicate degrees of portal fibrosis; stages 3 and 4 indicate bridging fibrosis. A score of 5 indicates nodular formation and incomplete fibrosis.

In one embodiment, Quantitative Liver Function Tests (QLFTs), such as assays that measure the liver's ability to metabolize or extract test compounds, can identify patients with impaired hepatic function at earlier stages of disease, and possibly define risk for cirrhosis, splenomegaly, and varices. One of these assays is the cholate shunt assay where the clearance of cholate is assessed by analyzing bodily fluid samples after exogenous cholate has been taken up by the body.

In one aspect, QLFTs can be used to measure hepatic disease progression. Investigators have used the clearance or measurement of metabolites of aminopyrine, antipyrine, bile acids, propranolol, midazolam, dextromethorphan, methionine, methoximine, caffeine, erythromycin, galactose, indocyanine green, lidocaine, phenacetin and methacetin to assess hepatic function. In certain aspects, multiple isotopes of any of these compounds may be utilized to assess hepatic function. For example, differentiable isotopes of a particular compound can be administered by different routes of administration. Clearances of test compounds are typically defined as dependent upon either hepatic metabolism (aminopyrine, antipyrine, caffeine, erythromycin) or hepatic blood flow (bile acids, indocyanine green).

Each quantitative test has advantages and disadvantages over other tests and few studies have compared multiple tests within the same cohort of patients. Studies herein such as QLFTs in HALT-C patients represent a comprehensive comparison of 12 QLFTs, using 8 test compounds, in the same patient. Also, these studies represent patients with chronic hepatitis C and advanced fibrosis using quantitative tests to predict outcome and measuring changes in hepatic function over prolonged periods of time (e.g. 4-6 years).

The most commonly used quantitative tests assess hepatic metabolic capacity. Aminopyrine (dimethylaminoantipyrine) is metabolized primarily by N-demethylation. The hepatic capacity to metabolize aminopyrine can be measured from the specific activity of $[^{14}CO_2]$ in breath samples obtained two hours after oral administration of a tracer dose of [$^{14}$C] aminopyrine. A related compound, antipyrine, is extensively metabolized by a group of cytochrome P450 dependent liver microsomal enzymes; only 5% of the drug appears unchanged in the urine. The plasma or salivary disappearance of antipyrine follows first order kinetics and obeys a simple, one-compartment model. As with all drugs whose clearance is primarily dependent upon metabolism, elimination is not greatly influenced by changes in hepatic blood flow. The main problem with use of these compounds is the reported low rate of severe bone marrow depression, including anemia. There has been one reported fatality due to an overwhelming hypersensitivity reaction in response to a single dose. Antipyrine is also not readily available for use in humans.

Phenacetin differs from aminopyrine in that its metabolism is mediated by cytochrome P448 and the [$^{14}$C] phenacetin breath test is another technique to measure hepatic function in humans.

Methacetin can also be used to evaluate hepatic metabolism. For example, a [15N]methacetin urine test can be used to study human O-demethylase activity to characterize hepatic detoxification capacity following oral administration of an aqueous solution. (Krumbiegel at al., [$^{15}$N]Methacetin urine test: A method to study the development of hepatic detoxification capacity, 1990, European J. Pediatrics, 149(6); 393-395). In another example, a continuous [$^{13}$C] methacetin breath test (13C-MBT, BREATHID®) can be used for assessment of hepatic microsomal enzyme function (cytochrome P450 CYP1A2) following oral administration of methacetin. (Lalazar et al., A Continuous 13C Methacetin Breath Test for Noninvasive Assessment of Intrahepatic Inflammation and Fibrosis in Patients with Chronic HCV Infection and Normal ALT., 2008, J. Viral Hepatitis, 15(10):716-728).

Caffeine has been used as a test compound for quantitative assessment of the liver because of its relative lack of toxicity, rapid absorption, its complete metabolism by the liver, and its ready availability. Caffeine is eliminated by first order kinetics but pathways of metabolism are sometimes extensive and complex. A disadvantage of previous caffeine tests is that caffeine is ubiquitously found in a wide variety of commonly ingested foodstuffs, supplements, and medications; ingestion of caffeine from these sources typically invalidates results of most standard caffeine assays. In addition, the metabolism and clearance of caffeine can be altered by coadministration of drugs or medications.

Erythromycin is eliminated primarily by n-demethylation by hepatic cytochrome P450 enzymes, predominantly CYP3A4 (cytochrome P450 3A4). Numerous xenobiotics, including up to 50% of prescribed medications, are metabolized through the CYP3A4 pathway and may enhance or inhibit erythromycin clearance and metabolism. These effects invalidate the use of erythromycin as a liver function test.

Galactose elimination is complicated by extrahepatic metabolism. Approximately 60% of the total plasma elimination of galactose after a single intravenous injection is due to hepatic clearance; the remaining 40% is due to distribution and metabolism of galactose outside the liver. Thus, galactose elimination capacity is only partially a liver function test.

Other Tests Assess Flow-Dependent Hepatic Clearance.

Indocyanine green (ICG), when administered intravenously is removed from the circulation by the liver with a first-pass hepatic extraction up to 80%. After uptake by the liver, indocyanine green is transported to bile without metabolic transformation. However, as is true of other intravenously administered test compounds, ICG is insensitive and cannot detect early stage disease or small changes in the hepatic condition.

Lidocaine is initially cleared by the liver in a flow-dependent fashion; first pass elimination is up to 81%. Once taken up by the liver, lidocaine is metabolized by oxidative N-demethylation (cytochrome P450 3A4) to monoethylglycinexylidide (MEGX). MEGX concentrations are a result of rapid hepatic uptake and clearance from the blood followed by hepatic metabolism and have been used to assess hepatic function in potential liver donors, in liver transplant recipients, and in predicting survival in patients with cirrhosis. Early results suggest that lidocaine-MEGX is useful in assessing short-term prognosis in cirrhotic patients independent of the cause of the underlying liver disease. However, MEGX is subject to the same concerns raised above for intravenously administered compounds (ICG) and its blood level may be affected by interference from coadministered medications, supplements, or dietary factors.

Bile acids are naturally-occurring compounds that exhibit flow-dependent hepatic clearance. Dual isotope techniques allow measurement of first-pass hepatic elimination of bile acids from the portal circulation. Flow-dependent, first pass elimination of bile acids by the liver ranges from 60% for unconjugated dihydroxy, bile acids to 95% for glycine-conjugated cholate. Free cholate, used herein has a reported first-pass elimination of approximately 80% which agrees closely with observed first pass elimination in healthy controls of about 83%. Plasma clearance of oral and intravenous cholic acid in subjects with and without chronic liver disease were studied. These studies demonstrated reduced clearance of cholate in patients who had either hepatocellular damage or portosystemic shunting.

Liver-spleen scans are an effective measure of many parameters affected by chronic liver disease. The liver-spleen scan is useful when the parameters measured are given quantitative expression by SPECT analysis. These parameters can include: 1) precise measurement of sulfur colloid distribution, 2) organ volumes functional 3) organ volumes and/or non-functional volume ratios. Sulfur colloid distribution is determined by Kupffer cell extraction of sulfur colloid and hepatic blood flow. Increased sulfur colloid distribution to spleen and bone marrow is due to either decreased hepatic extraction or decreased hepatic perfusion, both of which are determined by hepatic fibrosis. Thus, precise measurement of this distribution from planar measurement as a redistribution ratio (RR) or from volumetric parameters such as the perfused hepatic mass (PHM) correlates with ICG clearance and other tests of hepatocyte function. In one embodiment, any liver-spleen scan technique known in the art may be combined with any metabolic or clearance assay disclosed herein.

Typically, the PHM remains normal (>100) as scar tissue builds up in the liver until cirrhosis is well established. Once cirrhosis is established the PHM measurement deteriorates proportional to liver disease severity. For example, the PHM range is below the normal range (PHM=100-120) with compensated cirrhosis (PHM=80-110), lower still with ascites and variceal bleeding (PHM=40-80), and generally less than sixty in cirrhotic patients who die or require transplant. The non-fibrotic mass (functional hepatic mass) in a group of cirrhotic patients whose liver was removed at transplant or autopsy correlated closely with the PHM (correlation coefficient 0.95).

Areas of critical need for noninvasive QLFTs include, but are not limited to the following: detection of fibrosis and early cirrhosis (e.g. to avoid liver biopsy); detection of risk of varices (e.g. identification of patients who might benefit from endoscopy therapy); assessment of likelihood to respond to antiviral therapy (e.g. more refined selection of patients for treatment); defining level of hepatic impairment prior to treatments that might affect or could be affected by liver function (e.g. more precise definition of the level of hepatic impairment); selection of patients for transjugular intrahepatic portal-systemic shunt (TIPS) placement, or defining impairment prior to institution of chemotherapeutic agents to treat cancer; tracking disease progression (e.g., early detection of decompensation); and measurement of the effects of therapies or interventions (e.g., the changes in QLFTs may occur long before clinical deterioration and QLFTs would have increased sensitivity at detecting changes in the hepatic condition induced by the treatment/intervention; therefore, a smaller sample size could be utilized in defining effects).

Non-invasive tests have been used for prediction of fibrosis or cirrhosis. Methods include models using standard laboratory tests and other blood components, clearance of test compounds, Doppler ultrasonography, transient ultrasonographic elastography and magnetic resonance elastography. However, none of these methods accurately quantifies the portal circulation or portal-systemic shunting. In contrast, the cholate method disclosed herein not only quantifies the portal circulation and portal-systemic shunting, but also correlates well with cirrhosis, varices and variceal size.

In HALT-C patients, cholate $Cl_{oral}$ and cholate shunt compared favorably to other quantitative tests of liver function. They correlated better with cirrhosis, varices, standard laboratory tests and response to antiviral therapy than caffeine elimination, antipyrine elimination and clearance, galactose elimination capacity, MEGX generation from lidocaine and methionine breath test. In a study of other patients, cholate $Cl_{oral}$ and cholate shunt were better than caffeine elimination or antipyrine elimination and clearance in identifying patients at risk of future decompensation.

Combination Tests-Quantitative Tests of Liver Function (QLFTs).

Comprehensive assessment of functional hepatic reserve may require one reliable quantitative test or a combination of quantitative liver function tests. However, few, if any, studies have compared the results of more than two tests within the same cohort of patients largely because of the complexity of some of the tests.

In one study herein, QLFTs in HALT-C patients were examined for the utility of multiple QLFTs in predicting cirrhosis and varices. These analyses indicated that cholate shunt and oral cholate clearance were useful and complementary to standard clinical assessment in prediction of both cirrhosis and varices. In addition, QLFTs correlated not only with clinical and laboratory measures of hepatic function but also predicted response to antiviral therapy. One advantage of these tests is the use of a combination of quantitative tests to comprehensively define hepatic function in selected and controlled populations. These tests provide critical information necessary for the understanding of functional hepatic capacity and recovery for most if not all liver conditions.

One quantitative test for hepatic condition is Cholate Clearance. Clearance of cholate is dependent upon specific high-affinity transport proteins located on the sinusoidal surface of hepatocytes and is proportional to hepatic blood flow and hepatocyte function. Clearance of cholate from portal blood or first-pass hepatic extraction, can be measured in humans using dual isotopes (e.g. stable isotopes) and simultaneous oral and intravenous administration. Simultaneous administration is defined by administration of oral and intravenous test compounds within 5 minutes of each other. Stable ($^{13}C$, $^{2}H$, $^{15}N$, $^{18}O$) or radioactive isotopes ($^{14}C$, $^{3}H$, Tc-99m) can be used. Advantages of stable isotopes are the lack of exposure to radioactivity, natural abundance, and the specificity of the analyses used for test compound identification (mass determination by mass spectrometry). Cholate escaping hepatic extraction enters the systemic circulation and is defined as the cholate shunt. In patients in the previously mentioned HALT-C trial, cholate shunt correlated with for example cirrhosis on liver biopsy, varices on endoscopy, splenomegaly on ultrasonography, platelet count (a reflection of infection), and biochemical markers of disease severity. In this study the method of measuring the cholate shunt required sampling of blood for at least 3 hours resulting in prolonged discomfort and delay to the patient. In one embodiment, a cholate clearance test can be used alone, or in combination with other hepatic assessment tests.

One Quantitative Liver Function Test (QLFT) is the Cholate Shunt assay. A cholate shunt assay determines a relative value for predicting clinical outcome or monitoring of hepatic disease progression. In one embodiment of the invention, $^{13}C$-cholate is administered intravenously and $^{2}H4$-cholate is administered orally to a subject suspected of having or developing a liver disorder. In accordance with this embodiment, blood samples for measurement of cholate isotopes are obtained at a baseline and several times after the baseline. For example, samples may be taken at 5, 10, 15, 20, 30, 45, 60, 75, 90, 105, 120, 150 and less than 180 minutes post-dose where a total of 14 blood samples may be collected over 180 minutes. Alternatively, fewer samples may be obtained. In another aspect, five samples are collected at 5, 20, 45, 60 and 90 minutes post-administration. In a further aspect, samples are collected up to a half an hour after administration of cholate. From these samples, intravenous and oral cholate clearance curves can be generated. The least squares method can be used to determine the area under the cholate clearance curves. Next, the liver shunt fraction, an indicator of liver function, is calculated using a method described in the Exemplary Operations section.

In order to reduce patient discomfort, time and resources, in one embodiment a deconvolutional analysis may be used to generate intravenous and oral distinguishable agent clearance curves. To assess one or more hepatic conditions in a subject in the optimal amount of blood draws and time, spline functions, calculated elimination rates and direct integration of mathematical equations may be used to reduce the number of blood draws and reduce the time required for assessment.

Each of the above tests has certain advantages and disadvantages but few studies have examined the value of quantitative tests or compared the relative benefits of individual tests in either predicting disease progression or in monitoring response to long-term maintenance therapy. The present invention proposes quantitative tests that may predict outcome and therapeutic endpoints, in subjects with a liver condition (e.g., chronic hepatitis C with compensated cirrhosis).

In an earlier study, hepatic function was compared between Childs-Turcotte-Pugh A cirrhotics and normal controls by measuring the clearances of antipyrine, caffeine, and cholate labeled with stable isotopes, and cholate shunt. First, Childs-Turcotte-Pugh A cirrhotics were chosen because use of QLFTs to quantify the degree of hepatic impairment in cirrhotics with obvious clinical deterioration (Childs-Turcotte-Pugh B and C) was assumed to be of little additional utility above standard liver tests and clinical assessment. Second, the existing literature suggests that Childs-Turcotte-Pugh A cirrhotics likely have a wide range of hepatic functional impairment ranging from nearly normal to severely abnormal making this condition ideal for studying functional differences by QLFTs. Quantitation of liver function within this group might yield cutoffs for test results more likely to predict subsequent clinical outcome. Third, the use of multiple tests allowed comparison of the predictive value of a number of quantitative tests. Specifically, these tests may provide whether compounds cleared by hepatic metabolism including, but not limited to, for example caffeine and antipyrine or those whose clearance was flow dependent including but not limited to cholate, lidocaine, inderol, and nitroglycerine are informative with respect to functional reserve and risk of decompensation.

These studies revealed that the hepatic clearances of the administered compounds were significantly reduced in patients with cirrhosis but the range of functional impairment overlapped into the range of healthy controls. Five patients decompensated and required hepatic transplant or died from liver failure. Caffeine elimination or antipyrine clearance failed to separate these 5 patients from the cirrhotics who remained stable.

In contrast, the clearance of orally-administered cholate and first-pass elimination of cholate (cholate shunt) correlated with the patients who ultimately demonstrated evidence of decompensated liver disease during the follow-up period. The values for oral cholate clearance and cholate shunt in decompensated patients differed from the values measured for stable patients. These results indicated that quantitative tests, in particular dual cholate clearance, identified Childs-Turcotte-Pugh Class A cirrhosis patients at greatest risk for decompensation. Although the study focused on CTP Class A patients, the results may also be valid for patients with more advanced disease (CTP Class B or C) especially in prediction of severe complications (ascites, variceal hemorrhage, encephalopathy), hepatoma, or need for transplantation.

Thus, in one embodiment of the present invention, patients with Childs-Turcotte-Pugh Class A (and possibly CTP class B or C) cirrhosis may be tested for hepatic health. In a more particular embodiment, the cholate shunt assay detailed herein may be used to evaluate patients with Childs-Turcotte-Pugh Class A cirrhosis to analyze hepatic health. In another embodiment, a dual cholate clearance and shunt test may be used to evaluate patients with Childs-Turcotte-Pugh Class A cirrhosis to analyze hepatic health. In another embodiment, a dual cholate clearance and shunt test may be used to evaluate patients with Childs-Turcotte-Pugh Class A cirrhosis to analyze hepatic health in order to assess the need for therapeutic intervention. Alternatively, a cholate shunt assay and/or an oral cholate clearance assay may be used to assess hepatic health of a subject undergoing a therapeutic treatment for a liver condition such as, but not limited to, Childs-Turcotte-Pugh Class A cirrhosis.

In one embodiment, quantitative testing of hepatic function is useful for predicting outcome in a subject with fibrotic liver disease otherwise clinically stable with no biochemical or clinical decompensation. In addition, quantitative tests are useful as therapeutic assessments in patients who have mild hepatic dysfunction around baseline and who achieve a positive therapeutic response. In addition, QLFTs may also measure rate of disease progression during the course of a trial where lack of response or failure to receive therapy is likely to further impair hepatic function.

Cholic acid is the primary breakdown product from cholesterol. The adult pool size is from 1 to 3 grams. Thus the doses for administration suggested herein: from 20 to 60 mg, increase the cholate pool size no more than about 6%, an expansion that is unlikely to alter the normal metabolism of cholate in the human body. Given the enterohepatic cycling of cholate and about 5% loss with each cycle, 30 to 50% of administered cholate is eliminated each day; within 5 days, virtually all administered cholate is eliminated from the human body. Stable isotopically labeled compounds are commercially available. For example, $^{13}$C— and $^2$H— labeled cholic acid compounds can be purchased from Sigma-Aldrich, CDN Isotopes and Cambridge Isotope Laboratories, Inc.

The selection of the correct intravenous dose of labeled cholic acid is important; the IV dose must be safe, not cause injection site reaction, remain in the intravascular space, and achieve physiologic blood/serum concentrations. For accurate assessment of the cholate shunt the intravenous dose of labeled cholate must be restricted to the intravascular compartment and maintain residence in this space. Cholate is physiologically bound to albumin by interaction with specific domains within the albumin molecule. If cholate were injected directly into a peripheral vein, unbound to albumin, free cholate could diffuse into extravascular spaces or injure the vein into which it is injected. In one aspect of the invention, the labeled cholic acid intended for intravenous administration is prebound to albumin; specifically human serum albumin. Human serum albumin is FDA approved for use in humans. In one aspect, a dose of albumin is chosen that ensures complete binding of the labeled cholic acid. In one specific aspect, 5 mL of 25% human serum albumin is prebound to 20 mg labeled cholate prior to intravenous administration. Selection of the injection site for intravenous administration of labeled cholate should be such that adequate vein diameter allows for successful cannulation in nearly all cases. In one aspect, the antecubital vein is an appropriate injection site. In a specific aspect, the 10 mL volume of the intravenous dose is easily administered within a one minute interval by bolus injection.

The use of albumin-bound cholate maintains cholate in the intravascular space. Although the intravascular space includes serum and plasma; albumin is resident in serum, not plasma. By using albumin, the labeled cholate resides in serum, avoiding non-specific binding to clotting factors. Albumin binding also avoids diffusion of cholate into circulating cells such as red cells, WBCs, or platelets. Serum is easy to transport to a central laboratory for subsequent processing and analysis. Further, cholate is not degraded by constituents of serum. Although freezing of the serum sample is recommended for long term storage or transport, it is not necessary, so long as risk of evaporation is eliminated by securely fastened tubes.

Clearance of the IV dose is related to, or represents, total hepatic blood flow. Clearance=[hepatic blood flow]×[hepatic extraction of cholate]. Hepatic extraction of cholate=[uptake per cell]×[number of cells].

In one embodiment, the dosage form for oral administration of the labeled cholate is a solution form. Intestinal absorption and bioavailability of administered cholate is best achieved from a solution form. In one embodiment, the dissolution solution for oral administration of labeled cholate is a bicarbonate solution. Cholate is easily dissolved in aqueous sodium bicarbonate. A solution of sodium bicarbonate and cholate is not very palatable, so in one aspect, flavoring is used to improve acceptance of the orally administered dose. The flavoring can be natural or artificial. In a specific aspect, the solution of labeled cholate in sodium bicarbonate is a solution of a non-citrus juice, such as apple or grape juice.

Certain methods of the invention comprise administration of isotopically labeled cholate. In one exemplary method about 20 mg of 24-$^{13}$C cholic acid was mixed with 5 ml 25% human albumin and injected through an intravenous catheter over 2 min. In another exemplary method about 40 mg of 2,2,4,4-$^2$H cholic acid was dissolved in NaHCO$_3$ aq. and taken orally. In one example, blood was drawn at baseline and 5, 10, 15, 20, 30, 45, 60, 75, 90, 105, 120, 150 and less than 180 minutes post-dose.

In one exemplary method, the cholates are isolated by extraction from serum with Sep-Pak C18 cartridge, acidification, ether extraction, methylation, TMS derivatization and capillary GC-MS isotope ratiometry.

The cholate shunt calculation is based on $AUC_{po}/AUC_{iv}$ which is corrected for administered dose-Dose $i_v$/Dose$_{po}$. The cholate shunt is expressed as 100% to allow a range for reporting that is easy to comprehend and relate to the provider of healthcare and the patient, and is a number that can be easily followed. In one exemplary method, the Cholate shunt (%) may be calculated as $$AUC_{oral}/AUC_{iv} \times Dose_{iv}/Dose_{oral} \times 100\%.$$

Published methods for sample preparation of serum bile acids for either GC-MS or LC-MS are multistep, complex, and typically require several days. In one embodiment of the disclosure, an improved method of sample analysis is provided. In this embodiment sample processing for HPLC-MS is straightforward, rapid and does not require sample derivitization, in contrast to GC-MS sample preparation. In one embodiment, sodium hydroxide is added to the serum samples, samples are subjected to solid phase extraction by passage over SepPak C18 cartridges, samples are eluted from cartridges, the samples are dried, the samples are acidified with an HCl solution and extracted with ether. The ether is dried and samples are taken into the HPLC mobile phase buffer. Samples are added to an autosampler and subjected to HPLC-MS with selective ion monitoring.

In one aspect, analysis of MS data for peak area determination and subsequent calculations for Excel spreadsheet or other spreadsheet or data analysis software can be performed by the HPLC-MS software package. In another aspect, HPLC-MS data can be automatically transferred to PC workstations. In another aspect, conversion of peak areas to cholate concentration is performed using standard or calibration curves. In a further aspect, baseline measurement of natural abundance is also performed. In one aspect, unlabeled cholate in excess, e.g., 3 ug/mL, is used as an internal standard for quantifying the isotopically labeled cholates. In another aspect, correction for ion overlap between administered isotopes is performed using simultaneous equations for solving minor ion bleed-over and contamination of ion peaks. In a further aspect, determination of unlabeled cholate is performed on baseline samples. In another aspect, quality control samples bracket the characteristic concentrations achieved during performance of the IV and PO clearance tests. In one embodiment, the area under the curve (AUC) for administered isotopes of cholate is performed by plotting the concentration of the cholate in the sample versus time. In one aspect, a minimal model for accurate determination of AUC utilizes five sample collection times over 90 minutes. In a specific aspect, the blood samples are collected at 5, 20, 45, 60 and 90 minutes post-dose.

In one embodiment, the data is reported to the healthcare provider in any one of several formats. In certain aspects, the data can be reported out to the health care provider as one or more of cholate clearance for orally administered cholate, the cholate clearance for intravenously administered cholate, the cholate shunt, Cholate Kelim, Cholate Vd, total hepatic blood flow, apparent shunted volume. In another aspect, data can be corrected for weight, body mass index, and ideal body weight. In certain aspects, the risk of varices, size of varices, risk of cirrhosis, and stage of fibrosis can also be reported.

General Considerations for the Cholate Shunt

In one embodiment, the present invention concerns detecting cholate in a sample of a subject for prediction of the onset or progression of a hepatic condition.

Healthcare providers are in need of an accurate and relatively inexpensive and easily administered test for early predictors of organ failure. In one example, a quick test for the prediction of hepatic health is needed. In other examples, a quick, accurate, and relatively inexpensive test for the prediction of liver failure is needed. Because of the nature of cholate as a predictor of hepatic health of a patient such as a patient with a liver condition (e.g., chronic hepatitis C), a method that can alert a healthcare provider that hepatic health is worsening or improving with treatment would be beneficial from a clinical perspective. This information can alert the health care provider that intervention by a therapeutic treatment may be required immediately. The application of such methods is important for patients with a propensity for organ failure such as hepatic failure, for example in chronic hepatitis C patients. In addition, the application of such methods is important for patients undergoing organ transplantation such as liver transplantation. Other situations where these techniques may be useful include kidney, lung, heart and bone marrow transplantations. Any disease that might alter the hepatic condition could be an indication for use of the test.

Methods for determination of cholate clearance in a patient are disclosed herein. A relatively cheap, quick and reliable assay will promote optimal application of a health provider's resources to diagnose organ insufficiencies such as hepatic insufficiencies and other conditions of altered hepatic function. Alternatively, a quick and reliable assay such as methods for detection of cholate clearance in a sample may be used to monitor response to drug regimen and assess treatment efficiency, leading to a decreased loss of life and decreased cost. These methods may be used to assess the efficiency of one therapeutic treatment versus another or comparing various dose levels of the similar or different treatments on a patient suffering from a hepatic condition.

Advantages of the cholate shunt assay include reliable results that correlate with organ health (e.g., liver health) and use of a naturally occurring substance rather than a drug in a variety of subjects bearing or predisposed to an organ condition. Because the assay utilizes accurate and specific detection methods, the reproducibility and reliability of the test will provide accurate sample analysis. The equipment and methodologies used to analyze the presence of cholate may require chromatography (for example, gas chromatography (GC) or high pressure liquid chromatography (HPLC)) and mass spectrometry (MS) with appropriate training of the operator. However, the assay does not require any unusual or complex techniques outside the general spectrum of assays utilizing GC/MS or HPLC/MS technology. The assay is straightforward since the introduced cholate is distinguishable. The assay is sensitive and requires a short time period, typically in the time range of 90 minutes or less. Since the cholate shunt assay can be used to measure cholate clearance early in disease progression and may be combined with other assays, it provides more complete data than presently used methods for early intervention and treatment of hepatic conditions.

The evaluation of the presence of distinguishable cholate in the context of other parameters has suggested that the cholate shunt assay is sensitive to altered states of organ health, including liver in critically ill patients.

Because of the vital importance of earlier targeting of therapies in a shorter amount of time, many markers have been explored for early diagnosis of hepatic disease or condition. An assay requiring 3 hours or longer causes increased discomfort to a subject undergoing such a test.

The cholate shunt assay may be utilized to assess liver function in a patient. In some embodiments, cholate shunt assay results may be analyzed in an individual having or predisposed to a liver condition. Non-limiting examples of liver conditions include but are not limited to cirrhosis, splenomegly, varices, cancer and chronic hepatitis C infection.

In another embodiment, cholate shunt assay results may be analyzed in an individual undergoing an organ transplant. Non-limiting examples of organ transplants include but are not limited to liver transplant rejection, delayed function of the liver transplant, recurrent disease in the transplanted graft, and liver injury.

In yet another embodiment, the cholate shunt assay may be used to analyze healthy subjects to assess organ health in steady state and in times of altered (pathologic or physiologic) conditions, including the special physiologic states of organ transplant.

Evaluation and monitoring of the clearance of cholate may be used to assess liver function in a patient. Whether or not organ (or cellular) destruction can be minimized after events such as organ injury or prolonged exposure to an infection (e.g., Hepatitis C) may depend, in part, upon the early introduction of therapeutically relevant treatments. In order to eliminate, minimize or attenuate such destruction in an individual who has undergone or is undergoing organ damage, failure or similar event, it would be helpful to predict these events earlier in progression rather than later. By comparing the individual's specific level of clearance of cholate to a normal healthy control, or within a given individual over time, a treating physician might determine whether the subject needs to be treated immediately or otherwise observed for a period of time.

Under conditions when cholate clearance is detectably altered in a sample of a subject, such as after organ injury, organ transplant or prolonged infection, it becomes critical that the treating healthcare provider has reliable information available about an individual's concentration of cholate in the sample. For example, a relatively high concentration of the orally administered cholate in the blood is especially likely to occur when the subject is undergoing a delayed liver transplant graft function. In addition, a relatively high concentration of orally administered cholate in the blood is especially likely to occur when a subject with a liver condition (e.g., Hepatitis C) has experienced hepatic insult. Thus, when a patient's organ activity such as hepatic activity is impaired as indicated in the examples above, a healthcare professional may intervene and administer a therapeutic treatment to attenuate the condition or possibly reverse failure of the organ. These interventions may avoid permanent damage or death of the patient. In addition, a healthcare professional may monitor the therapeutic treatment of the subject by obtaining samples from the patient after treatment and analyzing the presence of cholate in the sample and assessing the condition of the patient based on these findings. Therapeutic treatments may be altered depending on the change in cholate detection or concentration of cholate present in the sample.

Healthcare professionals have been hindered by an inability to prescribe individualized doses of agents tailored to the unique physiological responses of a particular subject early enough in the process of organ failure. In the absence of such data, most treatments are introduced to a patient too late. Early diagnosis and intervention with a treatment such as introduction of fluids, sodium bicarbonate, atrial natriuretic peptides, growth factors, dialysis, or any therapy for prevention of organ failure may either attenuate the progression of the condition or alleviate the symptoms of the condition. Thus, a rapid test to assess the onset of organ failure would be extremely useful for diagnosis and therapeutic monitoring.

In one embodiment of the disclosure, hepatic health of a subject may be monitored using either, or both of, the cholate oral clearance assay and the cholate shunt assay to assess hepatic function. In another embodiment either or both of the cholate oral clearance assay or the cholate shunt assay may be used in combination with one or more other QLFTs disclosed herein to assess hepatic function. In accordance with these embodiments, therapeutic intervention may be administered to the subject as necessary. In another embodiment, hepatic health of a subject undergoing therapeutic intervention may be assessed using either, or both of, the cholate oral clearance assay and the cholate shunt assay to assess hepatic function.

In one embodiment, a cholate clearance assay or cholate shunt assay may be used in combination with one or more other hepatic assessment tests. Example protocols for additional quantitative testing include, but are not limited to, additional tests discussed below.

In one embodiment, for example, participants can undergo quantitative assessment of hepatic functional reserve at baseline, with follow-up at 2 and 4 years of the maintenance treatment protocol. At each time point, quantitative testing can be performed after 3 days of a caffeine-free diet and an overnight fast. Patients can report to their respective treatment centers and be admitted to the respective clinical research center. An indwelling catheter will be placed in an antecubital vein and baseline blood drawn. In one aspect, test compounds can be administered both orally (e.g., $^2$H4-cholate, caffeine, antipyrine) and intravenously (e.g., $^{13}$C-cholate, galactose, lidocaine). In another aspect, test compounds can be administered orally only (e.g., $^2$H4-cholate).

Intravenous $^{13}$C-cholate, 20 mg, is dissolved in $NaHCO_3$ solution, passed through a micropore filter, and placed in sterile, capped glass vials prior to use. This preparation can be mixed with 5 ml of 25% human albumin solution just prior to intravenous injection. In one example, blood samples for measurement of cholate isotopes can be obtained at baseline and 5, 10, 15, 20, 30, 45, 60, 75, 90, 105, 120, 150, and less than 180 minutes post-dose (14 samples, 7 ml red top tubes). In another exemplary method, blood samples for measurement of cholate isotopes can be obtained at 5, 20, 45, 60, and 90 minutes post-dose (5 samples).

In one example, a Galactose 30% solution, 100 ml, is given intravenously over 5 minutes. Blood is obtained at 20, 40, 60, and 80 minutes post-dose (7 ml gray top tubes). Samples must be kept on ice or refrigerated. Spin samples for 10 min at 3000 rpm, remove plasma and keep at −20° C. until analysis. "High-dose" samples are diluted 1:2 in Milli-Q water before testing.

The standard test dose for intravenous infusion of lidocaine in the MEGX (monoethylglycine zylidide) assay is 1 mg/kg over 2 minutes. However a recent report suggested that a lower dose (less than 1 mg/kg such as 0.5 mg/kg) may be better tolerated, associated with fewer side effects (30 vs. 53%, sensory symptoms), and gives similar accuracy in quantitating hepatic function. In this experimental example 0.5 mg/kg dose will be used. Blood is obtained at baseline and 15 minutes post-infusion. Results are reported as the difference between the concentrations of MEGX at 15 minutes post-lidocaine, compared to concentration at baseline.

In one exemplary method, saliva samples, for measurement of antipyrine and caffeine, will be obtained at baseline and at 6, 12, 24, 36, 48, and 60 hours post-dosing (7 samples, 5 mls each).

Other quantitative tests include Antipyrine and Standard Caffeine Test (saliva). In one exemplary method, salivary samples are centrifuged to remove particulates, dispensed into 1 ml aliquots for analysis, and internal standard (phenacetin) added. After extraction with organic solvent, samples can be quantitated using HPLC (for example, with a WISP system). Kinetic parameters ($k_{elim}$, Vd, Cl) can be calculated from the plot of salivary concentration vs. time. Concentrations of antipyrine in saliva are equivalent to that found in plasma and all kinetic parameters for antipyrine can be determined from saliva. Kelim is equivalent from saliva and plasma. In contrast, albumin binding of caffeine reduces the diffusion of caffeine into saliva and caffeine concentrations are, therefore, lower in saliva. This effect can lead to falsely high $V_d$ and apparent clearances for salivary caffeine when compared to the same parameters determined from serum samples. New and improved methods for assessing caffeine clearance might be beneficial. $K_{elim}$ from the caffeine data and $k_{elim}$, $V_d$, and Cl from the antipyrine data can also be used.

In one embodiment, the hepatic condition of a subject may be assessed using a test which utilizes an agent labeled by two or more different distinguishable agents, for example, to assess liver metabolism. These distinguishable agents may be introduced to a subject at different times and different dosages and metabolically tracked in the subject. In accordance with this embodiment, the distinguishable agents may include different distinguishable isotopes (e.g. stable isotopes: $^{13}C$, $^{2}H$, $^{15}N$, $^{18}O$ or radioactive isotopes $^{14}C$, $^{3}H$) linked to for example, an agent readily metabolized by the liver such as caffeine. Distinguishable caffeine can be purchased (for example CDN Isotopes Inc., Quebec, CA). This test is referred to as a multi-isotope caffeine metabolism test. To assess hepatic condition in a subject, distinguishable caffeine may be introduced orally and/or by IV and introduced to a subject over a period of time. After introduction to the subject, distinguishable caffeine metabolites are tracked by assessing saliva and/or blood samples. In one embodiment, hepatic condition of a subject may be assessed using 3 different isotopically distinguishable caffeine solution (triple isotope method: TIME) introduced to a patient and sometime later obtaining saliva and/or blood samples where metabolism of the solution is indicative of the subject's hepatic condition. It is contemplated that the time of administration of the distinguishable agent may vary from as short as a few hours to as many as 36 hours before a sample is obtained and metabolism assessed. In one particular embodiment, each distinguishable caffeine solution may be introduced to a subject at a different time and one saliva or one blood sample obtained from the subject sometime after administration of all caffeine solutions to the subject.

In another embodiment, hepatic condition of a subject may be assessed using a test including caffeine labeled by two or more distinguishable agents, introduced to a subject and metabolically tracked in the subject in combination with another hepatic assessment test such as a hepatic blood flow test. For example the multi-isotope caffeine metabolism test (e.g. triple isotope method) may be combined with a cholate clearance or cholate shunt assay disclosed herein. Other tests may be combined with the multi-isotope caffeine metabolism test such as other metabolism or hepatic blood flow tests that reflect hepatic condition. Outcomes of these tests are indicative of hepatic condition and thus assessment of current or future need of treatment to alleviate any hepatic condition in a subject may be recognized. In addition, any methods disclosed herein may be used to assess hepatic condition in a subject undergoing a treatment for a condition. If required, a treatment of such as subject may be modified in accordance with the hepatic condition.

In the present invention, one advantage of using a multi-isotope caffeine test is that dietary caffeine will not interfere with the assay. In addition the data obtained from elimination of caffeine from an individual is near total elimination of the caffeine. The sampling post administration of the distinguishable solution may be a single time point.

Unlike the typical clearance, metabolism, or breath test analyses of caffeine, caffeine tests disclosed herein avoid caffeine interference by diet or drug caffeine. In addition, caffeine tests of the present invention assess a more global assessment of caffeine metabolism compared to traditional caffeine breath tests that assess a single pathway.

In one embodiment, the predictive value of the quantitative tests can be established as follows. The results of the baseline studies can be characterized by one or more of a mean, median, distribution, and confidence intervals (CIs) for one or more of the measures of hepatic function (caffeine $k_{elim}$, antipyrine $k_{elim}$, antipyrine Vd, antipyrine clearance, galactose elimination capacity, MEGX15 min, cholate $k_{elim}$ iv, cholate Vd iv, cholate Cliv, cholate Clpo, cholate SF, and perfused hepatic mass). The median value for each test may be used to divide the patient sample into two groups for analysis of the ability of the test to predict clinical progression. The composition of the groups will change for each test analyzed based upon the baseline results for the specific test undergoing evaluation. For example, the median value for caffeine $k_{elim}$ may be 0.04 $h^{-1}$. Values below 0.04 $h^{-1}$ indicate poorer function and greater likelihood for early clinical decompensation. In one aspect, the median value for cholate SF is 30%; values above 30% indicate poorer first-pass clearance and greater likelihood for early decompensation. For example, Patient A tests may indicate caffeine $k_{elim}$ 0.06 $h^{-1}$ and cholate SF 55%. In the analysis of the predictive value of these tests, Patient A's long-term outcome would be analyzed with the caffeine group likely to have a better outcome but with the cholate group likely to have a poorer outcome. Predictive value is calculated by standard technique using 2×2 tables that define true positives (TP) and negatives (TN) and false positives (FP) and negatives (FN). A hypothetical analysis is shown in Table 1 for the example of results from cholate SF testing.

TABLE 1

Predictive value of cholate shunt fraction in hepatic disease progression.

| Disease Progression | Cholate SF >30% | Cholate SF <30% |
|---|---|---|
| Yes | TP | FN |
| No | FP | TN |

Positive Predictive Value = TP/[TP + FP] × 100%
Negative Predictive Value = TN/[TN + FN] × 100%

The predictive value of the various tests may be compared and interaction between the quantitative tests in predicting outcome will be performed by multivariate analysis of the continuous independent variables (quantitative tests) against the binomial dependent variable (development or absence of clinical decompensation).

In one embodiment, the quantitative tests can be used to determine an outcome or endpoint of therapy. The control group of a given study may experience progressive decline in hepatic function as measured by quantitative tests. Each patient may serve as his own control; test results in years 2 and 4 of treatment will be subtracted from baseline test values.

The absolute and percent change from baseline will be determined for each patient at each time point and mean, median, distribution, and confidence intervals determined. Statistical significance of differences in the changes from baseline between treatment and control groups may be determined by ANOVA. In addition, changes in quantitative tests will also be compared to changes in fibrosis scores, fibrosis morphometry, standard biochemical tests, and concentrations of HCV RNA. Kaplan-Meier curves and Log-Rank tests (nonparametric) will also be used to compare the changes in quantitative tests between the two patient groups.

Other tests may be utilized for combination analysis such as, for example, sulfur colloid distribution parameters. In one exemplary method, the cholate shunt or cholate clearance assay may be combined with analysis of sulfur colloid distribution. The distribution of sulfur colloid from the planer scan can be assessed by any means known in the art. In another example, distribution of sulfur colloid between liver and bone marrow may be assessed by any means known in the art and used in combination with any assay disclosed herein.

In one embodiment, distinguishable compounds, agents or solutions used herein include compounds that are traceable or trackable. These compounds linked to an agent of interest (e.g., cholate or caffeine) may be followed as they are processed or passed through a subject before, during and/or after administration of the distinguishable agent to the subject. Cholates used in any one of these assays might be labeled with either stable ($^{13}C$, $^{2}H$, $^{18}O$) or radioactive ($^{14}C$, $^{3}H$) isotopes. These same isotopes and potentially $^{15}N$ or Tc-99m could be linked to any of the other agents described and referenced herein. A number of other test compounds are listed in the descriptions above and could be used as potential substitutes for either cholate (other bile acids, propranolol, lidocaine, nitroglycerin) or caffeine (antipyrine, erythromycin, lidocaine-MEGX, midazolam, dextromethorphan, and any other xenobiotic or compound metabolized by the P450 system).

A radionuclide may be bound to an agent such as cholate either directly or indirectly by using for example an intermediary functional group. Intermediary functional groups which may be used to bind radioisotopes which exist as metallic ions to antibody are diethylenetriaminepentaacetic acid (DTPA) and ethylene diaminetetracetic acid (EDTA). Examples of metallic ions suitable for use in this invention are 99 mTc, $^{123}I$, $^{131}I$ $^{111}In$, $^{131}I$, $^{97}Ru$, $^{67}cu$, $^{67}Ga$, $^{125}I$, $^{68}Ga$, $^{72}As$, $^{89}Zr$, and $^{201}Tl$.

In accordance with these embodiments, agent(s) thereof may be labeled by any of several techniques known to the art. The methods of the present invention may also use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Other labeled compounds are contemplated such as fluorescent compounds. As known in the art any distinguishable component may be covalently linked or attached in any manner to the agent for detection in a sample such as fluorescent dye etc.

After hepatic condition of a subject has been assessed by one or more of the QLFTs disclosed herein, it may be determined that a therapeutic treatment is necessary for the subject. Likely treatments or interventions in hepatic conditions include but are not limited to an interferon, e.g., interferon alpha-2b, peginterferon; ribavirin; a combination of an interferon and ribavirin; any new and emerging treatments for either or both hepatitis B and C; lamivudine, adefovir; tenofovir; telbivudine; telaprevir; boceprevir; ursodeoxycholic acid; treatments for NASH, TIPS; hepatic resection; and hepatic transplantation.

In one aspect, one or more of the QLFTs disclosed herein may be used to monitor treatment and/or disease progression.

In still further embodiments, the present invention discloses kits for use with the methods and comparison methods described herein. One or more distinguishable agent(s) provided in a kit may be employed to assess organ health in a health facility and/or a home kit format. Distinguishable agent(s) such as a hepatic blood flow assessing agent and/or hepatic metabolism assessing agent (e.g. cholate and/or caffeine, respectively) may thus comprise, a suitable container means, an oral dose of distinguishable agent to possibly be administered outside of a hospital environment. In addition, a second IV dose may be administered in a healthcare facility. Sample tubes for collection of the bodily fluid samples such as blood or saliva for collection either inside or outside a healthcare facility may also be included. In one example, a kit may comprise an oral and an IV dose of one or more distinguishable agents and sample tubes for collection of samples over a period of less than 3 hours after administration of the distinguishable agents. In another example, a kit may comprise an oral dose of one or more distinguishable agents and sample tubes for collection of samples over a period of less than 3 hours, after administration of the distinguishable agents. In another example, a kit may comprise components necessary for a test period of 90 minutes post administration of one or more distinguishable agents. In a further example, a kit may comprise components necessary for a test period of 30 minutes post administration of distinguishable agents.

Another kit may include distinguishable metabolic indicators of hepatic health such as distinguishable caffeine. It is also contemplated that a combination kit having both a metabolic indicator such as caffeine and a hepatic blood flow indicator such as cholate may be useful to assess overall hepatic health of a subject.

Further suitable reagents for use in the present kits include the two-component reagent that comprises a distinguishable agent detection system and a metabolic function detection system. The kits may further comprise a suitably aliquoted composition of the specific agent such as cholate, whether labeled or unlabeled, as may be used to prepare a standard curve for a detection assay.

The container means of the kits will generally include at least one vial, test tube, flask, bottle, syringe or other container means, into which the distinguishable agent may be placed, and preferably, suitably aliquoted. The kits of the present invention will also typically include a means for containing the distinguishable agent and any other reagent containers in close confinement for commercial sale. Such containers may include injection or blow-molded plastic containers into which the desired vials are retained. In addition, the kits may contain a product for diluting the distinguishable oral agent such as a fruit juice or other liquid.

In certain embodiments, determination of oral cholate clearance, without simultaneous determination of intravenously administered cholate clearance, is disclosed. Unique uses of oral cholate clearance include situations where avoidance of an intravenous dose of isotopically labeled cholate is desirable; such as in, for example, pediatric populations. Use of the oral cholate clearance test (cholate clearance po) is a robust predictor of clinical outcome, as shown in Example 13.

Clearance of orally administered labeled cholate and cholate shunt can be useful in monitoring patients with liver disease. Certain embodiments pertain to specific clinical applications of the oral cholate clearance (Cholate $Cl_{oral}$;

Cholate Clearance po; HepQuant-Oral) and/or cholate shunt (HepQuant-Dual) tests wherein results are correlated with disease severity.

In certain aspects, the methods of the disclosure, for example, oral cholate clearance and the cholate shunt, can be used for selection of patients with significant fibrosis, and cirrhosis; selection of patients for endoscopy who are likely to have varices; selection of patients for endoscopy with large varices (varices at risk to bleed); identification of patients with chronic hepatitis C who are unable to respond to peginterferon/ribaviron; tracking hepatic improvement in patients who respond to therapy; and identifying the subgroup of patients who are likely to experience future decompensation. Clinically relevant values for various conditions are shown in Table 2.

In further aspects, it is contemplated that the methods of the disclosure, including oral cholate clearance and cholate shunt, can be utilized for a number of clinical applications, for example, selection of patients with chronic hepatitis B who should receive antiviral therapy; assessing the risk of hepatic decompensation in patients with hepatocellular carcinoma (HCC) being evaluated for hepatic resection; identifying a subgroup of patients on waiting list with low MELD (Model for End-stage Liver Disease score) who are at-risk for dying while waiting for an organ donor; as an endpoint in clinical trials; replacing liver biopsy in pediatric populations; tracking of allograft function; measuring return of function in living donors; and measuring functional impairment in cholestatic liver disease (PSC, Primary Sclerosing Cholangitis).

TABLE 2

Clinical Applications for Oral Cholate Clearance and Cholate Shunt.

| Clinical Application | HepQuant-Oral | Stat Test, Score, and P value | HepQuant-Dual | Stat Test, Score, and P value | Reference |
|---|---|---|---|---|---|
| Selection of patients with significant fibrosis | Cl < 1250 mL/min, at this value of Cl the calculated Ishak fibrosis score from the regression equation was 2.6 | regression analysis, r = −0.52, P < 0.001 | Shunt > 30%, at this value of shunt the calculated Ishak fibrosis score from the regression equation was 2.6 | regression analysis, r = 0.49, P < 0.001 | Aliment Pharmacol Ther 2008; 27: 798-809 |
| Selection of patients with cirrhosis | PPV of Cl < 1250 mL/min: 53% PPV of Cl < 750 mL/min: 69% | ROC analysis, c-stat, P < 0.0001 | PPV of Shunt > 30%: 51% PPV of Shunt > 50%: 72% | ROC analysis, c-stat, P < 0.0001 | Aliment Pharmacol Ther 2008: 27: 798-809 |
| Selecting patients for endoscopy who are likely to have varices | PPV of Cl < 1250 mL/min: 43% PPV of Cl < 750 mL/min: 58% | ROC analysis, c-stat, P < 0.0001 | PPV of Shunt > 30%: 41% PPV of Shunt > 50%: 57% | ROC analysis, c-stat, P < 0.0001 | Aliment Pharmacol Ther 2008; 27: 798-809. |
| Selecting patients for endoscopy who are likely to have large varices (varices at-risk to bleed) | 100% had Cl < 1250 mL/min 91% had Cl < 750 mL/min | Sensitivity analysis | 100% had Shunt > 30% 91% had shunt > 35% | Sensitivity analsysis | Aliment Pharmacol Ther 2007; 26: 401-410. |
| Identifying patients with chronic hepatitis C who are unable to respond to peginterferon/ribavirin | Cl < 771 mL/min, below this value of Cl only 2% of patients achieved SVR | Quartile analysis | Shunt > 48%, above this value of shunt only 2% of patients achieved SVR | Quartile analysis | Aliment Pharmacol Ther 2009; 29: 589-601. |
| Tracking hepatic improvement in patients who respond to therapy | Improved by 32% with SVR and worsened by 10% in nonresponders | Paired analysis, P < 0.0001 | Improved by 25% with SVR and no change in nonresponders | Paired analysis, P = 0.003 | Aliment Pharmacol Ther 2009; 29: 589-601. |
| Identifying the subgroup of patients who are likely to experience future decompensation | Outcomes by tertiles: Cl < 9.5 mL/min - 47% of these patients had outcomes; 9.5 < Cl < 14.5-9% of these patients had outcomes; Cl > 14.5-5% of these patients had outcomes. By ROC, using cutoff Cl = 11 mL/kg/min: 41.5% with Cl < 11 had outcomes compared to only 6.9% in those with Cl > 11 | Kaplan-Meier And ROC analysis, all P values < 0.0001. Hazard ratio for interquartile increase in risk of outcome was 4.37 in univariate and 3.23 in trivariate analysis (included covariates of biopsy cirrhosis and platelet count) | Outcomes by tertiles: Shunt > 45%-42% of these patients had outcomes; 45% > Shunt > 32%-14% of these patients had outcomes; Shunt < 32%-5% of these patients had outcomes. By ROC, using cutoff Shunt = 39%: 38.8% with shunt > 39% had outcomes compared to only 6.6% in those with Shunt<39% | Kaplan-Meier And ROC analysis, all P values < 0.0001. Hazard ratio for interquartile increase in risk of outcome was 3.26 in univariate and 2.35 in trivariate analysis (included covariates of biopsy cirrhosis and platelet count) | Hepatology October Issue Accepted for presentation at AASLD 2009 |

Figure 12:
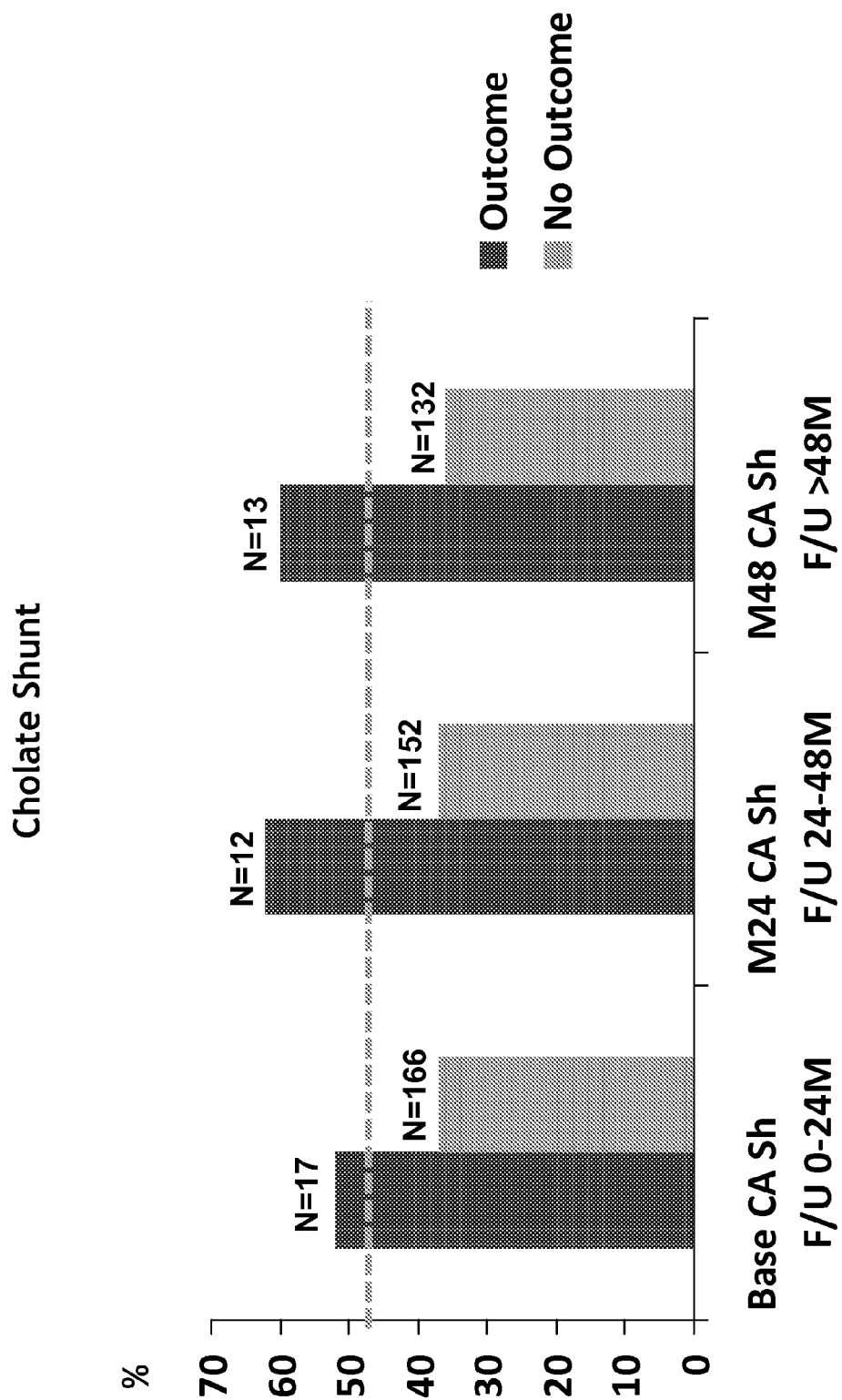
FIG. 12 shows the cutoff for cholate shunt that predicts the 2-year risk of decompensation in hepatitis C patients.
Figure 14:
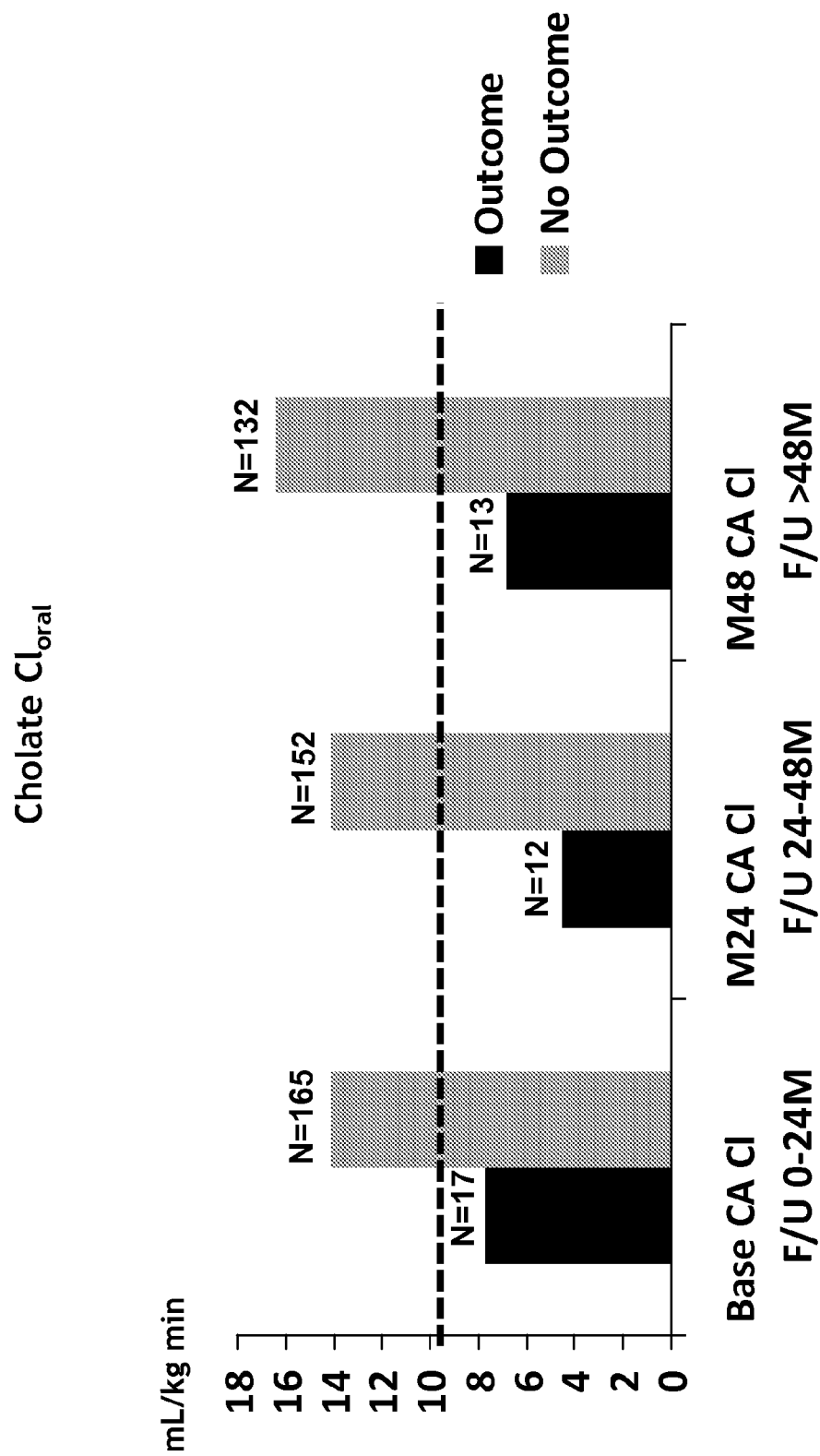
FIG. 14 shows the cutoff for oral cholate clearance that predicts the 2-year risk of decompensation.

In a specific aspect, oral cholate clearance or cholate shunt assays can be used repeatedly over time as a predictor of clinical outcome as shown in FIGS. 12 and 14.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following examples are included to demonstrate preferred embodiments.

Example 1

Procedure for Performance of Multiple Quantitative Liver Function Tests (QLFTs)

Supplies
IV Test Compounds:
IV Solution B—30% Galactose (e.g. Pfanstiehl Laboratories).
IV Solution C—$^{13}$C-Cholate (20 mg) (e.g. CDN Isotopes).
IV Test Compound supplied ready to use in Test Kit.
IV Solution A—2% Lidocaine (e.g. Abbott Laboratories).
PO (Per Oral) Test Compounds:
$^2$H4-Cholate (40 mg) (e.g. CDN Isotopes).
Caffeine (300 mg) (e.g. Ruger)Antipyrine (500 mg) (e.g. Ruger).
Sodium bicarbonate (e.g. 600 mg).
Patient Testing Supplies:
25% Human Albumin for injection (5 mls) to be added to $^{13}$C-Cholate solution.
Serum/plasma transfer tubes and labels.
Saliva collection tubes and labels.
IV supplies, including 250 mls NS, indwelling catheter, 3-way stopcock.
3 cc, 5 cc, 10 cc, and 50 cc syringes for administering IV test compounds and drawing blood samples.
7 cc red top and 7 cc gray top vacutainer tubes for serum sample collections.
Needle discard bucket.
A drinking substance such as apple or grape juice for diluting oral test compounds.
One standard caffeine-free meal with one can Ensure® for Liver-Spleen Scan.
Example Patient Preparation
Ascertain whether patient has history of allergic reactions to local anesthetics (such as at the dentist), or history of cardiac arrhythmias; if so, do not administer lidocaine. Patient is caffeine-free for 72 hours prior to test day and for the subsequent 3 days of saliva collections. Patient is NPO except water after MN the night before test day. Patient has IV with 3-way stopcock and NS TKO placed before test begins.
Exemplary Test Compound Preparation
One exemplary solution of an oral composition may contain 2H4-Cholate, Caffeine, Antipyrine, and Sodium bicarbonate (e.g. 40 mg. 300 mg, 500 and 600 mg respectively). In one exemplary method, the day before the test, water can be added to about the 10 cc mark on a tube containing the oral test compounds to obtain the Oral Test Solution. Cap tube tightly and shake to mix. Swirl contents to get all the powder granules down into the water.

On the test day pour dissolved Oral Test Solution into a container such as a urine cup. Rinse tube into urine cup with about 10 mls water. Prior to beginning the test, add a diluting liquid such as grape or apple juice (not citrus juice) to about the 40 ml mark on the urine cup containing the Oral Test Solution. Swirl gently to mix; do not shake or stir, or mixture may foam out of container. Have extra juice on hand for rinse.
Preparation of IV Solutions
IV Solution A (2% Lidocaine). 2% Lidocaine in a prepackaged single-use 5 cc syringe as part of the Test Kit may be provided. Test dose is 0.5 mg Lidocaine/kg. Calculate appropriate dose of Lidocaine. Divide the patient's weight in pounds by 2.2 to get kilograms; i.e., 150 lbs/2.2=68.2 kg. Multiply the weight in kg by 0.5 mg/kg to get the Lidocaine dose; i.e., 68.2 kg.times.0.5=34.3 mg. Divide the desired mg by 20 (concentration of 2% Lidocaine in mg/ml) to get cc's; i.e., 34.3 mg/20=1.71 cc. Expel excess Lidocaine from the 5 cc syringe so that it contains the correct dose.

IV Solution B (100 cc 30% Galactose). Galactose is prepared in individual doses for IV. A preparation procedure may be provided. Test dose is 30 gm Galactose, or 100 mls of 30% Galactose solution.

IV Solution C (20 mg $^{13}$C-Cholate in 5 cc 1 mEq/ml Sodium Bicarbonate+5 cc 25% Human Albumin). $^{13}$C-Cholate can be prepared in individual 5 cc doses for IV. A preparation procedure may be provided. Test dose is 20 mg $^{13}$C-Cholate (in 10 cc diluent). If vial is frozen, allow to thaw completely before continuing. Just prior to beginning test, mix $^{13}$C-Cholate solution with albumin as follows (this method prevents loss of test compound during mixing process). Draw up all of $^{13}$C-Cholate solution (about 5 cc) in a 10 cc syringe. Draw up 5 cc albumin in another 10 cc syringe. Inject this gently (to prevent foaming) into empty $^{13}$C-Cholate vial, invert vial to rinse, then withdraw all of the albumin back into same syringe. This rinses all of the $^{13}$C-Cholate out of the vial. Detach needle from the $^{13}$C-Cholate syringe and attach a 3-way stopcock. Detach needle from albumin syringe and inject albumin through stopcock into $^{13}$C-Cholate syringe. Draw a little air into bile acid/albumin syringe and mix solutions gently by inverting syringe several times. Expel air.
Testing Procedure
In one exemplary method the following procedure will be used. Collect baseline saliva and serum samples (see Sample Collection) before test compounds are administered.
Administration of Test Compounds.
Start timer. Record 24-hour clock time as T=0.0 to 2 minutes—using 3-way stopcock, administer IV Solution A (1 mg/kg 2% Lidocaine) IV push. Record timer time-2 to 3 minutes-allow NS to flush line for 1 minute-3 to 8 minutes-using 3-way stopcock. Administer IV Solution B (100 ml bolus 30% Galactose) IV push. Record timer time-8 to 9 minutes-allow NS to flush line for 1 minute-8 to 9 minutes. While line is flushing, have patient drink oral solution of test compounds and juice. Rinse cup with a little more juice and have patient drink rinse-9 to 10 minutes. Using 3-way stopcock, administer IV Solution C (20 mg Bile Acid in 5 mls 1 mEq/ml Sodium Bicarbonate+5 mls 25% Human Albumin) IV push. Record timer time.
Sample Collection
Blood
$^{13}$C-Cholate Clearance (IV Solution C). Collect all samples via the 3-way stopcock with 0.5 ml discard before each sample to prevent dilution or cross-contamination of samples. Collect 7 ml at each time point in colored tubes such as red tops for $^{13}$C-Cholate Clearance (IV Solution C) at the following times (time after administration/timer time): baseline (before test compounds administered), 5/15, 10/20, 15/25, 20/30, 30/40, 45/55, 60/70, 75/85, 90/100, 105/115, 120/130, 150/160, and 180/190 minutes.

Galactose Clearance (IV Solution B). Collect 7 ml in a different colored cap tube like gray tops for Galactose Clearance (IV Solution B) at the following times, also using same timer started at T=0 (time after administration/timer time): baseline (before test compounds administered), 20/28, 40/48, 60/68, and 80/88 minutes.

Lidocaine (IV Solution A). Collect 10 ml red tops for MEGX Concentration (Lidocaine IV Solution A) at the following times (time after administration/timer time): baseline (before test compounds administered), 15/17, and 30/32 minutes. Keep gray top tubes on ice or refrigerated. Allow red tops to clot at room temperature for at least 30 minutes. Spin all samples for 15 minutes. Transfer plasma (gray)/serum (red) to appropriate labeled tubes and freeze at −20° C. until shipping. Ship frozen.

Saliva

Have patient rinse mouth with water before each sample collection, then stimulate saliva production by chewing parafilm squares. Collect 5 cc saliva (foam does not count) by spitting into labeled collection tube. Collect at the following times: baseline, and 6, 12, 24, 36, 48, and 60 hours. Patient may collect samples at home for convenience. If so, instruct patient regarding saliva collections at home, freezing at home, and returning samples to site. Give patient supplies for home collection. Cap tubes tightly and freeze at −20° C. until shipping. Ship frozen.

Liver/Spleen Scan

After completion of the blood sample collections (T=190) and 1 hour before Liver-Spleen Scan, give subject standard, caffeine-free meal.

Example 2

Cholate Shunt (CAshunt) Testing Procedure Utilizing GC/MS Analysis

In one exemplary method, two hundred eighty five patients were enrolled in a clinical trial (called the HALT-C trial; Hepatitis Antiviral Long-Term Treatment to Prevent Cirrhosis Trial) and participated in a QLFT (quantitative liver function test) ancillary study. Seventy three patients were studied twice.

Example Patient Protocol: 20 mg of 24-$^{13}$C cholic acid was dissolved in NaHCO$_3$, mixed with 5 ml 25% human albumin solution and injected through an indwelling intravenous catheter over 2 minutes. 40 mg of 2,2,4,4-$^2$H cholic acid was dissolved in water, mixed in juice and taken orally simultaneously with the intravenous injection. Blood samples were drawn through the indwelling catheter and taken prior to isotope administration and 5, 10, 15, 20, 30, 45, 60, 75, 90, 105, 120, 150 and 180 minutes post-dose to obtain oral and intravenous cholic acid clearance curves.

Sample Preparation Protocol for GC/MS:

In this trial, patient samples were processed using the following protocol. In one example, dispense 0.5 ml patient serum and add 50 ul of cholic acid standard, set aside two cholic acid controls. To each tube add 0.5 ml distilled water and 0.5 ml 0.02 N NaOH. Mix and incubate in a 60-degree water bath for 30 minutes. Prepare Bond Elute paks (C18-OH) by washing with 5 mls methanol and 10 mls water. Add patient sample to pak. Wash paks with 5 mls distilled water, 5 mls 13% methanol and 5 mls 87% methanol. Dry sample completely. Add 1.5 ml water to dried residue, 1 drop HCl and 2 ml of diethyl ether. Vortex for 30 seconds. Centrifuge for 5 minutes to clarify layers. Collect ether layer in small, screw-capped, silanized test tubes. Repeat this step. Evaporate ether in 30-degree water bath under stream of nitrogen. Methylate samples by adding 1 ml methanol, 1 ml DMP and 1 drop HCl and incubate at room temperature in the dark for 30 minutes. Evaporate solvent at 40 degrees in water bath under a stream of nitrogen. Make trimethylsilyl ether derivatives of bile acids by adding 0.2 ml pyridine, 8 drops HMDS (hexamethyldisilazane) and 4 drops TMCS (trimethylchlorosilane) and incubate 55-60 degrees for 2 hours. Evaporate solvents under nitrogen stream. Add 2 ml hexane. Centrifuge for 5 minutes and pour off hexane. Repeat this step. Evaporate solvent and reconstitute with 4 drops hexane. Vortex and sonicate, then transfer to injection vials. Inject onto GC/MS 6890/5973 using method Cholic2.m. This method instructs the mass spectrometer to analyze each sample injection searching for ions associated with derivatized cholate isotopes.

Results

The full range and boundaries for quartiles of results for cholate clearances and shunt in the 282 patients at baseline, prior to entry into the trial, are shown in Table 3. Clearances progressively declined and shunt progressively increased as results ranged from 'best' to 'worst'. Cholate shunts spanned the entire range of expected result, from the low end of the normal range, 10% ('best'), to nearly complete shunting, 91% ('worst').

TABLE 3

Range of study results for cholate clearances and cholate shunt in study patients.

| | Boundaries for quartiles of test results | | | | |
|---|---|---|---|---|---|
| | Best | 25th | 50th | 75th | Worst |
| Cholate Cliv (mL/min) | 903 | 457 | 367 | 305 | 155 |
| Cholate Cloral (mL/min) | 3036 | 1427 | 1087 | 768 | 255 |
| Cholate shunt (%) | 10 | 27 | 36 | 48 | 91 |

Results in 32 healthy controls were (mean+/−s.d., range): $Cl_{iv}$ 390+/−136, 155-873 mL/min; $Cl_{oral}$ 2173+/−677, 1369-3856 mL/min; and shunt 18.5+/−5.5, 8.0-28.5%. The range of HALT-C patients (Table 3) completely overlapped with Cliv for these healthy controls. In contrast, approximately 70% of HALT-C patients exceeded the normal limits for $Cl_{oral}$ of 1300 mL/min and shunt of 30% (Table 3). Consequently, both cholate $Cl_{oral}$ and cholate shunt are useful for defining risk of cirrhosis and varices.

Example 3

Statistical Analysis

In one example, the following analysis was performed to determine if exogenously ingested and iv administered distinguishable agents can be utilized as markers for hepatic conditions; not simply an affirmative or negative test for hepatic conditions.

Example Study

In one example, 7 QLFTs were used to define hepatic impairment in patients with chronic hepatitis C and bridging fibrosis or compensated cirrhosis enrolled in the Hepatitis Antiviral Long-Term Treatment to Prevent Cirrhosis Trial (HALT C). Test results were compared with or without biopsy-proven cirrhosis, splenomegaly on ultrasonography, and varices at endoscopy.

In one example study the mean age of the 248 enrolled patients was 49.9+7.3 yr and 75% were male. Mean BMI (body mass index) was 29.6+5.3, 40% had cirrhosis, 60% had bridging fibrosis, 93% were infected with HCV genotype 1, and mean serum HCV RNA was 4.39+4.66×106 copies/ml. 30% had platelet count <140,000/ul, 25% had albumin <3.5 g/dl, 25% had INR >1.1 (international normalization ratio prothrombin), 10% had bilirubin >1.2 mg/dl, and 25% had AST:ALT >1 (serum aspartate transaminase: serum alanine transaminase).

In accordance with this example: $^{13}$C-methionine (MBT), caffeine (Caf), antipyrine (AP), and 2,2,4,4-$^2$H-cholate (CA) were taken orally and 24-$^{13}$C-cholate, galactose (Gal), and lidocaine were administered intravenously. These compounds or their metabolites were measured from timed serial samples of blood, saliva, and breath using standard techniques. Elimination rate (kelim), volume of distribution (Vd), clearance (Cl), elimination capacity (Elim), and shunt were calculated from measured analytes. Perfused hepatic mass (PHM) was determined from SPECT liver scan. Mean test results were compared by T statistic and area under the receiver operator curve (ROC) by C statistic. Table results are ordered by T statistic for association with cirrhosis. PHM had the highest area under ROC with cirrhosis (C statistic 0.87), splenomegaly (C statistic 0.75), and varices (C statistic 0.832) and correlated best with platelet count, bilirubin, prothrombin time, and albumin.

The outcome of the exemplary process was that QLFTs uncover hepatic impairment in a high proportion of fibrotic patients with chronic hepatitis C. Some of the tests, particularly CA Cloral, PHM, and CAshunt, identify patients with chronic hepatitis C with cirrhosis, splenomegaly or varices.

In one example, long-term follow-up, may be planned in the HALT C trial in order to determine whether hepatic impairment as defined by QLFTs predicts risk for clinical deterioration.

Example 4

Additional Standard Laboratory Tests

Standard laboratory tests (complete blood count, liver biochemistry profile) per routine clinical care of the post-hepatectomy donor can be performed at each center and per the prospective A2ALL Cohort Study donor protocols. In addition, specific study-related tests can be obtained at times of QLFT testing (baseline, 5 to 10 days, 3 months, and 6 months). The latter tests can include: Complete Blood Count; Liver biochemistry profile (6 month only; others are already included in Cohort Study); Body weight; BMI; Medication history (all); and Recording of any clinical events at 6-month time point.

Example 5

Exemplary Computing Device for Data Analysis

FIG. 1 illustrates an exemplary computing device 100 that can carry out the operations described herein in accordance with various embodiments of the present invention. The exemplary computing device 100 is illustrative of many different types of computing devices such as, but not limited to, a general-purpose computer, a special-purpose computer, web server, and a handheld computer. It is to be understood that embodiments of the present invention are not limited to the particular computing device 100 shown in FIG. 1.

In one embodiment, the computing device 100 is in operable communication with a mass spectrometer, which generates chromatographic data. The chromatographic data can then be transmitted to the computing device 100. In another embodiment, the computing device 100 can download chromatographic data from a network resource. In yet another embodiment, chromatographic data can be input to the computer via a memory medium, such as a disk. Still another embodiment allows for the chromatographic data to be manually entered into the computing device 100 (e.g., via keyboard).

In this simplified example, the computing device 100 comprises a bus or other communication means 101 for communicating information, and a processing means such as one or more processors 102 coupled with bus 101 for processing information. Computing device 100 further comprises a random access memory (RAM) or other dynamic storage device 104 (referred to as main memory), coupled to bus 101 for storing information and instructions to be executed by processor(s) 102. Main memory 104 also may be used for storing temporary variables or other intermediate information during execution of instructions by processor(s) 102. Computing device 100 also comprises a read only memory (ROM) and/or other static storage device 106 coupled to bus 101 for storing static information and instructions for processor 102. A data storage device 107 such as a magnetic disk or optical disc and its corresponding drive may also be coupled to bus 101 for storing information and instructions.

One or more communication ports 110 may also be coupled to bus 101 for allowing communication and exchange of information to/from with the computing device 100 by way of a Local Area Network (LAN), Wide Area Network (WAN), Metropolitan Area Network (MAN), the Internet, or the public switched telephone network (PSTN), for example. The communication ports 110 may include various combinations of well-known interfaces, such as one or more modems to provide dial up capability, one or more 10/100 Ethernet ports, one or more Gigabit Ethernet ports (fiber and/or copper), or other well-known interfaces, such as Asynchronous Transfer Mode (ATM) ports and other interfaces commonly used in existing LAN, WAN, MAN network environments. In any event, in this manner, the computing device 100 may be coupled to a number of other network devices, clients and/or servers via a conventional network infrastructure, such as a company's Intranet and/or the Internet, for example.

Exemplary Operations for Data Analysis

Figure 4:
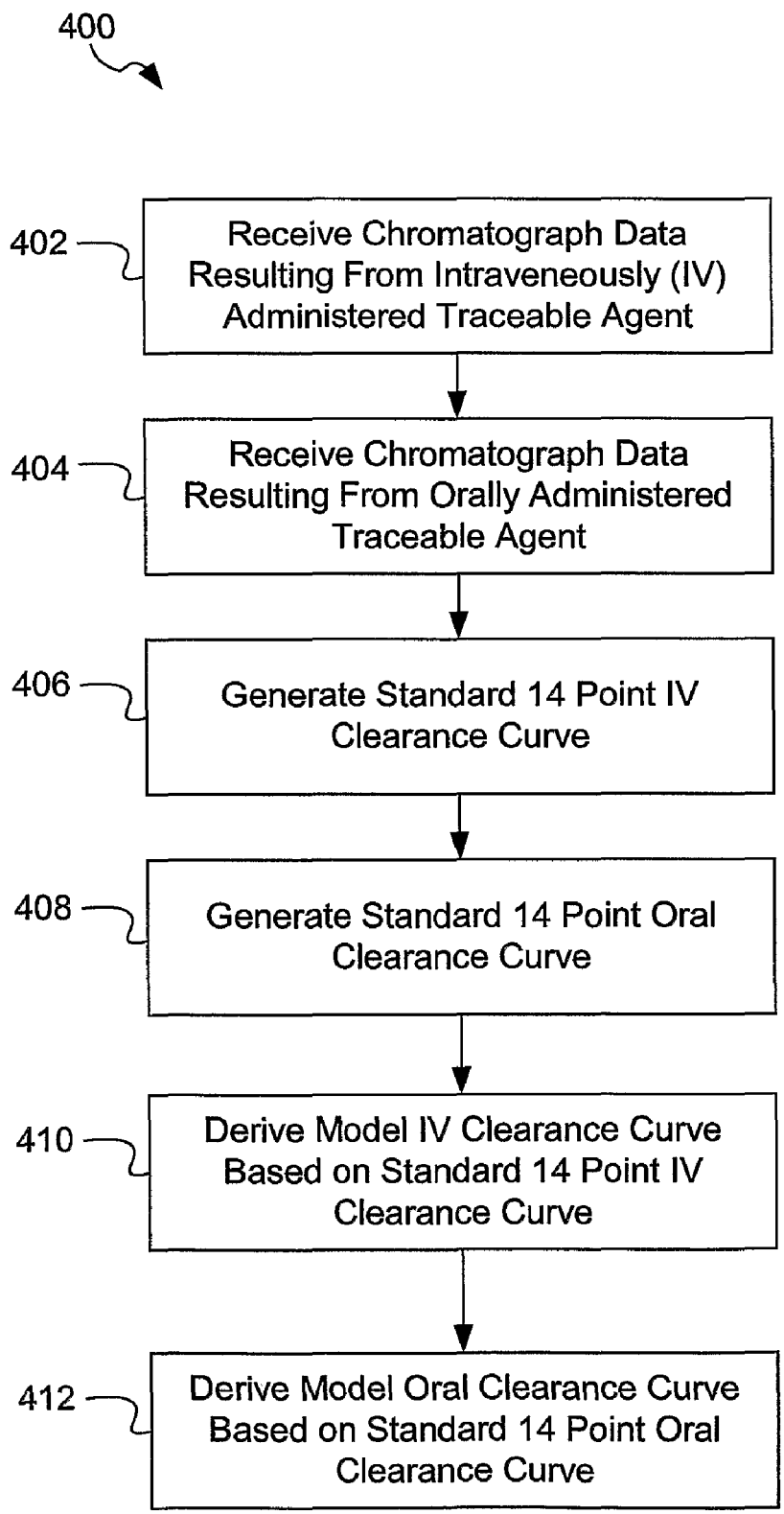
FIG. 4 illustrates a flow chart of an exemplary model curve derivation algorithm 400 having exemplary operations for generating a model clearance curve in accordance with one embodiment of the present invention.

FIG. 4 illustrates an exemplary model curve derivation algorithm 400 having exemplary operations for deriving a model clearance curve in accordance with a particular embodiment of the present invention. The algorithm 400 can be carried out by the computing device 100 shown in FIG. 1. Alternatively, the algorithm 400 could be carried out by a device other than the computing device 100. Prior to describing the algorithm 400 in detail, some general aspects of distinguishable agents and clearance of agents from blood for example are discussed.

Figure 2:
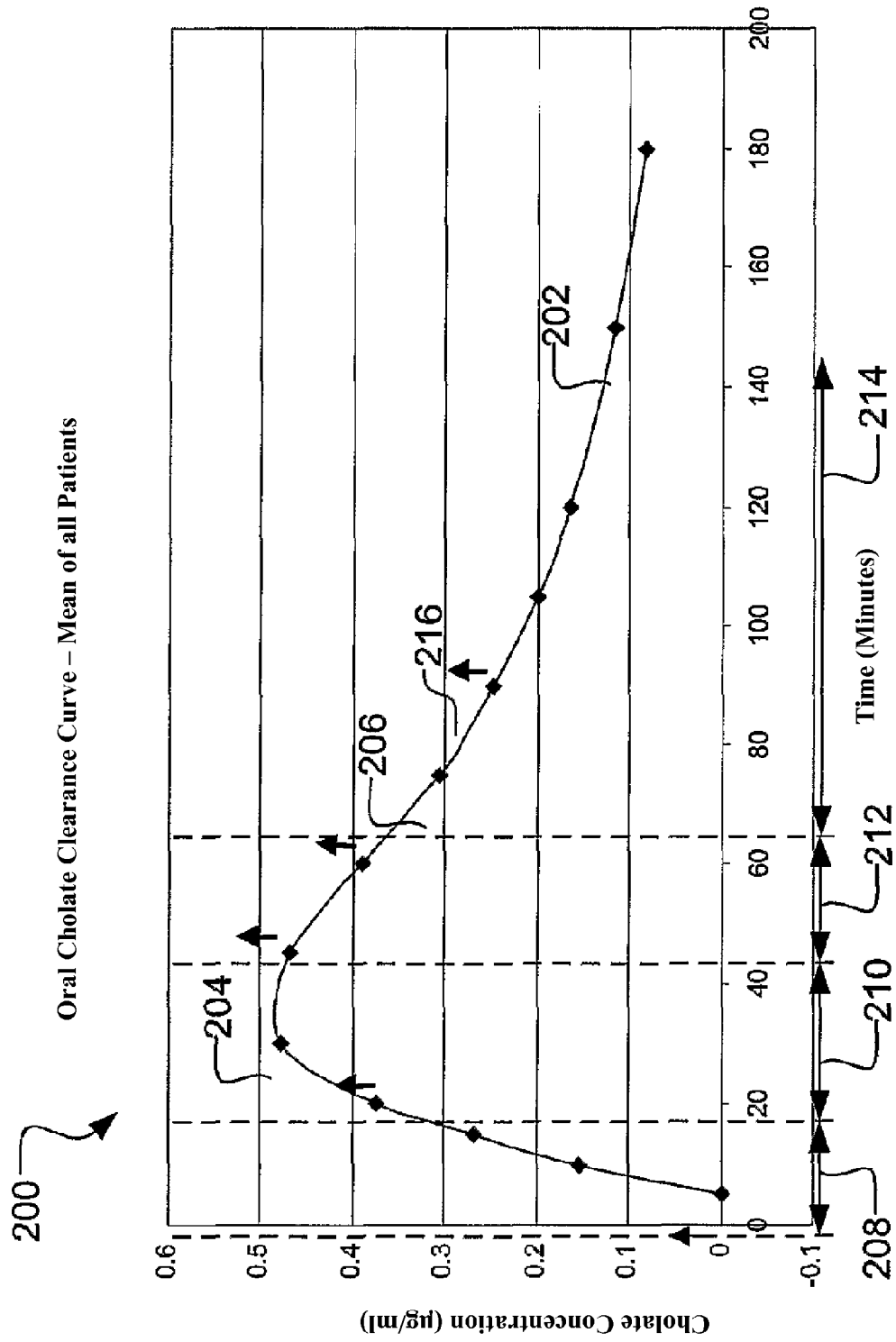
FIG. 2 illustrates an cholate oral clearance curve derived from an average sampling of over 300 patients administered cholate orally.
Figure 3:
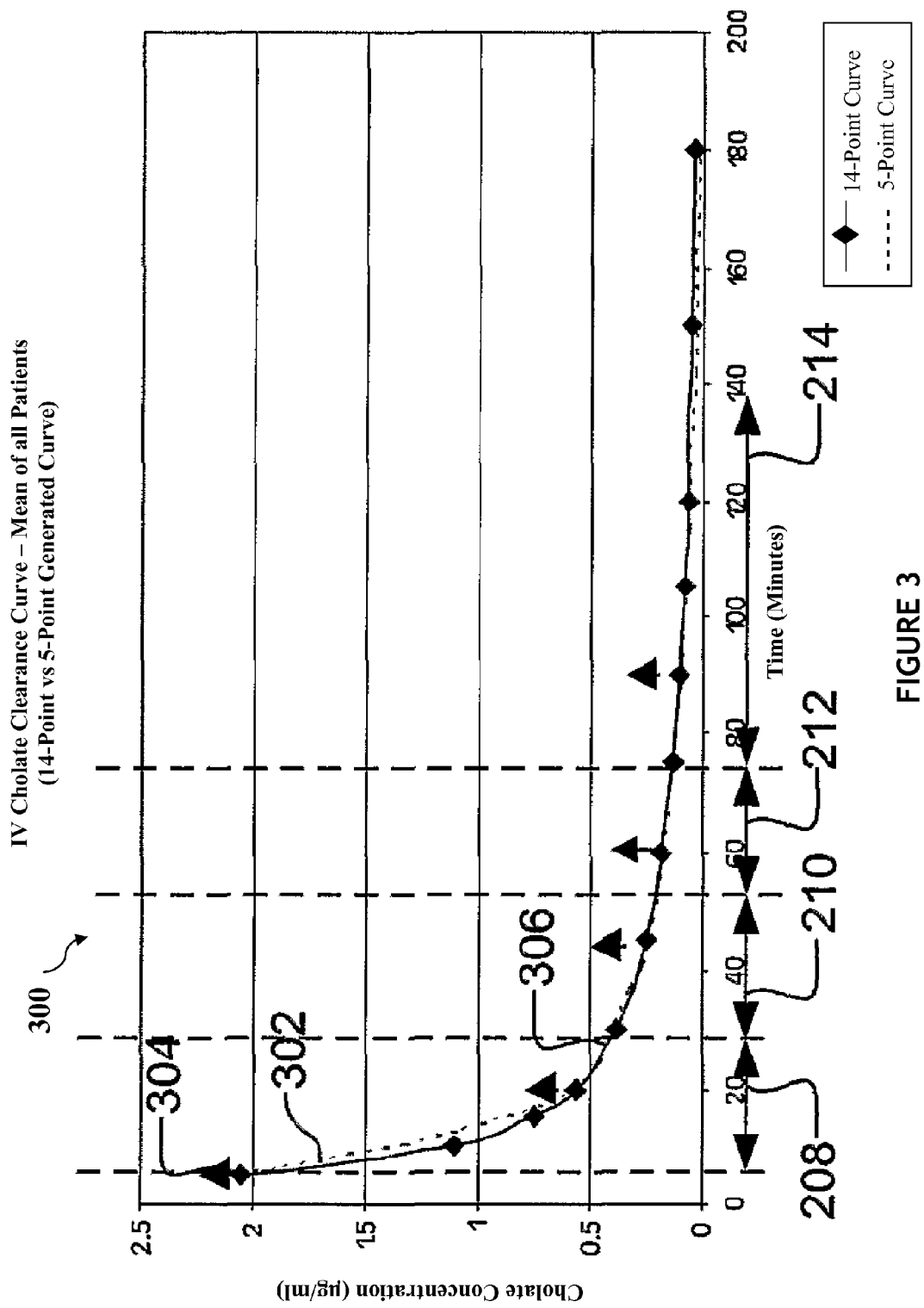
FIG. 3 illustrates a cholate IV clearance curve derived from an average of samples of over 300 patients administered cholate intravenously.

With regard to clinical testing with the use of a distinguishable agent, analysis typically involves determining clearance of the agent from a bodily fluid or sample such as the blood over time. Clearance generally refers to reduction or elimination of an agent concentration in the sample. The clearance can be graphically depicted with an agent concentration curve, which plots the concentration of the agent with respect to time. For a given agent, the concentration generally follows a similar curve for different patients. FIGS. 2 and 3 illustrate standard clearance curves that were derived from a sample of over 300 patients who were administered cholate orally (FIG. 2) and intravenously (FIG. 3). In this example, fourteen blood samples were taken from each of the patients to derive the standard clearance curves.

Referring to FIG. 2, the standard oral clearance curve 202 has characteristics (e.g., shape) that are generally similar among clearance curves derived from patients who have ingested cholate. For example, the clearance curve 202 can generally be characterized by a gradual increase in concentration, followed by an exponential decrease. Inflection points 204 and 206 are evident in the clearance curve 202. The general shape of the clearance curve 202 is characteristic of many agents in addition to cholate. As such, generally clearance curves derived from any administered agent such as an oral administration may include inflection points and the general shape as those shown in FIG. 2.

As another example, FIG. 3 is a graph 300 of a clearance curve 302 associated with intravenously (IV) administered cholate. The clearance curve 302 for IV administered cholate is characterized by sudden maximum concentration 304 around several minutes, followed by exponential decline in the concentration. An inflection point 306 generally occurs sometime during the exponential decline. The general shape of the clearance curve 302 is typical for most agents that are administered intravenously. As used herein, an IV clearance curve refers to a clearance curve associated with intravenous administration of an agent, and an oral clearance curve refers to a clearance curve associated with oral administration of an agent.

Although intravenous clearance curves for different agents share the same general shape and oral clearance curves for different agents share the same general shape, they typically differ in some ways. For example, the times at which inflection points occur can differ for different agents. In addition, the maximum values for agent concentrations can differ. Also, elimination rates can vary. However, because the clearance curves have the same general shapes for different agents, useful model clearance curves can be derived that can be used for conducting tests. Beneficially, such models can reduce the number of blood samples that need to be taken from the patients.

With the foregoing in mind, a process can be employed to identify characteristics associated with standard clearance curves for a distinguishable agent that is administered to a patient. These characteristics can be used to derive model clearance curves for future tests involving the agent. Turning to FIG. 4, the exemplary embodiment of algorithm 400 derives model characteristic curves for IV administered agent and orally administered agent based on selected times associated with characteristics (e.g., inflection points, slope, etc.) of standard IV and oral clearance curves. Although algorithm 400 is described with respect to cholate, those skilled in the art will recognize that the general process described can be readily adapted to other agents.

In a particular embodiment, prior to executing the algorithm 400, it is assumed that several hundred patients are each administered cholate orally and intravenously. At selected times after the administration of the cholate, blood samples are taken from each of the patients. In accordance with this embodiment, fourteen blood samples may be taken from each of the patients. However, the number of blood samples taken is not limited to fourteen and may be less or more than fourteen depending on the application. The fourteen blood samples per patient will be used to derive a standard fourteen point IV clearance curve and a standard fourteen point oral clearance curve. The blood samples are then prepared to obtain data that is input into the algorithm 400. One sample preparation protocol is described in Example 2 above.

In one embodiment, step 22 employs gas chromatography mass spectography (GC/MS). For example, a 6890/5973 mass spectrometer from Agilent Technologies, Inc. can be used. However, other mass spectrometers may be used. In other embodiments, high pressure liquid chromatography-mass spectography (HPLC/MS) is employed. For example, an Agilent 1100 series Liquid Chromatograph Mass Spectrometer equipped with a G1956A multi-mode source, automatic sampler, HP Chemstation Software or equivalent. The HPLC-MS can be fitted with a Agilent Eclipse XDB C8, 2.1×100 mm 3.5 um liquid chromatograph column.

The mass spectrometer is instructed (e.g., programmed) to monitor the prepared samples for ions specific to the particular agent of interest. In the embodiment described, the mass spectrometer is programmed to monitor for ions specific to cholate. In one embodiment, the ions monitored are specific to mass fragments of the agent. However, in other embodiments, other types of ions, such as the molecular ions can be monitored. The choice of which ions to monitor is dependant upon various factors related to the process, including, but not limited to, the molecular size of the agent and how the agent is derivatized.

After the samples are prepared, a receiving operation 402 receives the chromatographic data from the mass spectrometer related to intravenously administered cholate. Another receiving operation 404 receives chromatograph data related to orally administered cholate. In one embodiment of the algorithm 400, each of the receiving operations 402 and 404 receives fourteen data points representing an average of data from fourteen prepared blood samples.

A generating operation 406 generates a standard fourteen point IV clearance curve based on the received IV data. Another generating operation 408 generates a standard fourteen point oral clearance curve based on the received oral data. Those skilled in the art will readily recognize how standard fourteen point clearance curves can be generated in the generating operations 406 and 408.

Figure 5:
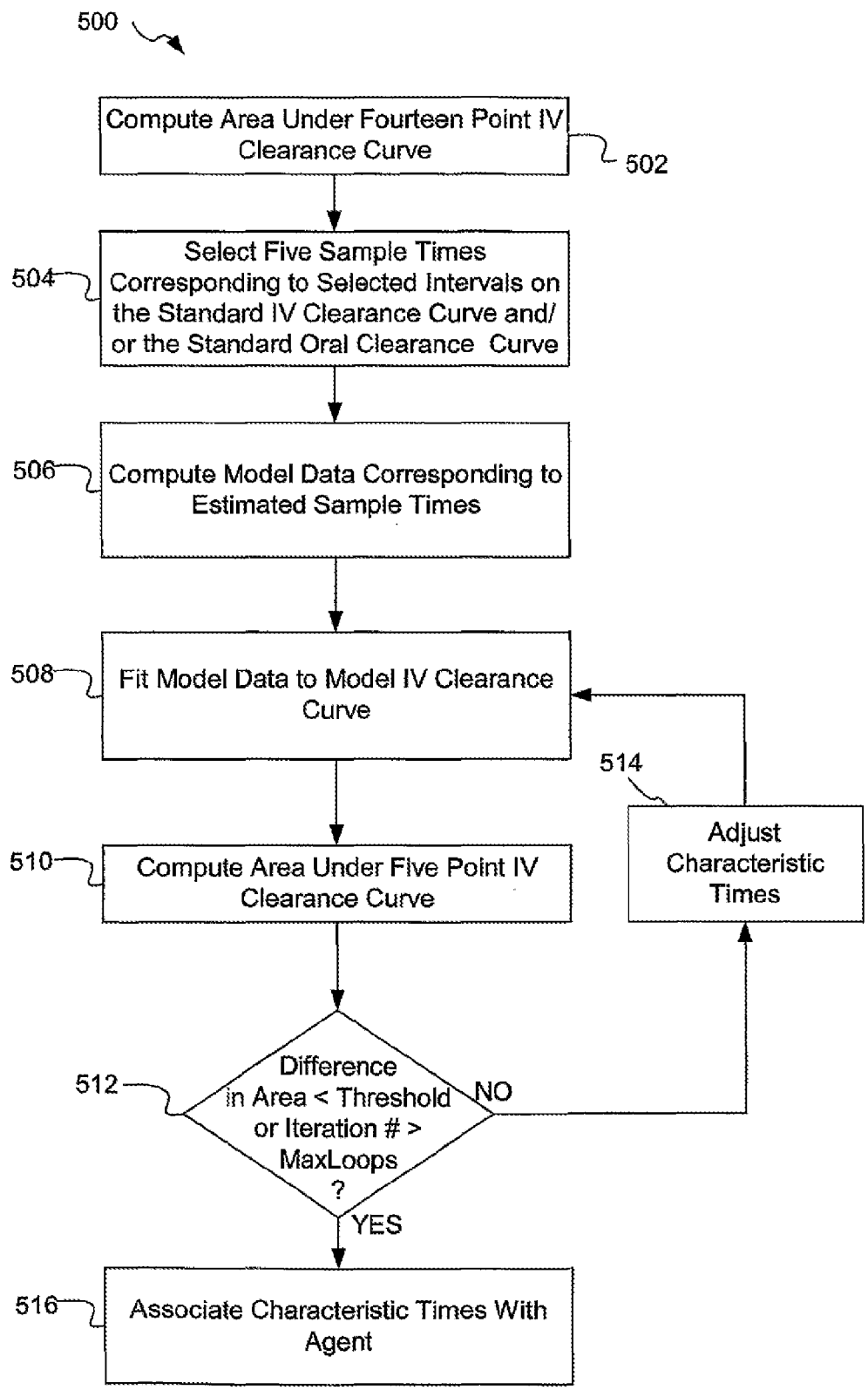
FIG. 5 illustrates a flow chart of an exemplary model IV clearance curve derivation algorithm 500 for generating a model IV clearance curve based on a standard 14 point IV clearance curve.
Figure 6:
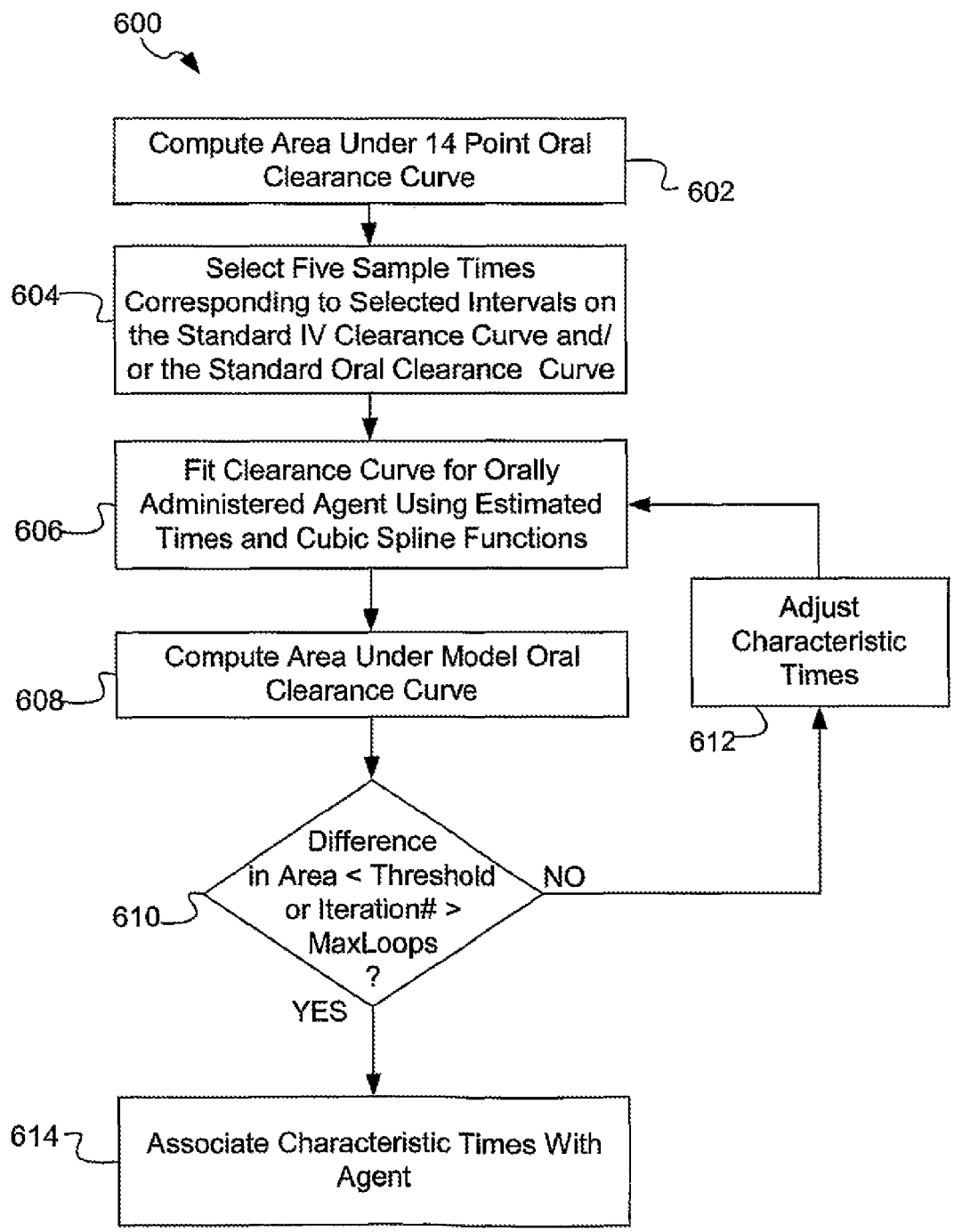
FIG. 6 illustrates a flow chart of an exemplary embodiment of an algorithm for deriving a model oral clearance curve based on a standard fourteen point oral clearance curve.

A deriving operation 410 derives a model IV clearance curve based on the standard fourteen point IV clearance curve. Another deriving operation 412 derives a model oral clearance curve based on the standard fourteen point oral clearance curve. Generally, the deriving operations 410 and 412 generate model data based on selected data points among the fourteen data points and fit the model data to a curve, referred to as a model clearance curve. An embodiment of the deriving operation 410 is shown in FIG. 5 and discussed in detail below. An embodiment of the deriving operation 412 is shown in FIG. 6 and is discussed in detail below.

As discussed, FIG. 5 illustrates a model IV clearance curve derivation algorithm 500 for deriving a model IV clearance curve based on a standard 14 point IV clearance curve. Referring to FIG. 5, initially the area under the 14 point IV clearance curve is computed in computing operation 502. Computing the area under a curve is generally understood by those skilled in the art. For example, area can be computed using known software programs, such as, but not limited to, EXCEL (MICROSOFT CORP.) or MATLAB (THE MATHWORKS, INC.). Alternatively, area can be computed using a proprietary program. A selecting operation 504 selects sample times corresponding to selected intervals on the standard fourteen point IV clearance curve and/or the standard fourteen point oral clearance curve. In another embodiment of the selecting operation 504, five sample times are selected. In further embodiments, more or fewer than five sample times can be selected. The selecting operation 504 can be carried out manually or automatically. In one embodiment, selecting manually involves visually observing the standard 14 point clearance curve and selecting times within intervals between characteristic points, such as inflection points. To illustrate, the oral clearance curve 202 in FIG. 2 includes four intervals: first interval 208, second interval 210, third interval 212, and fourth interval 214. In FIG. 2, the selected times are indicated by arrow markers 216. As shown in this particular embodiment, times at 5 minutes, 20 minutes, 45 minutes, 60 minutes, and 90 minutes are selected.

In a computing operation 506, model data is computed that will be used to generate the model clearance curve. In one embodiment of the computing operation 506, agent elimination rates are computed that correspond to each interval shown in FIG. 3. In this embodiment, agent elimination rates are computed using an exponential function. Equation (1) represents an exponential function characteristic of the clearance curve 302 in FIG. 3:

$$C_t = C_0 e^{-kt}, \quad \text{Eq.(1)}$$

wherein Ct represents the concentration of the agent at time 't', and 'k' represents the elimination rate.

For each interval, the exponential can be expressed as in Equation (2):

$$C_{t\,i+1} = C_{ti} e^{-k(ti-t\,i+1)}, \quad \text{Eq.(2)}$$

wherein 'i' represents an interval.

Using Equation (2), the elimination rate for each interval can be expressed as:

$$k_i = \ln(C_{t\,i+1}/C_{ti})/(t_i - t_{i+1}). \quad \text{Eq. (3)}$$

In a particular embodiment, four times, 5, 20, 45, and 90, are selected for the IV model clearance chart. Each of the selected times corresponds to one of the intervals. Corresponding elimination rates are shown below. To determine the first elimination rate, k1, Eq. (3) is simultaneously solved for $t_1 = 5$ minutes and $t_2 = 20$ minutes resulting in Eq. (4):

$$k_1 = \ln(C_{20}/C_5)/(t_1 - t_2). \quad \text{Eq. (4)}$$

To determine the second elimination rate, $k_2$, Eq. (3) is simultaneously solved for $t_3 = 45$ minutes and $t_4 = 90$ minutes resulting in Eq. (5):

$$k_2 = \ln(C_{90}/C_{45})/(t_3 - t_1). \quad \text{Eq. (5)}$$

To determine the function of the model clearance curve between $t_2 = 20$ minutes and $t_3 = 45$ minutes, a third elimination rate, $k_3$, can be solved in the same manner as above resulting in Eq. (6):

$$k_3 = \ln(C_{45}/C_{20})/(t_2 - t_3). \quad \text{Eq.(6)}$$

In a fitting operation 508, the elimination rates are used to fit a curve based on five points obtained from the fourteen received IV points. In one embodiment, the fitting operation 508 substitutes the computed elimination rates, $k_1$, $k_2$, and $k_3$ into Eq. (1) above for each interval in order to create a model IV clearance curve.

A computing operation 510 computes the area under the model IV clearance curve that was fitted in the fitting operation 508. Any of various area computation methods may be used as discussed above with respect to the computing operation 502.

After the area is computed for the model IV clearance curve, a determining operation 512 determine whether the area under the model IV clearance curve is within a predetermined range of the area under the standard 14 point IV clearance curve. In one embodiment, the difference between the two areas is computed. The difference in areas is then compared to a specified threshold. The specified threshold can be set to any value that is applicable to the particular application.

If the determining operation 512 determines that the area under the model IV clearance curve is not within the predetermined range of the area under the standard 14 point IV clearance curve, the algorithm branches 'NO' to an adjusting operation 514. The adjusting operation 514 adjusts the estimated sample times in a manner to make the two computed areas closer in value. The adjusting operation 514 can be carried out manually or in an automated fashion.

If the determining operation 512 determines that the area under the model IV clearance curve is within the predetermined range of the area under the standard 14 point IV clearance curve or the algorithm 500 has looped more than MaxLoops times, the algorithm branches YES to an associating operation 516, which associates the selected times with the distinguishable agent that was intravenously administered. MaxLoops is a specified value that is chosen to ensure that looping eventually stops and sample times are associated with the distinguishable agent.

FIG. 6 is an embodiment of an algorithm 600 for deriving model oral clearance curve based on a standard 14 point oral clearance curve. Initially computing operation 602 computes the area under the standard 14 point oral clearance curve. An selecting operation 604 then selects sample times based on the standard 14 point oral clearance curve. One embodiment of the selecting operation 604 selects five sample times; however, in other embodiments, the number of sample times may be more or fewer than five sample times.

The estimated five times are generally based on characteristics (e.g., inflection points) of the standard 14 point oral clearance curve. The selecting operation 604 can be carried out manually or in an automated fashion. In some embodiments, the selecting operation 604 can select the times derived in the model IV clearance curve derivation 500.

A fitting operation 606 then fits a model clearance curve for the orally administered cholate using the five sample times determined in the selecting operation 604. One implementation of the fitting operation 606 employs a cubic spline function, as shown in Eq. (7):

$$f_i(t) = [f''(t_i-1)/6(t_i-t_{i-1})](t_i-t)^3 + [f''(t_i)/6(t_i-t_{i-1})]$$
$$(t-t_{i-1})^3 + \{[f(t_{i-1})/t_i-t_{i-1}] - [f''(t_{i-1})/6]\}(t_i-t) +$$
$$\{[f(t_i)/t_i-t_{i-1}] - [f''(t_i)(t_i-t_{i-1})/6]\}(t-t_{i-1}), \quad \text{Eq. (7)}$$

wherein $f_i(t)$ represents the model clearance curve function during interval 'i' with respect to time, 't'.

Eq. (7) has two unknown second derivatives, f'', for each interval. To solve for the two unknown second derivatives, Eq. (7) can be differentiated to give an expression for the first derivative for both the (i−1)th and the ith intervals. Then the two results can be set equal, assuming that the first derivatives at contiguous points on the clearance curve are continuous:

$$f'_{i-1}(t_i) = f'_1(t_i). \quad \text{Eq. (8)}$$

The following relationship results:

$$(t_i-t_{i-1})f''(t_{i-1}) + 2(t_{i+1}-t_{i-1})f''(t_1) + (t_{i+1}-t_i)f''(t_{i+1}) =$$
$$[6/(t_{i+1}-t_i)][f(t_{i+1})-f(t_i)] + [6/(t_i-t_{i+1})][f(t_{i-1})-f(t_i)]. \quad \text{Eq.(9)}$$

Also noting the second derivatives at the endpoints are 0, four equations and four unknowns can be written and solved for all unknown second derivatives. After the second derivatives are solved for, complete spline functions could be generated for all 4 intervals. Using the above cubic spline equations, the model oral clearance curve is generated for intervals 208, 210, 212, and interval 214 up to t=90 minutes. (FIG. 2). To generate the portion of the model oral clearance curve after 90 minutes, an exponential function is used. In one embodiment, the exponential function after 90 minutes is derived by computing the average 'k' elimination rate for all sample patients. The average 'k' elimination rate is then used in Eq. (1) to generate the remaining portion of the model oral clearance curve. This average 'k' elimination rate is the same k elimination derived from the IV clearance curve. In this case, the IV and oral clearance curves decay at the same rate.

After the model oral clearance curve is generated, a computing operation 608 computes the area under the model oral clearance curve. A determining operation 610 determines whether the area under the model oral clearance curve is within a predetermined range of the area under the standard 14 point clearance curve. If the difference between the two areas is not less than a specified threshold, the algorithm 600 branches 'NO' to an adjusting operation 612. The adjusting operation 612 adjusts the sample times to make the two area values closer in value. After the times are adjusted, the fitting operation 606 again fits the model data to a model oral clearance curve.

Figure 7:
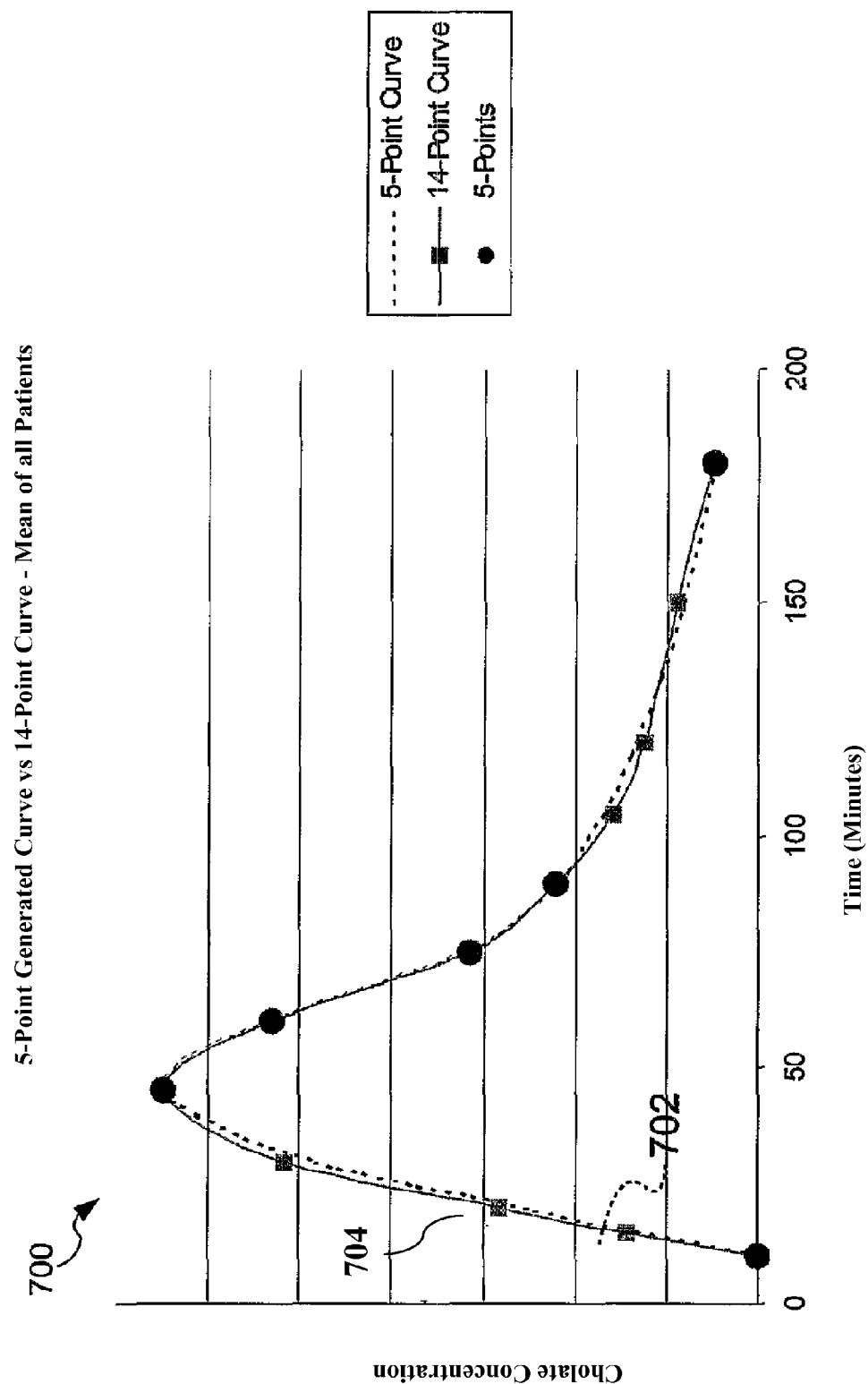
FIG. 7 illustrates an average oral clearance curve derived from a sampling of over 300 patients showing a model five point oral clearance curve and a standard fourteen point clearance curve from which the model curve was derived.

If the determining operation 610 determines that the area under the model oral clearance curve and the standard 14 point clearance curve are within the predetermined threshold or the algorithm 600 has looped more than MaxLoops times, the algorithm 600 branches YES to an associating operation 614. The associating operation 614 associates the five selected times with the distinguishable agent. FIG. 7 is an exemplary graph 700 showing a model five point oral clearance curve 702 (dotted line) and a standard 14 point clearance curve 704 (solid line) from which the model curve 702 was derived. Thus, in future tests, the patient may only need to provide blood samples at less selected times such as five selected times (e.g., 5, 20, 45, 60, and 90 minutes), and, using the model oral clearance curve 702, an individualized clearance curve can be generated for the patient.

To calculate the liver shunt fraction, the exponential decay equations and the spline function equations, generated mathematically by the 5 selected points, are integrated along their respective valid time ranges and an area is generated. The liver shunt fraction is then calculated:

$$\text{ShuntFraction} = [\text{AUC}_{oral}/\text{AUC}_{IV}] * [\text{Dose}_{IV}/\text{Dose}_{oral}] * 100\%, \quad \text{Eq. (10)}$$

wherein AUC represents area under the curve and Dose represents the amount (in mg) of dose administered.

The model IV clearance curve derivation algorithm 500 and the model oral clearance curve derivation algorithm 600 may be carried out together. For example, in some embodiments, the algorithms 500 and 600 are carried out in serial. In other embodiments, the algorithms 500 and 600 are carried out in parallel. By carrying out the two algorithms together, the sample times for both the IV clearance curve and the oral clearance curve can be selected so that they are equal. In addition, the order of operations described in FIGS. 5-6 are not limited by the orders shown. In some embodiments, operations may be carried out in different orders, and operations may be merged or separated without straying from the scope and spirit of the claimed invention.

Example 6

An Exemplary Clinical and Biochemical Endpoint Study of Disease Progression

In one example study, two long term studies examined rates of disease progression in patients with HCV with bridging fibrosis and cirrhosis. One study used these estimates to calculate samples sizes for the current NIH treatment trial based upon an equal distribution of noncirrhotic and cirrhotic patients. Disease progression can be defined herein as an increase in fibrosis score of 2 points or more, or development of hepatic decompensation, death from liver disease, or HCC. Table 4 presents a total sample size that would be required to achieve 90% power for a binomial chi-square test with a two-sided alpha of 0.05.

TABLE 4

Statistical sample size at various clinical event rates.

|  | A | B | C | D |
|---|---|---|---|---|
| Control (%/yr) | 4.0 | 5.0 | 6.0 | 7.0 |
| Control (%/4 yr) | 15.1 | 18.5 | 21.9 | 25.2 |
| 50% decrease in Endpoints |  |  |  |  |
| IFN (%/yr) | 2.0 | 2.5 | 3.0 | 3.5 |
| IFN (%/4 yr) | 8.7 | 10.8 | 12.8 | 14.9 |
| N for 90% power | 1084 | 870 | 728 | 626 |
| Noncompliance (5%/yr) |  |  |  |  |
| IFN (%/4 yr) | 9.3 | 11.5 | 13.6 | 15.8 |
| N for 90% power | 1324 | 1064 | 890 | 767 |

During the first 6 months of therapy, all patients can be treated and control and maintenance therapy groups experience disease progression at the same rate. If the control group has an annual clinical event rate of 7% (column D), then 25.2% will have developed a clinical event by the end of four years. If maintenance treatment reduces the annual rate by 50% and if treatment is started after 6 months, then the event rate will be 14.9% at the end of four years. If 5% of the treated group become noncompliant each year, then the event rate required to maintain significance would be 15.8% at the end of four years. Approximately 1200 patients will need to be enrolled into the trial to achieve statistical significance for the primary endpoint. The ability of the study to determine efficacy for maintenance therapy would be compromised if either the rate of development of clinical endpoints is lower than projected or if rates of dropout from the trial exceed 5%/yr.

Example 7

Use of Multiple QLFTs in Other Populations (the HALT C Study)

In one example, seven QLFTs were used to define hepatic impairment in patients with chronic hepatitis C and bridging fibrosis or compensated cirrhosis enrolled in the Hepatitis Antiviral Long-Term Treatment to Prevent Cirrhosis Trial (HALT C). These results can be compared to those with or without biopsy-proven cirrhosis, splenomegaly on ultrasonography, and varices at endoscopy.

The mean age of the 248 enrolled patients was 49.9+/−7.3 yr and 75% were male. Mean BMI was 29.6+/−5.3, 40% had cirrhosis, 60% had bridging fibrosis, 93% were infected with HCV genotype 1, and mean serum HCV RNA was 4.39+/−4.66×10$^6$ copies/ml. 30% had platelet count <140,000/microliter, 25% had albumin <3.5 g/dl, 25% had INR >1.1, 10% had bilirubin >1.2 mg/dl, and 25% had AST:ALT >1.

$^{13}$C-methionine (MBT), caffeine (Caf), antipyrine (AP), and 2,2,4,4-$^2$H-cholate (CA) were taken orally and 24-$^{13}$C-cholate, galactose (Gal), and lidocaine were administered intravenously. These compounds or their metabolites were measured from timed serial samples of blood, saliva, and breath using standard techniques. Elimination rate (kelim), volume of distribution (Vd), clearance (Cl), elimination capacity (Elim), and shunt were calculated from measured analytes. Perfused hepatic mass (PHM) was determined from SPECT liver scan. Mean test results were compared by T statistic and area under the receiver operator curve (ROC) by C statistic. Table 5 presents results ordered by T statistic for association with cirrhosis.

TABLE 5

Results of QLFTs and correlation with various hepatic conditions.

| Test | % of Pts with Abnl Test | Cirrhosis T-Stat | P | Splenomegaly T-Stat | P | Varices T-Stat | P |
|---|---|---|---|---|---|---|---|
| CA Cl$_{oral}$ | 70% | 7.74 | .0000 | 3.32 | .0010 | 3.97 | .0001 |
| PHM | 65% | 6.92 | .0000 | 3.93 | .0002 | 4.95 | .0000 |
| CA Shunt | 75% | −6.73 | .0000 | −3.65 | .0003 | −3.81 | .0002 |
| Ca k$_{elim}$ | 48% | 3.78 | .0002 | 2.33 | .0207 | 1.09 | NS |
| AP k$_{elim}$ | 82% | 3.61 | .0004 | 2.56 | .0116 | 2.09 | .0399 |
| MBT Score | 67% | 2.87 | .0046 | 3.46 | .0007 | 2.43 | .0169 |
| CA k$_{elim}$ | 38% | 2.86 | .0047 | 1.25 | NS | 2.36 | .0195 |
| Gal Elim | 73% | 2.58 | .0106 | 3.87 | .0001 | 2.28 | .0240 |
| AP Cl | 58% | 2.44 | .0160 | 1.37 | NS | 1.84 | NS |
| MEGX 15 min | 75% | 1.33 | NS | 1.91 | .0572 | 1.88 | NS |
| MEGX 30 min | 67% | 1.01 | NS | 1.77 | NS | 1.01 | NS |

PHM had the highest area under ROC with cirrhosis (c-statistic 0.87), splenomegaly (c-statistic 0.75), and varices (c-statistic 0.832) and correlated best with platelet count, bilirubin, prothrombin time, and albumin.

QLFTs may uncover hepatic impairment in fibrotic patients with chronic hepatitis C. Certain tests, particularly CA Cloral, PHM, and CAshunt, identify patients with chronic hepatitis C with cirrhosis, splenomegaly or varices. Long-term follow-up may determine whether hepatic impairment as defined by QLFTs predicts risk for clinical deterioration.

Example 8

Multiple Tests to Assess Hepatic Function

The following example includes multiple tests to assess hepatic function. These can include measurement of blood flow with cholate clearance, portal shunt with dual isotope cholate, and microsomal function with antipyrine clearance, caffeine clearance, MEGX formation from lidocaine and erythromycin breath test. Trough (C1) and peak (C2) concentrations of TAC and MMF concentrations at trough, 1 h, and 2 h post-dose, relative to dose, can be measured in all recipients. Volumetric studies can be performed using MRI, and functional mass will be measured using the SPECT liver-spleen scan.

Cholate clearance and portal shunt (Blood Flow) involve administration and measurement of cholate test compounds. Intravenous $^{13}$C-cholate, for example 20 mg, can be dissolved in NaHCO$_3$ solution, passaged through a micropore filter, and placed in sterile, capped glass vials prior to use. This preparation is mixed with 5 ml of 25% human albumin solution just prior to intravenous injection. The $^2$H4-cholate, for example 40 mg, is taken orally. Blood samples for measurement of cholate isotopes can be obtained at baseline and 5, 10, 15, 20, 30, 45, 60, 75, 90, 105, 120, 150, and 180 minutes post-dose (14 samples, 7 ml red top tubes). Serum concentrations of cholate are determined by GC/MS-isotope ratiometry. Comparison of intravenous and oral clearance curves allows determination of first-pass hepatic elimination or portal shunt.

Other tests can be used in combination with the cholate shunt and cholate clearance tests.

Antipyrine and caffeine clearances. Saliva samples, for measurement of antipyrine, can be obtained at baseline and at 6, 12, 24, 36, 48, and 60 hours post-dosing (e.g. 7 samples, mls each). Salivary concentrations of antipyrine and caffeine are measured by HPLC.

Erythromycin breath test. Breath samples for measurement of $^{14}$CO$_2$ from the metabolism of $^{14}$C-erythromycin are obtained prior to and 20 minutes after IV administration of $^{14}$C-erythromycin. Breath samples are analyzed for radioactivity by trapping exhaled CO$_2$ and liquid scintillation counting.

MEGX from lidocaine. Blood samples for measurement of MEGX (monoethylglycinexylidide) from the metabolism of lidocaine are obtained prior to and over 1 hour after the IV administered dose of lidocaine (0.5 mg/kg). MEGX is measured by HPLC.

The data provided by the combination tests will be used to assess overall organ health and in particular hepatic health. All samples for the above clearance studies will be coded with a unique identifier, dated, and collection time, center, PI recorded and samples stored in tightly-capped vials, and shipped on dry ice to the analytical laboratory.

Example 9

Determination of Minimal Number of Sample Time Points in Cholate Clearance and Cholate Shunt: Development of a "Minimal Model"

Standard methods for measuring oral cholate clearance and shunt, requiring 14 samples of blood collected over 3 h, are clinically impractical. For these reasons mathematical methods were used to define the minimal sampling requirements.

In this example, a study of patients with chronic hepatitis C was used and a mathematical model of cholate clearance curves was used to generate one minimal model necessary to accurately measure cholate shunt in humans. Deconvolutional analysis was utilized on clearance curves of simultaneously administered oral and intravenous Doses of 2,2,4,4-$^2$H Cholate and 24-$^{13}$C Cholate in order to determine a minimal model for first-pass hepatic extraction of cholate in humans.

The following analysis was used to assess the minimal number of time points for accurate determination of cholate clearance. Patients (n=286) were enrolled in HALT C trial and participated in the QLFT (quantitative liver function test) ancillary study; 73 patients were studied twice at different times. Each patient was subjected to the following test protocol. 20 mg of 24-$^{13}$C cholic acid was dissolved in NaHCO$_3$, mixed with 5 ml 25% human albumin solution and injected through an indwelling intravenous catheter over 2 minutes. 40 mg of 2,2,4,4-$^2$H cholic acid was dissolved in water, mixed in juice and taken orally simultaneously with the intravenous injection. Blood samples were drawn through the indwelling catheter and taken prior to isotope administration and 5, 10, 15, 20, 30, 45, 60, 75, 90, 105, 120, 150 and less than 180 minutes post-dose.

Samples were processed and analyzed by GC/MS as described above to obtain oral and intravenous cholic acid clearance curves. Briefly, serum concentrations of differentially labeled $^{13}$C and $^2$H cholates were determined from 0.5 ml aliquots of serum. 1.5 micrograms of unlabelled cholate was added to each serum sample. The cholates were isolated by extraction from serum with Sep-Pak C18 cartridge, acidification, ether extraction, methylation, TMS derivatization, and capillary GC/MS isotope ratiometry, as described above. Cholate shunt was calculated as (AUC$_{oral}$/AUC$_{iv}$)×(Dose$_{iv}$/

Dose$_{oral}$)×100%. A full description of the methods and mathematical models used in curve fitting, measurement of AUC and analysis of models is provided in the supplementary Materials section-Appendix S1 of Everson et al., which is incorporated herein by reference in its entirety.

Figure 8:
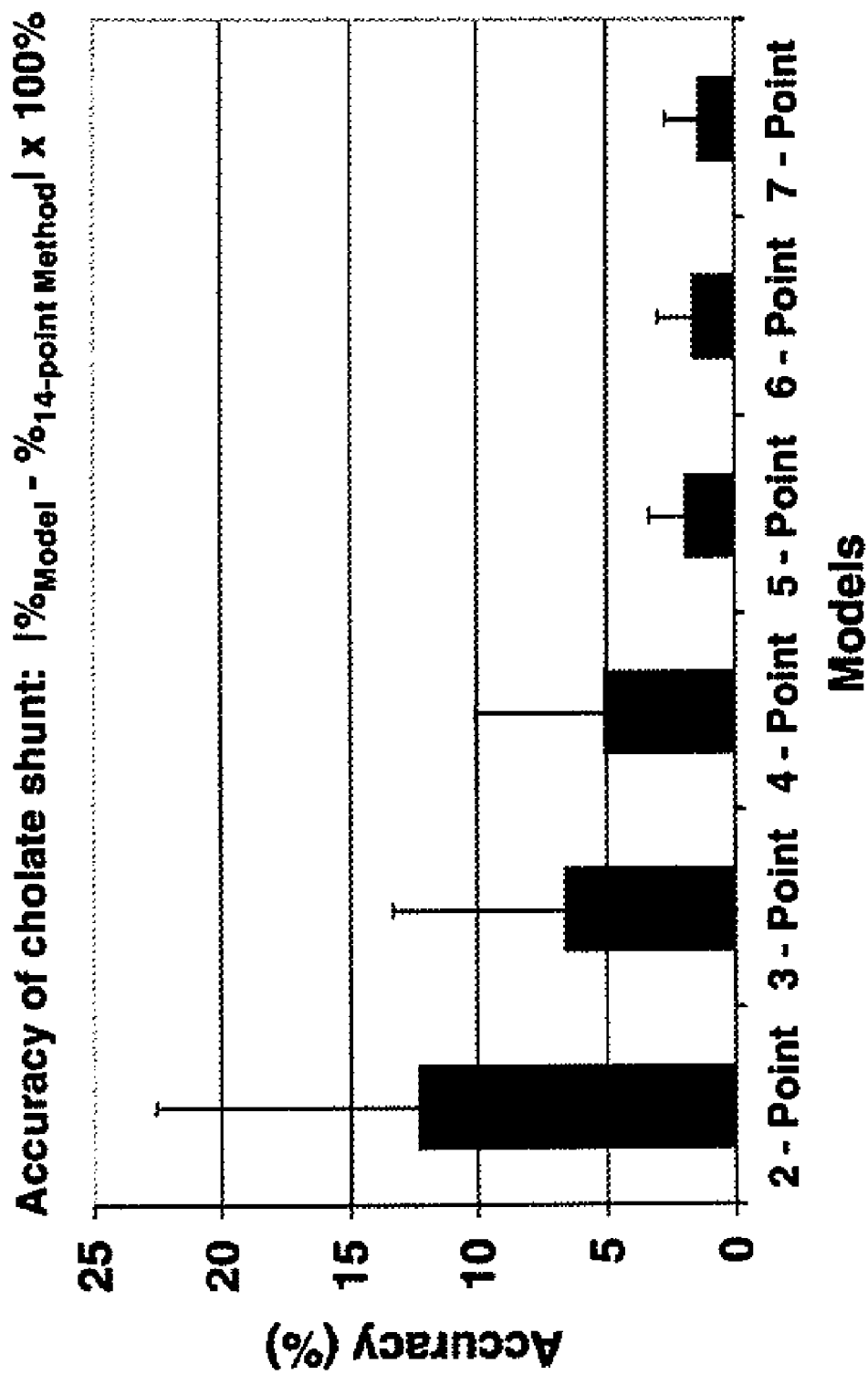
FIG. 8 shows mean differences (+/−s.d.) of measurements of cholate shunt using reduced numbers of time points in comparison to the standard 14 time point method.

Deconvolutional analysis was performed on the 14-point intravenous and oral clearance curves to obtain the minimal amount of points and time period required to regenerate the full curves. Two to seven time points spanning time periods from 5 to 180 minutes were modeled. Mean differences of measurements (+/− standard deviation) of cholate shunt with various models using reduced numbers of sample time points in comparison with the 14-point method are shown in FIG. 8. Models using less than five points were associated with significant mean error and higher variation. Models incorporating five points or more were equivalent and within 1-2% of the measurement of cholate shunt by the 14 point standard method.

The analysis indicates that cholate shunt may be accurately determined from 5 samples of blood obtained approximately 5, 20, 45, 60 and 90 minutes post dose. These time points bracket inflection points in the clearance curves. The accuracy of the 5 point curve, coined a "minimal model", in measurement of cholate shunt was 98.1+1.4% of that calculated using all 14 time points. Use of fewer samples or time points that fail to bracket inflection points was found to diminish the accuracy of measurement of cholate shunt. The "minimal model" defined by this analysis significantly reduces the number of samples and time commitment required to determine cholate shunt in humans. This can improve patient comfort, compliance with testing, reduce human error in sample collection and analysis, reduce time and expense, and save resources. The 5-point model greatly simplifies performance of the test increasing its potential for broader application in the assessment of patients with liver disease. Switching from 14 time points to five time points reduces patient phlebotomies by 64% patient sampling time by 50%, and laboratory analysis and sample preparation by 64%.

The 5-point model is generally applicable to all test compounds that exhibit certain characteristics comparable to cholate. Key characteristics include relatively high first-pass hepatic elimination, rapid and complete intestinal absorption, retention of the test compound in the intravascular space, lack of dependency on hepatic metabolism, lack of renal excretion and lack of direct effects of the test compound on the cardiovascular system or portal circulation. Cholate fulfills all of these criteria. Further validation of cholate as an appropriate test compound for assessment of portal blood flow and portal-systemic shunt is the fact that the measurement of mean cholate shunt in healthy intact human subjects (18%, or 82% first-pass hepatic elimination from the portal vein) is identical to expected, based upon other studies of the liver or liver cells.

Example 10

Liver Metabolic Function: Caffeine Clearance Test

Clearance of caffeine depends upon specific hepatic metabolic pathways and its measurement, which quantitates liver metabolic function, requires multiple samples for up to 3 days. One method for measuring deuterated isotopes of caffeine is described for determining clearance from single samples of serum.

Example protocol. In one example, a study was performed to analyze hepatic condition of HCV patients using a multi-isotope method for measurement of caffeine elimination (TIME test). Caffeine concentrations range from 0.1 to 6 micrograms/ml over 24 h after a single oral dose of 300 mg. Deuterated caffeine (D3 and D9), unlabeled caffeine, and phenacetin (500 ng/ml) were added to five separate samples of calf serum and extracted after alkalinization using methylene chloride. The methylene chloride layer was taken to dryness and reconstituted in 50 microlites of acetone. Compounds were analyzed by GC-MS with an initial oven temperature of 40° C. for 0.55 min, increasing at 50° C./min to 280° C., held isothermally at 280° C. for 4 min, and quantified by selected ion monitoring (m/z 179, 194, 197, and 203) using calibration curves with phenacetin as internal standard.

Example outcome. The correlation coefficients for the calibration curves were 0.995, 0.996 and 0.995 for unlabelled, D3 and D9 caffeines, respectively.

X+/−SD and coefficients of variance (CV) for unlabeled caffeine (2800 ng/mL) and D3 & D9 (400 ng/mL each) were: 2800+/−109, 3.9%; 411+/−18, 4.4%; and 385+/−16 ng/ml, 4.2%, respectively. Instrument precision was 99.50%, 99.38%, and 99.51%, respectively. These concentrations reflect expected concentrations in human serum 4 h after an oral dose of 300 mg of total caffeine at a molar ratio D3 (or D9): unlabeled caffeine of 1:7.

X+/−SD, and CV of unlabeled caffeine (600 ng/mL) and D3 & D9 (150 ng/mL each), were 539+/−61, 11%; 143+/−12, 8.4%; and 135+/−16 ng/mL, 12% with precision of 98.73%, 99.43% and 99.22%, respectively. These concentrations reflect expected concentrations in serum 24 h after an oral dose of 300 mg total caffeine with a molar ratio of D3 (or D9): unlabeled caffeine of 1:4. This example method accurately quantifies caffeine and deuterated isotopes over concentration ranges achieved after oral dosing with 300 mg caffeine.

A triple isotope method (TIME test) by performance of appropriate clinical testing of human subjects and comparison of the results to standard caffeine clearance assays can be evaluated as follows:

TABLE 6

TIME assay study groups.
Validation Study

| | | |
|---|---|---|
| Subjects: | Group 1: | Healthy controls (N = 10) |
| | Group 2: | HCV patients, Ishak fibrosis stage 0-2 (N = 10) |
| | Group 3: | HCV patients, Ishak fibrosis stage 4-6 (N = 10) |

Protocol A: Subjects are placed on a caffeine-free diet for 3 days then admitted to a monitoring center such as GCRC. Baseline samples of blood, serum and saliva for measurement of for example caffeine, CBC, INR, Chemistry profile (creatinine, liver tests included), pregnancy test and a history and physical examination.

TABLE 7

Administration of caffeine and caffeine isotopes.
Unlabelled

| | |
|---|---|
| Isotope 1 | Time = t1 |
| Isotope 2 | Time = t2 |
| Isotope 3 | Time = t3 |

Post-dose samples were obtained as Sample 1, 2, 3, 4 and 5. Repeat the study (items 1-5 above) after washout, 24 h<washout <7 d.

Protocol B: Same as Protocol A, but with no caffeine-free diet. Subjects are admitted to a monitoring center such as GCRC. Baseline samples of blood, serum and saliva for measurement of for example caffeine, CBC, INR, Chemistry profile (creatinine, liver tests included), pregnancy test and a history and physical examination.

Methods:
1. Addition of phenacetin as internal standard.
2. Extraction of caffeine and caffeine isotopes from samples.
3. Standard caffeine analysis by HPLC.
4. Caffeine isotopes are measured by GC/MS or HPLC/MS.

Calculations:
1. Multiple sampling: Ln/linear regression of [caffeine] vs time. Slope=elimination rate constant. Intercept yields [caffeine] at t=0, Vol of distribution calculated. Clearance product of elimination rate and vol of distribution.
2. Single samples (TIME test). Each sample is analyzed for concentration of each of the 3 isotopes. Sample time is difference between time of isotope administration and time of collection. Ln/linear regression of [caffeine] vs time, yields elimination rate, vol dist, and Cl.

Statistics
1. Compare elim rate, vol dist, and Cl between standard and TIME methods, using Protocol A data. 2. Compare effect of dietary caffeine on both standard and TIME methods by comparing results for each method between Protocol A and Protocol B. 3. Define reproducibility of standard and TIME methods by comparing the initial and repeat studies done in both protocol A and protocol B.

The TIME test may be used alone or in combination with a cholate shunt assay or one or more other QLFTs to provide a comprehensive assessment of hepatic condition. Similarly, this test could be used to assess impact of disease, disease progression, therapies, interventions or transplantation.

Example 11

Impact of Virological Response on Hepatic Function

The goal of this study was to determine the relationships of quantitative liver function tests (QLFTs) with virological responses to peginterferon (PEG)+/−ribavirin (RBV) in patients with chronic hepatitis C. Serial QLFTs were used to define the spectrum of hepatic improvement after sustained virological response (SVR).

Rates of sustained virological response (SVR) with peginterferon/ribavirin treatment of chronic hepatitis C are lower in patients with advanced hepatic fibrosis or cirrhosis. In the Hepatitis C Antiviral Long-term Treatment against Cirrhosis (HALT-C) Trial, patients with chronic hepatitis C with bridging fibrosis or compensated cirrhosis [Child-Turcotte-Pugh (CTP)≤6] and prior nonresponse were retreated with peginterferon/ribavirin. In this cohort, SVR after retreatment declined stepwise, from 23% to 9%, with increasing severity of disease, as defined by liver histology and platelet count. Because quantitative liver function tests (QLFTs) measure the continuum of liver impairment, it was reasoned that the relationship between SVR and disease severity might be better defined by QLFTs. Sustained virological response reduces hepatic inflammation, fibrosis, and rates of clinical outcomes. The principal clinical manifestations of advanced chronic hepatitis C, such as varices, ascites and encephalopathy are linked to portal hypertension and impaired hepatic function. Beneficial effects of SVR on hepatic fibrosis and clinical outcomes are probably mediated through improvements in the portal circulation and hepatic function—improvements which could be detected by QLFTs, but not by standard laboratory tests.

In this study of retreatment of patients with chronic hepatitis C with peginterferon/ribavirin, a battery of QLFTs was utilized to measure hepatic metabolism, hepatic and portal blood flow, portal-systemic shunting and hepatic parenchymal mass. One goal was to define the relationships between severity of hepatic impairment, as measured by QLFTs and virological responses. In addition, serial QLFTs were used to define hepatic improvement after achievement of SVR.

Participants (n=232) were enrolled in the Hepatitis C Antiviral Long-term Treatment against Cirrhosis (HALT-C) Trial, had failed prior therapy, had bridging fibrosis or cirrhosis and were retreated with PEG/RBV. All 232 patients had baseline QLFTs; 24 patients with SVR and 68 nonresponders had serial QLFTs. Lidocaine, [24-$^{13}$C]cholate, galactose and $^{99m}$Tc-sulfur colloid were administered intravenously; [2,2,4,4-$^2$H]cholate [1-$^{13}$C]methionine, caffeine and anitipyrine were administered orally. Clearances (Cl), breath $^{13}CO_2$, monoethylglycylxylidide (MEGX), perfused hepatic mass (PHM) and liver volume were measured as described above and in Everson et al., 2009 "Quantitative tests of liver function measure hepatic improvement after sustained virological response: results from the HALT-C trial", Aliment. Pharmacol. Ther. 29, 589-601, which is incorporated herein by reference.

Results

Figure 10:
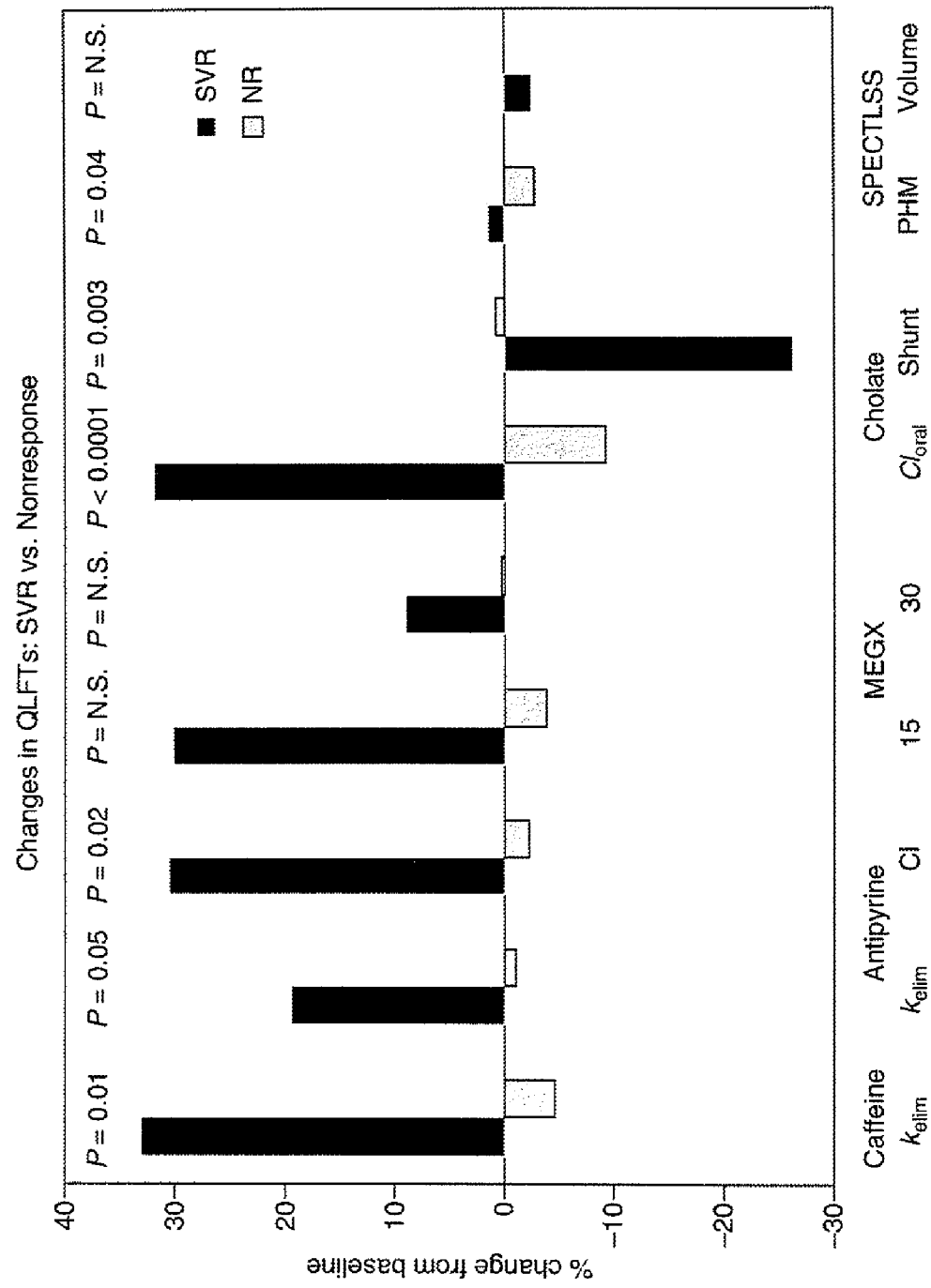
FIG. 10 shows the percentage change between baseline and follow-up studies for various QLFTs. The black bars depict the changes after SVR, and the grey bars show the changes in patients with nonresponse (NR).

Rates of SVR were 18-26% in patients with good function by QLFTs, but less than or equal to 6% in patients with poor function. Results are shown in FIG. 10 which shows the percentage change between baseline and follow-up studies for various QLFTs. The black bars depict the changes after SVR, and the grey bars show the changes in patients with nonresponse (NR). Compared to patients with nonresponse, patients experiencing SVR had significant improvements in caffeine and antipyrine elimination rates ($k_{elim}$), antipyrine clearance (Cl), clearance of orally administered cholate ($Cl_{oral}$), cholate shunt and perfused hepatic mass (PHM). Hepatic metabolism, as measured by caffeine $k_{elim}$ (P=0.02), antipyrine $k_{elim}$ (P=0.05) and antipyrine clearance (P=0.02) improved after SVR. The portal circulation, as measured by cholate oral clearance (P=0.0002), cholate shunt (P=0.0003) and PHM (P=0.03), also improved significantly after SVR.

Figure 9:
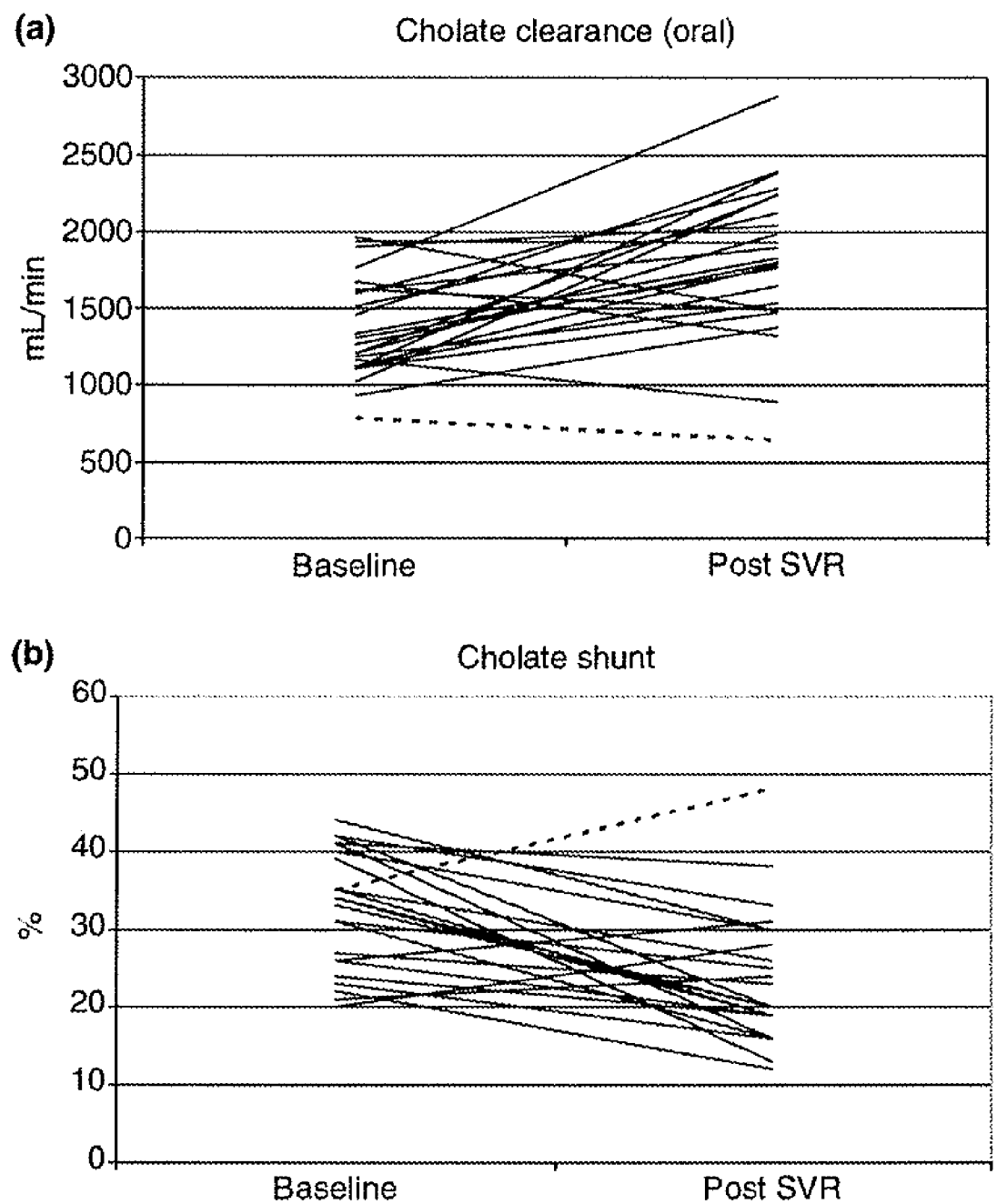
FIG. 9 shows orally administered cholate clearance and cholate shunt at baseline and post-SVR. Sustained virological response was associated with a 32% increase in cholate oral clearance, a measure or portal blood flow, as shown in FIG. 9(a). Sustained virological response was also associated with a 26% decrease in cholate shunt, a measure of portal-systemic shunting, as shown in FIG. 9(b).

Cholate oral clearance and cholate shunt, both measurements of portal circulation, improved significantly after SVR. Cholate oral clearance and cholate shunt at baseline and post-SVR are shown in FIG. 9. Sustained virological response was associated with a 32% increase in cholate oral clearance, a measure or portal blood flow, as shown in FIG. 9(a). Sustained virological response was also associated with a 26% decrease in cholate shunt, a measure of portal-systemic shunting, as shown in FIG. 9(b).

Example 12

Cholate Shunt, IV and Oral Cholate Clearance Tests with analysis by HPLC-MS

Collection and processing of samples.
Reagents and Supplies.

The following reagents and supplies are utilized in the Cholate Shunt and Cholate Clearance Test procedures. If the patient is undergoing only the oral cholate clearance test, the IV Solution and 25% Human Albumin for injection are omitted.

IV Solution-20 mg 24-$^{13}$C-Cholic Acid in 5 cc 1 mEq/ml Sodium Bicarbonate

PO test compounds 2,2,4,4-$^2$H (40 mg) and Sodium Bicarbonate (600 mg)

25% Human Albumin for injection (5 mls) to be added to 24-$^{13}$C-Cholic Acid solution.

IV supplies, including 250 mls NS, indwelling catheter, 3-way stopcock.

10 cc syringes for administering IV test compounds 7 cc red top tubes for sample collection 3 ml crovials for serum storage Needle discard bucket Apple or Grape (non-citrus) juice for oral test compounds Timer Centrifuge Transfer pipets Patient preparation.

It is ascertained that the patient has no allergic reaction to latex. It is further ascertained that the patient has had nothing to eat or drink (NPO), except water, since midnight the night before the test day. The patient height and weight are measured and recorded. The patient is fitted with an IV with a three-way stopcock and normal saline to keep open (NS TKO) is placed before the test begins.

Cholate Compound Stock Solutions

Test Compound Preparation

The Oral Solution is utilized for either or both of the oral cholate clearance test and/or the cholate shunt assay. The oral solution consisting of 2,2,4,4-$^2$H-Cholic acid (40 mg) and Sodium Bicarbonate (600 mg) is dissolved in about 10 cc water 24 hours prior to testing by mixing vigorously. The solution is stored in either the refrigerator or at room temperature. Just prior to administration, grape or apple (non-citrus) juice is added to the mixture. The juice solution is mixed well and poured into cup for patient to drink. The cup is rinsed with extra juice which is administered to the patient.

The IV Solution is utilized for either or both of the IV cholate clearance test and/or the cholate shunt assay. A formulation of 20 mg Cholic Acid-24-$^{13}$C in 5 cc 1 mEq/ml Sodium Bicarbonateis prepared by pharmacy staff. The Test dose is 20 mg Cholic Acid-24-$^{13}$C in 10 cc diluent. If vial is frozen, it is allowed to thaw completely. Just prior to beginning the test, the Cholic Acid-24-$^{13}$C solution is mixed with albumin as follows (this method prevents loss of test compound during mixing process). Draw up all of 24-$^{13}$C-Cholic Acid solution (about 5 cc) in a 10 cc syringe. Draw up 5 cc albumin in another 10 cc syringe. Detach needle from the 24-$^{13}$C-cholate syringe and attach a 3-way stopcock. Detach needle from albumin syringe and inject albumin through stopcock into 24-$^{13}$C Cholate syringe. Draw a little air into the bile acid/albumin syringe and mix solutions gently by inverting syringe several times. Expel air.

Test Compound Administration

Collect baseline samples before test compounds are given. The time these specimens are collected should be recorded on sample collection record sheet. Administration of test compounds is performed as follows. Start timer. Record 24 hour clock time as T=0. Record time. At T=1-3 minutes administer oral compounds. Have the patient drink the oral solution and juice. Rinse cup with more juice and have patient drink rinse. Record timer time. At T=4-5 minutes-using the 3-way stopcock administer the IV push of 20 mgs $^{13}$C Cholic acid in 5 mls 25% Human Albumin. Record timer time. Return line to NS through 3-way stopcock.

Specimen Collection

Collect all samples via the 3-way stopcock with 0.5 ml discard before each sample to prevent dilution or cross-contamination of samples. Collect 5 ml red tops at the following times. (T=timer time).

a. T=10 minutes, collect 5 minute, record timer time;
b. T=25 minutes, collect 20 minute, record timer time;
c. T=50 minutes, collect 45 minute, record timer time;
d. T=65 minutes, collect 60 minute, record timer time;
e. T=95 minutes, collect 90 minute, record timer time.

Specimen Handling

Red top tubes are allowed to clot at room temperature for at least 30 minutes. All blood tubes are spun for 10 minutes at 3000 rpm. Serum is removed to properly labeled vials and frozen at −20° C. until samples are transported.

Preparation of Cholate Compound Stock Solutions.

Accurate determination of cholate clearances and shunt is dependent on accurate calibration standards. Concentrations of cholic acid compounds in stock solutions must be accurate and reproducible. Very accurate (error <0.5%) portions of the cholic acid powders are weighed and glass weighing funnels and washes of 1 M NaHCO$_3$ are used to ensure quantitative transfer of the powder to the flask. Volumetric flasks are used to ensure accurate volumes so that the final concentrations of the primary stock solutions are accurate. Calibrated air displacement pipettes are used to dispense accurate volumes of the primary stock solutions that are brought to full volume in volumetric flasks to prepare secondary stock solutions that are also very accurate. Secondary stock solutions are used to prepare the standard curve samples, accuracy and precision samples, recovery samples, quality control samples, selectivity samples, and stability samples as described in the appropriate SOPs.

The following reagents are required.

1 M NaHCO$_3$ 0.1 M NaHCO$_3$ 0.1 M NaHCO$_3$/2% BSA

Methanol, LCMS grade

Water, CLRW grade (Clinical Laboratory Reagent Water)

Cholic Acid, purity 98%

Chenodeoxycholic Acid, purity 98%

[24-$^{13}$C]-Cholic Acid, 99 atom % $^{13}$C

[2,2,4,4-$^2$H]-Cholic Acid, 98 atom % $^2$H.

All primary stock solutions are prepared at a concentration of 250 uM using Table 8 below.

TABLE 8

Cholate compound primary stock solutions.

|  | cholic acid | 13-C cholic acid | 4-D cholic acid | chenodeoxcholic acid |
| --- | --- | --- | --- | --- |
| MW | 408.56 | 409.59 | 412.60 | 392.56 |
| purity | 98.0% | 99.0% | 98.0% | 98.0% |
| volume | 100 ml | 100 ml | 100 ml | 100 ml |
| conc | 250 uM | 250 uM | 250 uM | 250 uM |
| weight | 10.42 mg | 10.34 mg | 10.53 mg | 10.01 mg |

Primary stock solutions are prepared separately in 0.1 M NaHCO$_3$ and in methanol as follows. Weigh out the appropriate amount of cholic acid compound (+/−0.05 mg) in a glass weighing funnel. Transfer the powder to a 100 ml volumetric flask. Use either methanol or 0.1M NaHCO$_3$ to rinse any residual powder from the funnel into the flask. Bring to a final volume of 100 ml with methanol and mix well. Label flask with an expiration of 1 month. Store at −20° C.

The unlabeled cholic acid is prepared as a 50 uM internal standard in either MeOH or 0.1 M NaHCO$_3$ as follows. Pipette 2.0 ml of the appropriate 250 uM CA primary standard into a 10 ml volumetric flask. Bring to a total volume of 10 ml with 0.1 M NaHCO$_3$ or methanol and mix well. Label flask with an expiration of 1 year. Store at 4° C.

[24-$^{13}$C]-Cholic Acid secondary stock solutions made in methanol are shown in Table 9. Each secondary stock solution into the appropriate 15 ml glass screw top test tube. Tubes are securely capped and sealed with several layers of parafilm and stored at −20° C.

TABLE 9

[24-$^{13}$C]-Cholic acid secondary stock solutions in methanol.

| final assay concentration uM | Secondary Stocks uM | 250 uM 13C-CA (m) ul | | Methanol ml | | Total ml |
|---|---|---|---|---|---|---|
| 0.20 | B (m) | 2.0 | 80 + | 9.92 | = | 10.00 |
| 1.00 | D (m) | 10.0 | 400 + | 9.60 | = | 10.00 |
| 6.00 | F (m) | 60.0 | 2400 + | 7.60 | = | 10.00 |
| | | | 2880 | 27.12 | | 30.00 |

[2,2,4,4-$^2$H]-Cholic Acid secondary stock solutions made in methanol are shown in Table 10. Each secondary stock solution into the appropriate 15 ml glass screw top test tube. Tubes are securely capped and sealed with several layers of parafilm and stored at −20° C.

TABLE 10

[2,2,4,4-$^2$H]-Cholic acid secondary stock solutions in methanol.

| final assay concentration uM | Secondary Stocks uM | 250 uM 4D-CA (m) ul | | Methanol ml | | Total ml |
|---|---|---|---|---|---|---|
| 0.30 | I (m) | 3.0 | 120 + | 9.88 | = | 10.00 |
| 1.00 | K (m) | 10.0 | 400 + | 9.60 | = | 10.00 |
| 3.00 | L (m) | 30.0 | 1200 + | 8.80 | = | 10.00 |
| | | | 1720 | 28.28 | | 30.00 |

[24-$^{13}$C]-Cholic Acid secondary stock solutions made in 0.1 M NaHCO$_3$ and BSA are shown in Table 11. Each secondary stock solution is transferred into the appropriate 15 ml screw top plastic tube, capped, sealed with several layers of parafilm and stored at 4° C.

TABLE 11

[24-$^{13}$C]-Cholic acid secondary stock solutions in 0.1 M NaHCO$_3$ and BSA.

| final assay concentration uM | Secondary Stocks uM | 250 uM 13C-CA ul | | 0.1 M NaHCO3 ml | | 2% BSA ml | | Total ml |
|---|---|---|---|---|---|---|---|---|
| 0.10 | A | 1.0 | 40 + | 4.96 | + | 5.00 | = | 10.00 |
| 0.20 | B | 2.0 | 80 + | 4.92 | + | 5.00 | = | 10.00 |
| 0.60 | C | 6.0 | 240 + | 4.76 | + | 5.00 | = | 10.00 |
| 1.00 | D | 10.0 | 400 + | 4.60 | + | 5.00 | = | 10.00 |
| 2.00 | E | 20.0 | 800 + | 4.20 | + | 5.00 | = | 10.00 |
| 6.00 | F | 60.0 | 2400 + | 2.60 | + | 5.00 | = | 10.00 |
| 10.00 | G | 100.0 | 4000 + | 1.00 | + | 5.00 | = | 10.00 |
| | | | 7960 | 27.04 | | 35.00 | | 70.00 |

[2,2,4,4-$^2$H]-Cholic Acid secondary stock solutions made in 0.1 M NaHCO$_3$ and BSA are shown in Table 12. Each secondary stock solution is transferred into the appropriate 15 ml screw top plastic tube, capped, sealed with several layers of parafilm and stored at 4° C.

TABLE 12

[2,2,4,4-$^2$H]-Cholic acid secondary stock solutions in 0.1 M NaHCO$_3$ and BSA.

| final assay concentration uM | Secondary Stocks uM | 250 uM 4D-CA ul | | 0.1 M NaHCO3 ml | | 2% BSA ml | | Total ml |
|---|---|---|---|---|---|---|---|---|
| 0.10 | H | 1.0 | 40 + | 4.96 | + | 5.00 | = | 10.00 |
| 0.30 | I | 3.0 | 120 + | 4.88 | + | 5.00 | = | 10.00 |
| 0.50 | J | 5.0 | 200 + | 4.80 | + | 5.00 | = | 10.00 |
| 1.00 | K | 10.0 | 400 + | 4.60 | + | 5.00 | = | 10.00 |
| 3.00 | L | 30.0 | 1200 + | 3.80 | + | 5.00 | = | 10.00 |
| 5.00 | M | 50.0 | 2000 + | 3.00 | + | 5.00 | = | 10.00 |
| | | | 3960 | 26.04 | | 30.00 | | 60.00 |

The secondary stock solutions as prepared above are utilized in preparation of accuracy and precision samples in human serum with unlabeled cholate as an internal standard. The secondary stock solutions are used in preparation of recovery samples with addition of unlabeled cholate as an internal standard.

In order to accurately measure patient liver function with the cholate shunt assay, the two different stable isotope cholate compounds must each be accurately quantified in patient serum. In order to do this, the accuracy, precision, and recovery of each of the two standard curves must be validated over their respective ranges of concentrations.

The accuracy and precision of an assay are assessed by running multiple replica samples at the lower limit of quantification (LLOQ), low, medium, and high range of concentrations. Accuracy is the closeness of the average measured value to the actual value. Precision is the reproducibility of the measured value as indicated by the CV. The recovery is assessed by comparing the detector response of the analyte extracted from serum relative to that of pure analyte measured at low, medium, and high concentrations.

Preparation of Quality Control Samples

The FDA provides guidance as to acceptable levels of accuracy and precision of analytical methods. See, for example, Bioanalytical Method Validation, May 2001, Section VI. Application of Validated Method to Routine Drug Analysis. Once the analytical method has been validated for routine use, its accuracy and precision should be monitored regularly to ensure that the method continues to perform satisfactorily. To achieve this objective, a number of QC samples are prepared separately and should be analyzed with processed test samples at intervals based on the total number of samples. The QC samples are run in duplicate at three concentrations (one near the lower limit of quantification (LLOQ) (i.e., 3×LLOQ), one in midrange, and one close to the high end of the range) and should be incorporated in each assay run. The number of QC samples (in multiples of three) will depend on the total number of samples in the run. The results of the QC samples provide the basis of accepting or rejecting the run. At least four of every six QC samples should be within 15% of their respective nominal value. Two of the six QC samples may be outside the 15% of their respective nominal value, but not both at the same concentration.

The QC samples must cover the high, middle, and low ranges of both standard curves. The QC samples are designed to closely simulate the actual concentrations of labeled compounds found in patient serum over the time course of the testing. The [24-$^{13}$C]-CA concentration is very high at the early time point and falls exponentially to medium and low concentrations. The [2,2,4,4-$^2$H]-CA concentration is very low at the early time point, rises to its highest value in the middle time points and then falls to a medium concentration.

Supplies

The following supplies are utilized to prepare the QC samples used in the Cholate Shunt and Cholate Clearance Test procedures. If the patient samples are undergoing only the oral cholate clearance test, the [24-$^{13}$C]-CA QC samples can be omitted.

Human Serum AB (Gemini Bio-Products #100-512)
Unlabeled Cholate Internal Standard Stock Solution (IS; 50 uM Cholic Acid in 0.1M NaHCO$_3$)
[24-$^{13}$C]-Cholic Acid and [2,2,4,4-$^2$H]-Cholic Acid Secondary Stock Solutions in 0.1 M NaHCO$_3$/1% BSA:
B 2.0 uM [24-$^{13}$C]-CA
D 10.0 uM [24-$^{13}$C]-CA
F 60.0 uM [24-$^{13}$C]-CA
I 3.0 uM [2,2,4,4-$^2$H]-CA
K 10.0 uM [2,2,4,4-$^2$H]-CA
L 30.0 uM [2,2,4,4-$^2$H]-CA
10 ml volumetric flasks
P1000 air displacement pipette and 1 ml tips
New, clean cryovials Procedure for Preparation of Quality Control Samples for Cholate Clearance and Assays.

The [24-$^{13}$C]-Cholic Acid and [2,2,4,4-$^2$H]-Cholic acid QC samples are prepared as follows. For each set of QC samples, label 3 clean 10 ml volumetric flasks as "QC 1", "QC 2", and "QC 3" as shown in Table 13. Larger volumetric flasks can be used to prepare larger batches. Use 1/10 the nominal volume of the larger flasks as the amount of secondary stock solution to add as indicated below.

TABLE 13

QC samples.

| Tubes | [24-$^{13}$C]-CA | [2,2,4,4-$^2$H]-CA |
|---|---|---|
| QC1 | 1.00 ml F | 1.00 ml I |
| QC2 | 1.00 ml D | 1.00 ml L |
| QC3 | 1.00 ml B | 1.00 ml K |

Using a P1000, add 1.0 ml of the appropriate [24-$^{13}$C]-CA stock solution and 1.0 ml of the appropriate [2,2,4,4-$^2$H]-CA stock solution to the appropriate flasks as indicated in Table 13. Bring each flask to an exact total of 10.0 ml with human serum. Securely cap each flask and mix well by inversion several times. Label 8 cryovials as "QC 1", 8 as "QC 2", and 8 as "QC 3". Aliquot 1.2 ml of each QC mixture into the appropriate vials. Store the QC samples frozen at −80° C. QC samples have an expiration of 1 year.

High Pressure Liquid Chromatography-Mass Spectoscopy (HPLC-MS) Sample Preparation In order to ensure accurate liver function testing, the labeled cholate test compounds must be isolated and identified from patients' serum samples. Cholate compounds are amphipathic molecules with both hydrophobic and hydrophilic regions. Cholates are also carboxylic acids that can exist in either an uncharged free acid form (cholic acid) or a charged carboxylic acid form (cholate) depending on pH. These properties can be exploited to isolate cholate compounds from serum. The use of HPLC/MS as opposed to GC/MS, allows analysis of cholate without sample derivitization.

Reagents, Supplies and Equipment

The following reagents are prepared and used in the HPLC-MS sample preparation.

Water, CLRW grade (Clinical Laboratory Reagent Water)
Methanol, LCMS grade
Diethyl Ether, ACS grade
Unlabeled Cholic Acid Internal Standard (IS) Primary Stock Solution (50 uM CA in 0.1 M NaHCO$_3$)
Quality Control Samples (prepared as described above)
1.0 N NaOH (dissolve 20 g NaOH in 500 ml water)
0.01 N NaOH (dilute 1.0 N NaOH 1 to 100 with water)
10% Methanol (add 100 ml Methanol to a 1 L cylinder and bring to 1.0 L with water)
90% Methanol (add 900 ml Methanol to a 1 L cylinder and bring to 1.0 L with water)
0.2 N HCl (add 1.0 ml ACS grade Concentrated HCl slowly with stirring to 57.0 ml water)
Mobile Phase (10 mM Ammonium Acetate/60% Methanol)
Disposable 16×100 and 13×100 test tubes
P1000 air displacement pipette and 1 ml tips
P100 air displacement pipette and 0.2 ml tips
Repeater Pipette
Vortex Mixer
SPE cartridges (Bond Elut LRC C18 OH, 500 mg, Varian, Inc,)
Vacuum Manifold
Speed-Vac
Benchtop centrifuge
Speed-Vac vented to fume hood
Bath Sonicator
Repeater Dispensers for water, methanol, 10% methanol, and 90% methanol Remove patient serum samples and a set of QC samples (2 each of QC1, 2, and 3) from the freezer and allow them to thaw to room temperature. Personal protective equipment (PPE) including lab coat, gloves, eye protection must be worn. All eluates and equipment must be disinfected. Pipettes and tips that come in contact with the sample must be discarded into hazardous waste.

Label a set of test tubes (16×100) for each patient with that patient's initials and the time point code (5 min is 1, 20 min is 2, 45 min is 3, 60 min is 4, 90 min is 5). Using a P1000 pipette, transfer 0.50 ml of patient's serum from the appropriate collection tube into the appropriate test tube.

Label a set of test tubes (16×100) for each QC sample (QC1a, QC1b, QC2a, QC2b, QC3a, QC3b). Using a P1000, transfer 0.50 ml of each QC sample into the appropriate test tube.

Label 2 test tubes (13×100) as STD1 and STD2.

To each patient sample and each QC sample and each STD sample tube, add 50 ul of the Unlabeled Cholic Acid Internal Standard (IS) Primary Stock Solution using a Repeater Pipette.

Set aside the STD tubes for later acidification and ether extraction in step 21.

To each patient sample tube and QC sample tube add 1.0 ml of 0.01 N NaOH with a Repeater pipet and vortex 30 sec.

Label a set of SPE cartridges with one for each patient serum and QC sample to be processed.

In the hood add 5 ml Methanol with a repeater dispenser to each cartridge. This step may be done on a vacuum manifold with high vacuum or by gravity. This wets the resin bed with solvent. Once the top of the liquid reaches the top of the frit add the next solution. Avoid letting the cartridges run dry.

Add 10 ml Water with the repeater dispenser to each cartridge. This equilibrates the resin bed to prepare it for binding cholate compounds. This step may be done on the vacuum manifold on high vacuum or by gravity.

To each SPE cartridge add the appropriate sample. The cholate compounds will bind to the resin bed. To each sample test tube add a 1 ml water rinse with the repeater, vortex, and add this rinse to the appropriate cartridge. Allow the sample to run by gravity for 20 minutes or longer then may use low vacuum ≤3 inches Hg to pull sample through.

After the sample has completely entered the resin bed, add 2.5 ml Water to each SPE cartridge with the repeater dispenser. This washes the column resin bed. Use low vacuum ≤3 inches Hg.

To each SPE cartridge add 2.5 ml 10% Methanol with the repeater dispenser. This further washes the column resin bed. Use low vacuum ≤3 inches Hg.

Label a set of test tubes (13×100) with one for each patient sample and each QC sample.

Place each test tube in a rack and on top place its matching SPE cartridge.

To each SPE cartridge add 2.5 ml 90% Methanol with the repeater dispenser. This elutes the cholate compounds which are collected into the test tubes.

Place the test tubes in the Speed-Vac and centrifuge under vacuum with high heat for 45 min to reduce eluate volume and to remove methanol which interferes with ether extraction.

To each tube from the Speed-Vac and to each of the STD tubes, add 0.5 ml of 0.2 N HCl with the Eppendorf Repeater Pipette and vortex 30 sec. This acidification converts the cholate compounds into their free acid form for ether extraction.

In the fume hood, to each tube add 3 ml of diethyl ether and vortex vigorously for 30 sec. This extracts the free acid form of the cholate compounds into the ether phase.

Centrifuge 5 minutes at a minimum of 5000 rpm to accelerate phase separation.

Label another set of test tubes (13×100) one for each sample.

Carefully collect the upper ether layer and transfer to the new test tubes.

Place the ether extracts in the Speed-Vac vented to the fume hood and centrifuge under vacuum without heat until samples are dry. Alternatively, samples can be dried with a gentle stream of $N_2$ gas.

Add 100 ul Mobile Phase to dried samples, vortex 30 sec and sonicate.

Transfer samples to Agilent 1.5 ml vials and cap.
HPLC/MS Parameters and System Preparation
Reagents, Supplies and Equipment The following reagents are prepared and used in the HPLC-MS sample analysis.
Water, Clinical Laboratory Reagent Water (CLRW)
Methanol LCMS grade
10 mM Ammonium Acetate water
10 mM Ammonium Acetate methanol
Mobile Phase: 60% 10 mM Ammonium Acetate Methanol/ 40% 10 mM Ammonium Acetate Water
Volumetric flasks, appropriate sizes
Graduated cylinder The following instruments and supplies are used in the HPLC-MS sample analysis.
Calibrated analytical balance
HPLC/MS instrument: Agilent 1100 series Liquid Chromatograph Mass Spectrometer equipped with a G1956A multimode source, automatic sampler, HP Chemstation Software or equivalent.
Agilent Eclipse XDB C8, 2.1×100 mm 3.5 um liquid chromatograph column
Solvent Filter Degasser
0.22 μm nylon filters The solvents and mobile phase are each prepared, filtered with a 0.22 μm nylon filter and degassed. Solvents and mobile phase each expire 48 hours after preparation.

The LCMS system is prepared and tuned; the column is stabilized at 40° C. and conditioned by running the mobile phase for 30 min. The samples are loaded to the autosampler. The column flow rate is 0.4 ml/min of isocratic mobile phase buffer; 60% 10 mM Ammonium Acetate Methanol/40% 10 mM Ammonium Acetate Water. 5 microliters of each sample is injected by the autosampler. The MS is run in multimode electrospray (MM-ES) ionization with atmospheric pressure chemical ionization (APCI) ionization. Selected ion monitoring is performed at 407.30, 408.30 and 411.30 m/z. Peaks are integrated by the system software. Three QC samples are assayed with each analytical run. The concentration of the QC samples must fall within 15% accuracy.

Example 13

Hepatic Impairment Measured by Quantitative Tests of Liver Function (QLFTs) Predicts Clinical Outcome in Patients with Advanced Fibrosis Liver biopsy is the current standard for defining disease severity and predicting risk for clinical outcomes in patients with chronic hepatitis C. But, biopsy is invasive, inconvenient, risky, and prone to sampling error. QLFTs noninvasively measure hepatic impairment and correlate with biochemical and histological indices of disease severity. The ability of QLFTs to predict clinical outcomes in compensated patients was evaluated prospectively, controlling for platelet count and histologic cirrhosis.

In this example, 227 patients, enrolled in the HALT-C Trial, had baseline QLFTs and were randomized to either no treatment (N=120) or peginterferon alfa-2a (PegIFN) 90 μg/week (N=107), and followed for 66 months for non-HCC, liver-related clinical outcomes. Since PegIFN did not affect clinical or histological outcomes (DiBisceglie et al., Dec. 4, 2008, Prolonged therapy of advanced chronic hepatitis C with low-dose peginterferon, NEJM, 359:2429-2441), these two groups were combined for analyses. QLFTs included cholate clearance po, methionine breath test, cholate shunt, antipyrine clearance, perfused hepatic mass, liver and spleen volume from SPECT liver-spleen scan, cholate clearance iv, caffeine elimination rate, MEGX concentration, and galactose elimination capacity (GEC). The hazard ratio (HR) of clinical outcomes was based on comparing the third of patients with worst function to those with medium function and medium function to high function. Results are shown in Table 14. The independence of each QLFT in predicting clinical outcomes was assessed in multivariate analyses that included platelet count and histologic cirrhosis.

Results of the trial showed 46 of the 227 patients (20%) experienced 97 outcomes: CTP score ≥7 (N=34), death (N=30), ascites (N=18), variceal bleed (N=3), encephalopathy (N=2), and SBP (N=1).

TABLE 14

Hazard Ratio (HR) of Clinical Outcome for Various QLFTs.

| | HR per tertile (95% CI) | |
|---|---|---|
| QLFT | Univariate | Multivariate |
| Cholate Clearance po | 4.37 (2.63-7.30) | 3.23 (1.84-5.65) |
| Methionine Breath Test | 3.06 (1.83-5.13) | 2.42 (1.43-4.12) |
| Cholate Shunt | 3.26 (2.06-5.17) | 2.35 (1.44-3.84) |
| Antipyrine Clearance | 2.59 (1.57-4.29) | 2.30 (1.39-3.80) |
| Perfused Hepatic Mass | 3.62 (2.26-5.81) | 2.12 (1.26-3.89) |
| Spleen Volume | 3.45 (2.15-5.53) | 1.92 (1.12-3.31) |
| Cholate Clearance iv | 2.13 (1.43-3.17) | 1.83 (1.23-2.73) |
| Caffeine Elimination | 2.24 (1.48-3.38) | 1.81 (1.20-2.73) |
| MEGX | 1.89 (1.29-2.78) | 1.67 (1.14-2.45) |
| Galactose Elimination Capacity | 1.89 (1.29-2.78) | 1.67 (1.14-2.45) |

HR for clinical outcomes between lowest and highest tertile is HR squared.

Cholate Clearance po, Methionine Breath Test, Cholate Shunt, Antipyrine Clearance, Perfused Hepatic Mass, and Spleen Volume were the most robust independent predictors of clinical outcomes. The cutoff values for oral cholate clearance (HepQuant-Oral) and cholate shunt (HepQuant-Dual) for defining the group of HCV patients at greatest risk for future hepatic decompensation were: Oral Cholate Clearance <11 mL/(min kg); and Cholate Shunt ≥39%. It was concluded that measurement of hepatic impairment by QLFTs outperforms histologic cirrhosis in prediction of clinical outcomes and provides a noninvasive means for assessing disease severity and counseling patients.

Example 14

Interval Clinical Outcomes in Relation to the Results of QLFTs at each Visit

In this example, Hepatitis C patients from the HALT-C trial were assessed by oral cholate clearance and cholate shunt assays at 0, 24 and 48 months. Patients were monitored over a six year period. The cholate shunt (CA Sh) and oral cholate clearance (CA Cl oral) were determined at the beginning of each time interval. Cutoffs for cholate shunt that predicts the 2-year risk of decompensation were determined for cholate shunt and oral cholate clearance assays. "No outcome" or "none" in FIGS. 11-14 refers to no outcome prior to or within the follow-up (f/u) interval. "Outcome" refers to a first clinical outcome that occurred within the follow-up interval.

Figure 11:
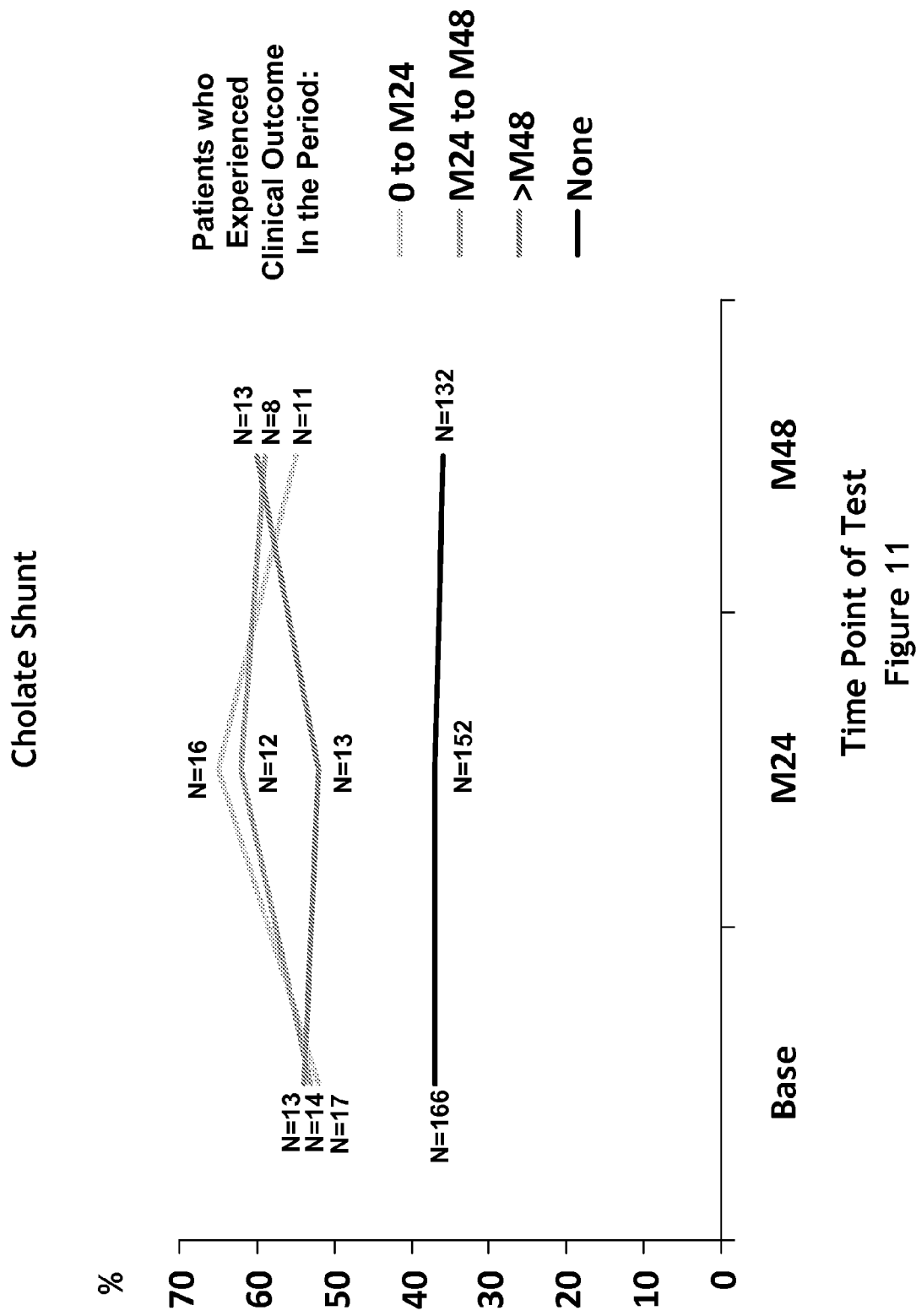
FIG. 11 shows average cholate shunt values and the number of hepatitis C patients at each time interval who experienced first clinical outcome, or no outcome, in the periods 0 to 24 months, 24 to 48 months and after 48 months.

FIG. 11 shows average cholate shunt values and the number of hepatitis C patients at each time interval who experienced first clinical outcome, or no outcome, in the periods 0 to 24 months, 24 to 48 months and after 48 months. The cutoff for cholate shunt that predicts the 2-year risk of decompensation is shown in FIG. 12.

Figure 13:
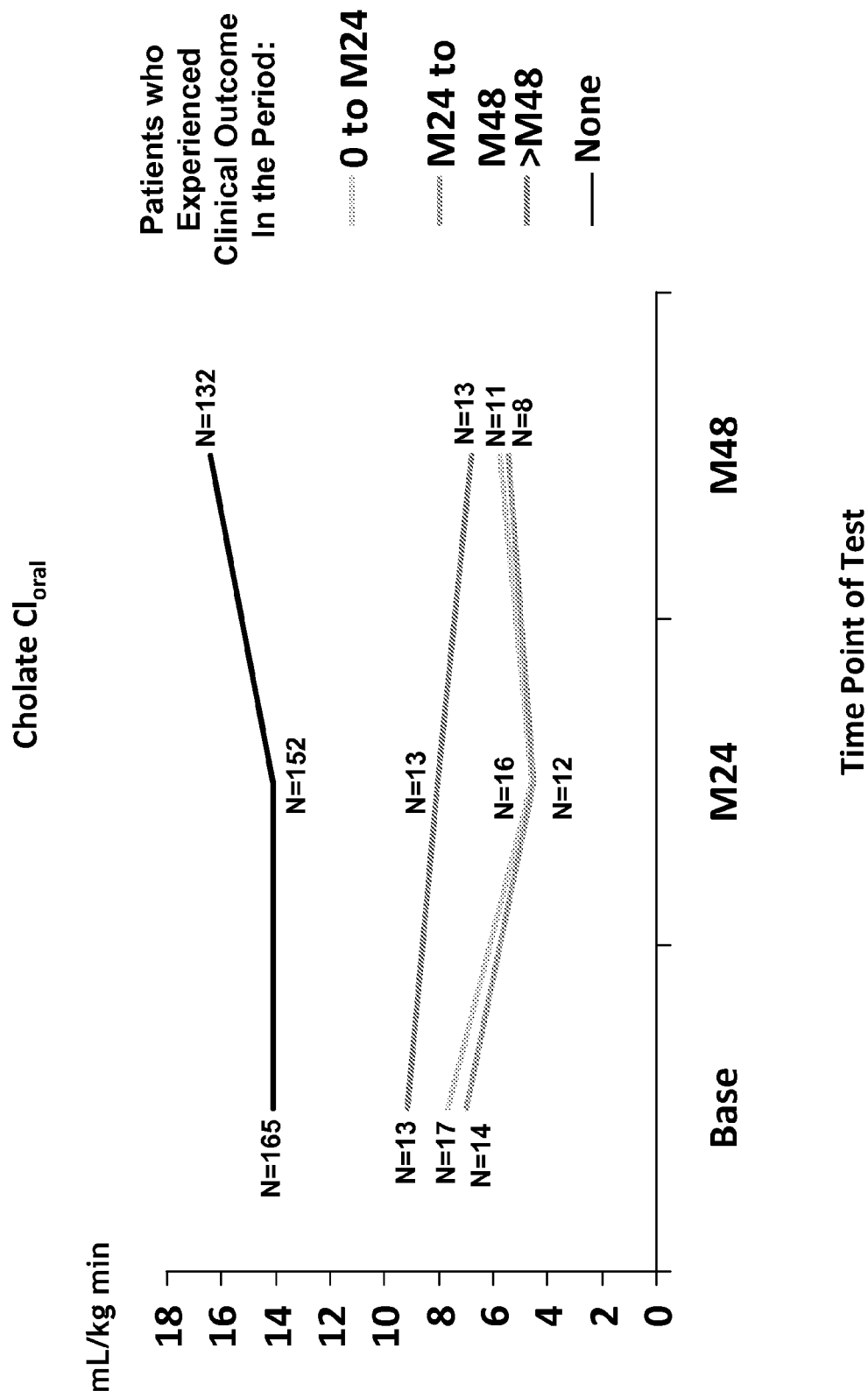
FIG. 13 shows average oral cholate clearance values and the number of hepatitis C patients at each time interval who experienced first clinical outcome, or no outcome, in the periods 0 to 24 months, 24 to 48 months and after 48 months.

FIG. 13 shows average oral cholate clearance values and the number of hepatitis C patients at each time interval who experienced first clinical outcome, or no outcome, in the periods 0 to 24 months, 24 to 48 months and after 48 months. The cutoff for oral cholate clearance that predicts the 2-year risk of decompensation is shown in FIG. 14.

Example 15

Cholate Shunt is Predictive of Ishak Fibrosis Score

Figure 15:
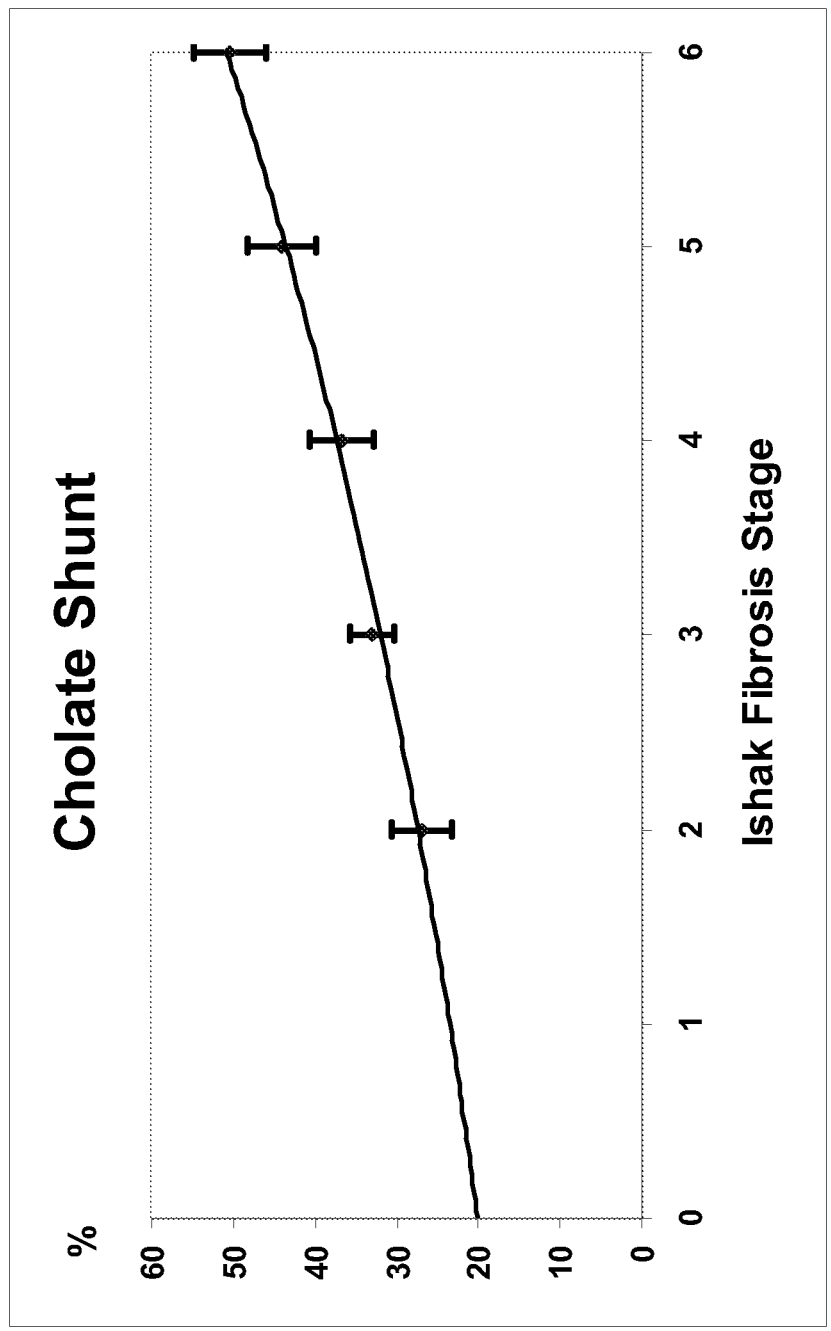
FIG. 15 shows the correlation between mean cholate shunt and Ishak stage of fibrosis for Hepatitis-C patients (n=282).

Hepatitis C patients (n=282) from the HALT-C trial were assessed by cholate shunt assay and liver biopsy. The patients were fairly evenly distributed across the fibrosis stages. Results are shown in FIG. 15. As Ishak fibrosis score increases, cholate shunt increases. The error bars indicate 95% CI limits for the means of Ishak fibrosis score. Mean (+/−) for cholate shunt for fibrosis stages 2-6 were 27+/−9%; 33+/−13%; 37+/−15%; 44+/−; and 51+/−17%, respectively. Table 15 shows values derived from the equation fitting the mean values in FIG. 15; 95% CI was defined from the standard errors for cholate shunt at each Ishak stage. The average 95% CI based on standard errors was +/−10% of the mean.

TABLE 15

Use of Cholate Shunt Test Results as an Estimate of Stage (Ishak) of Hepatic Fibrosis.

| | Ishak Fibrosis Score | |
|---|---|---|
| Shunt | Result | 95% CI |
| 20% | 0 | 0 to 0.6 |
| 25% | 1.4 | 0.7 to 2.0 |
| 30% | 2.6 | 1.9 to 3.2 |
| 35% | 3.6 | 2.9 to 4.2 |
| 40% | 4.4 | 3.8 to 5.1 |
| 45% | 5.2 | 4.5 to 5.8 |
| 50% | 5.9 | 5.2 to 6 |
| >50% | 6 | |

At a cholate shunt of 30%, the mean Ishak fibrosis score was 2.6. The cholate shunt value was found to be predictive of the Ishak fibrosis score by about +/−0.5 fibrosis units; roughly the variation seen when two pathologists read the same biopsy. Cholate shunt can potentially be used as a non-invasive alternative to liver biopsy in determination of Ishak fibrosis score. See Everson et al., "The spectrum of hepatic functional impairment in compensated chronic hepatitis C: results from the Hepatitis C Anti-viral Long-term Treatment against Cirrhosis Trial", Aliment. Pharmacol. Ther. 27, 798-809.

Example 16

A Kit for determination of Cholate Shunt and IV and Oral Cholate Clearance

A kit containing the following components can be provided to the physician for the purpose of administering differentially labeled stable cholate isotopes for determination of oral cholate clearance, IV cholate clearance and cholate shunt. The kit also provides certain supplies for patient sample collection. Test compound preparation, patient administration and sample collection are performed according to package insert directions. Patient samples are prepared according to package insert directions. See for example, the testing protocol in Example 12, above. The samples are frozen and shipped to a central reference laboratory for analysis. An analytical report is generated by the reference laboratory and can be sent to the physician by e-mail, fax or mail. In this example, 11 components are provided in a single kit as outlined in Table 16.

TABLE 16

Kit contents.

| | For IV Administration | |
|---|---|---|
| 1 | $^{13}$C Cholic Acid in bicarbonate solution [USP] (20 mg in 5 ml, sterile) | 1 Bottle |
| 2 | Human Serum Albumin [USP] (5 ml 25% w/v, sterile) | 1 Bottle |

TABLE 16-continued

Kit contents.

For Oral Administration

| | | |
|---|---|---|
| 3 | Powdered $^2$H Cholic acid (40 mg powder or in solution) | 1 Bottle |

For Blood Sample Collection, Serum Separation, & Transport

| | | |
|---|---|---|
| 4 | Labeled Blood-Serum Collection Tubes (6 count, sterile) | 6 Tubes |
| 5 | Labeled Transport Vials with Internal Cholic Acid Standard (6 count, 0.5 ml minimum volume) | 6 Tubes |

Containers and Shipping

| | | |
|---|---|---|
| 6 | Shipping/Sample return box (Use same box) | 1 Box |
| 7 | Box label | 1 Label |
| 8 | Return mailing instructions insert | 1 Insert |
| 9 | Package insert | 1 Insert |
| 10 | Return label | 1 Label |
| 11 | Prepaid return shipping | 1 Label |

In another example, the kit comprises an oral dose of a distinguishable cholate and sample tubes for collection of samples over a period of less than 3 hours after administration of the distinguishable agents. In another example, a kit may comprise components necessary for a test period of 90 minutes post administration of an isotopically labeled cholic acid.

All of the COMPOSITIONS and/or METHODS and/or APPARATUS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

I claim:

1. A method for assessment of hepatic function in a subject, the method comprising:
    (a) receiving a plurality of blood or serum samples collected from a subject having, or suspected of having or developing, a hepatic disorder, following oral administration of a stable isotope labeled cholic acid to the subject, wherein no additional cholic acid compound is intravenously co-administered, and wherein the samples have been collected from the subject over intervals of two to seven time points spanning a time period of from 5 to at least 60, but no more than 180 minutes after administration;
    (b) measuring concentration of the labeled cholic acid in each sample;
    (c) generating an individualized oral clearance curve from the concentration of the labeled cholic acid in each sample comprising using a computer algorithm curve fitting to a model oral stable isotope labeled cholic acid clearance curve;
    (d) computing the area under the individualized oral clearance curve (AUC) and dividing the dose (in mg) by AUC of the orally administered stable isotope labeled cholic acid to obtain the oral cholic acid clearance in the subject; and
    (e) comparing the oral cholic acid clearance in the subject to an oral stable isotope labeled cholic acid clearance cutoff value as an indicator of the relative hepatic function in the subject.

2. The method of claim 1 wherein the stable isotope labeled cholic acid is selected from $^{13}$C-labeled cholic acid or $^2$H-labeled cholic acid.

3. The method of claim 1, wherein collecting samples over an interval period of time comprises collecting samples over a period of about 90 minutes or less.

4. The method of claim 3, wherein the samples comprise blood samples collected from the subject at 5, 20, 45, 60 and 90 minutes post-administration.

5. The method of claim 1 wherein the measuring step comprises quantifying the isotopically labeled cholic acid in the samples by gas chromatography-mass spectrometry (GC-MS) or high pressure liquid chromatography-mass spectrometry (HPLC-MS).

6. The method of claim 1, further comprising at least one additional hepatic assessment test.

7. The method of claim 6, wherein the at least one additional hepatic assessment test is selected from the group consisting of clearance or metabolism of aminopyrine, clearance or metabolism of antipyrine, clearance or metabolism of bile acids other than cholate, clearance or metabolism of caffeine, clearance of or metabolism erythromycin, clearance or metabolism of nitroglycerin, clearance of or metabolism galactose, clearance or metabolism of indocyanine green, clearance or metabolism of lidocaine, clearance or metabolism of midazolam, clearance or metabolism of omeprazole, clearance or metabolism of dextromethorphan, clearance or metabolism of phenacetin, clearance or metabolism of methacetin, clearance or metabolism of methionine, ultrasonography, elastography, magnetic resonance imaging (MRI) elastography, liver-spleen scan, serum bilirubin analysis, alanine aminotransferase analysis, aspartate aminotransferase analysis, alkaline phosphatase analysis, prothrombin analysis, creatinine analysis, platelet count, blood count analysis, serum albumin and MELD (model for end-stage liver disease) score.

8. The method of claim 7 wherein the at least one additional hepatic assessment test is a multi-isotope test.

9. The method of claim 6, wherein the additional hepatic assessment test is a quantitative liver function test (QLFT).

10. The method of claim 9, wherein the quantitative liver function test (QLFT) is selected from a hepatic metabolic function test, a hepatic blood flow test or combination thereof.

11. The method of claim 10, wherein the hepatic metabolic function test is a multi-isotope caffeine test.

12. The method of claim 11, wherein the multi-isotope caffeine test comprises administering distinguishable caffeine solutions orally, intravenously or in combination thereof.

13. The method of claim 12, wherein the administering step comprises administering three distinguishable caffeine solutions to a subject at different time intervals.

14. The method of claim 13, wherein a single sample is obtained from the subject sometime after administration of the distinguishable caffeine solutions to assess clearance or metabolites of the caffeine in order to further assess the hepatic condition of the subject.

15. The method of claim 1 wherein the comparing of clearance of the stable isotope labeled cholic acid in the subject to the cutoff value is an indication of a need for at least one therapeutic treatment of the subject with a hepatic disorder.

16. The method of claim 15, wherein the at least one therapeutic treatment comprises an antiviral therapy.

17. The method of claim 15, wherein the hepatic disorder comprises chronic hepatitis C.

18. The method of claim 1 wherein the comparing of the clearance of the isotopically labeled cholic acid in the subject to the cutoff value is an indication of one or more of stage of fibrosis, presence of varices, presence of large varices at risk to bleed, inability to respond to peginterferon/ribavirin in chronic hepatitis C, hepatic improvement in response to antiviral therapy, future decompensation, hepatic functional impairment in cholestatic liver disease (primary sclerosing cholangitis, PSC) or prediction of clinical outcome in chronic hepatitis C in the subject.

19. The method of claim 1, wherein the step of comparing the clearance in the subject to a clearance cutoff is an indicator of future clinical outcome of at least one hepatic disorder in the subject.

20. The method of claim 19, wherein the cutoff value for oral cholate clearance for defining a hepatitis C patient at greatest risk for future hepatic decompensation is oral cholate clearance <11 mL/(min kg).

21. The method of claim 1, wherein the clearance cutoff value is derived from normal healthy controls, within a given individual over time, patients who respond to therapy, patients with large varices, patients with sustained virological response to antiviral therapy, patients unable to respond to antiviral therapy, patients with significant fibrosis, or patients with cirrhosis.

22. A method for assessment of a stage of hepatic fibrosis in a subject, the method comprising:
(a) receiving a plurality of blood or serum samples collected from a subject having, or suspected of having or developing, hepatic fibrosis, following oral administration of a dose of a first stable isotope labeled cholic acid ($dose_{oral}$) to the subject and simultaneous intravenous co-administration of a dose of a second stable isotope labeled cholic acid ($dose_{iv}$) to the subject, wherein the samples have been collected over intervals of two to seven time points spanning a time period of from 5 to at least 60, but no more than 180 minutes after administration;
(b) quantifying the concentration of the first and the second stable isotope labeled cholic acids in each sample by HPLC-MS;
(c) generating an individualized oral clearance curve from the concentration of the first labeled cholic acid in each sample comprising using a computer algorithm curve fitting to a model oral stable isotope labeled cholic acid clearance curve and computing the area under the individualized oral clearance curve (AUCoral);
(d) generating an individualized intravenous clearance curve from the concentration of the second labeled cholic acid in each sample by use of a computer algorithm curve fitting to a model intravenous stable isotope labeled cholic acid clearance curve and computing the area under the individualized intravenous clearance curve (AUCiv); and
(e) calculating the cholate shunt in the subject using the formula:

AUCoral/AUCiv×Doseiv/Doseoral×100%;

and
(f) comparing the cholate shunt in the subject to a stable isotope labeled cholate shunt cutoff value, wherein the cholate shunt in the subject compared to the cutoff value is an indicator of the stage of hepatic fibrosis of the subject.

23. The method of claim 22, wherein the collecting step comprises collecting samples over a period of about 90 minutes or less.

24. The method of claim 23, wherein the samples comprise blood or serum samples collected from the subject at 5, 20, 45, 60 and 90 minutes post-dose.

25. The method of claim 22 wherein the comparing of the cholate shunt in the subject to the cutoff value is an indicator of a need for at least one therapeutic treatment of the subject with a hepatic disorder.

26. The method of claim 25, wherein the at least one therapeutic treatment comprises an antiviral therapy.

27. The method of claim 25, wherein the hepatic disorder comprises chronic hepatitis C.

28. The method of claim 22, further comprising at least one additional hepatic assessment test.

29. The method of claim 28, wherein the at least one additional hepatic assessment test is selected from the group consisting of clearance or metabolism of aminopyrine, clearance or metabolism of antipyrine, clearance or metabolism of bile acids other than cholate, clearance or metabolism of caffeine, clearance of or metabolism erythromycin, clearance or metabolism of nitroglycerin, clearance of or metabolism galactose, clearance or metabolism of indocyanine green, clearance or metabolism of lidocaine, clearance or metabolism of midazolam, clearance or metabolism of omeprazole, clearance or metabolism of dextromethorphan, clearance or metabolism of phenacetin, clearance or metabolism of methacetin, clearance or metabolism of methionine, ultrasonography, elastography, magnetic resonance imaging (MRI) elastography, liver-spleen scan, serum bilirubin analysis, alanine aminotransferase analysis, aspartate aminotransferase analysis, alkaline phosphatase analysis, prothrombin analysis, creatinine analysis, platelet count, blood count analysis, serum albumin and MELD (model for end-stage liver disease) score.

30. The method of claim 28, wherein the additional hepatic assessment test is a quantitative liver function test (QLFT).

31. The method of claim 30, wherein the quantitative liver function test (QLFT) comprises a hepatic metabolic function test, a hepatic blood flow test or combination thereof.

32. The method of claim 22, wherein the step of comparing the shunt in the subject to the shunt cutoff is an indicator of future clinical outcome of at least one hepatic disorder in the subject.

33. The method of claim 32, wherein the cutoff value for shunt for defining a hepatitis C patient at greatest risk for future hepatic decompensation is cholate shunt ≥39%.

34. The method of claim 22, wherein the shunt cutoff value is derived from normal healthy controls, within a given individual over time, patients who respond to therapy, patients with large varices, patients with sustained virological response to antiviral therapy, patients unable to respond to antiviral therapy, patients with significant fibrosis, or patients with cirrhosis.

* * * * *